(12) United States Patent
Vertino

(10) Patent No.: US 6,911,306 B1
(45) Date of Patent: Jun. 28, 2005

(54) TMS1 COMPOSITIONS AND METHODS OF USE

(75) Inventor: Paula M. Vertino, Decatur, GA (US)

(73) Assignee: Emory University, Atlanta, GA (US)

( * ) Notice: Subject to any disclaimer, the term of this patent is extended or adjusted under 35 U.S.C. 154(b) by 394 days.

(21) Appl. No.: 09/691,763

(22) Filed: Oct. 18, 2000

Related U.S. Application Data

(60) Provisional application No. 60/159,975, filed on Oct. 18, 1999.

(51) Int. Cl.$^7$ .......................... C07H 21/04; C12Q 1/68
(52) U.S. Cl. .......................... 435/6; 435/91.2; 536/23.1
(58) Field of Search .................... 435/6, 91.2; 536/23.1

(56) References Cited

U.S. PATENT DOCUMENTS

| | | | | |
|---|---|---|---|---|
| 5,552,277 A | * | 9/1996 | Nelson et al. | 435/6 |
| 5,756,668 A | * | 5/1998 | Baylin et al. | 530/350 |
| 5,786,146 A | * | 7/1998 | Herman et al. | 435/6 |
| 6,369,196 B1 | | 4/2002 | Bertin | |

FOREIGN PATENT DOCUMENTS

| WO | WO96/35704 | 11/1996 |
|---|---|---|
| WO | WO 99/47669 | 9/1999 |
| WO | WO01/00826 | 1/2001 |

OTHER PUBLICATIONS

Dermer, Gerald. "Another Anniversary for the War on Cancer". Bio/Technology. vol. 12, Mar. 1994, p. 320.*
GenBank Submission; NIH/NCBI; Accession No. AF184072; Vertino, P.M.; Feb. 2, 2001.
GenBank Submission; NIH/NCBI; Accession No. AF184073; Vertino, P.M.; Feb. 2, 2001.
GenBank Submission; NIH/NCBI; Accession No. AF255794; Vertino, P.M.; Feb. 2, 2001.
GenBank Submission; NIH/NCBI; Accession No. AB032249; Masumoto, J., et al.; May 8, 2001.
GenBank Submission; NIH/NCBI; Accession No. AB023416; Masumoto, J., et al.; Oct. 18, 2000.
GenBank Submission; NIH/NCBI; Accession No. NM_013258; Masumoto, J., et al.; Nov. 2, 2000.
Conway, et al., "TMS1, a novel proapoptotic caspase recruitment domain protein, is a target of methylation-induced gene silencing in human breast cancers", Cancer Res., 60(22):6236–42 (2000). Abstract.
Conway, et al., "Identification of novel downstream targets of methylation-mediated gene inactivation", Proc. Amer. Assoc. Cancer Res., 40:321 Publisher American Association for Cancer Research (215) 440–9300—Poster Presentation Apr. 1999.
Vertino, et al., "De novo methylation of CpG island sequences in human fibroblasts overexpressing DNA (Cystosine-5-) –methyltransferase", Mol. Cell. Biol., 16(8):4555–4565 (1996).
Masumoto, et al., "ASC, a novel 22–kDa protein, aggregates during apoptosis of human promyelocytic leukemia HL–60 cells", J. Biol. Chem., 274(48):33835–33838 (1999).

Katzenellenbogen, et al., "Hypermethylation of the DAP–kinase CpG island is a common alteration in B–cell malignancies", Blood, 93(12):4347–53 (1999) ABSTRACT.
Bachman, et al., "Methylation–associated silencing of the tissue inhibitor of metalloproteinase–3 gene suggest a suppressor role in kidney, brain and other human cancers", Cancer Res., 59(4):798–802 ABSTRACT.
Esteller, et al., "Inactivation of the DNA repair gene O6–methylguanine–DNA methyltransferase by promoter hypermethylation is a common event in primary human neoplasia", Cancer Res., 59(4):793–7 (1999) ABSTRACT.
Esteller, et al., "Inactivation of glutathione S–transferase P1 gene by promoter hypermethylation in humanneoplasia", Cancer Res., 58(20):4515–8 (1998) ABSTRACT.
Herman, et al., "Incidence and functional consequences of hMLH1 promoter hypermethylation in colorectal carcinoma", Proc. Natl. Acad. Sci., 95(12):6870–5 (1998) ABSTRACT.
Herman, et al., "Methylation–specific PCR:a novel PCR assay for methylation status of CpG islands", Proc. Natl. Acad. Sci., 93(18):9821–6 (1996) ABSTRACT.
Graff, et al., "E–cadherin expression is silenced by DNA hypermethylation in human breast and prostrate carcinomas", Cancer Res., 55(22):5195–9 (1995) ABSTRACT.
Merlo, et al., "5'CpG island methylation is associated with transcriptional silencing of the tumour suppressor p16/CDKN2/MTS1 in human cancers", Nat. Med., 1(7):686–92 (1995) ABSTRACT.
Herman, et al., "Silencing of the VHL tumor–suppressor gene by DNA methylation in renal carcinoma", Proc. Natl. Acad. Sci., 91(21):9700–4 (1994) ABSTRACT.
Silva, et al., "Aberrant DNA methylation of the p16INK4a gene in plasma DNA of breast cancer patients", Br. J. Cancer, 80(8):1262–4 (1999) ABSTRACT.
Engelman, et al., "Sequence and detail organization of the human caveolin–1 and –2 genes located near the D7S522 locus (7q31.1) . . . " FEBS Lett., 448(2–3):221–30 (1999) ABSTRACT.
Catteau, et al., "Methylation of the BRCA1 promoter region in sporadic breast and ovarian cancer: correlation with disease characteristics", Oncogene, 18(11):1957–65 (1999) ABSTRACT.
Yu, et al., "NOEY2 (ARHI), an imprinted putative tumor suppressor gene in ovarian and breast carcinomas", Proc. Natl. Acad. Sci._USA, 96(1):214–9 (1999) ABSTRACT.

(Continued)

Primary Examiner—W. Gary Jones
Assistant Examiner—Jeanine Goldberg
(74) Attorney, Agent, or Firm—Wolf Greenfield & Sacks, P.C.

(57) ABSTRACT

The invention relates to the identification of a novel gene, TMS1, which is transcriptionally silenced as a result of methylation. Nucleic acids and polypeptides are provided as are methods and tools for diagnosing and treating disorders characterized by such methylation, and/or abnormally low levels of TMS1 expression products.

17 Claims, 17 Drawing Sheets

OTHER PUBLICATIONS

Magdinier, et al., "Down–regulation of BRCA1 in human sporadic breast cancer; analysis of DNA methylation patterns of the putative promoter region", *Oncogene*, 17(24):3169–76 (1998) *ABSTRACT*.

Lapidus, et al, "Methylation of estrogen and progesterone receptor gene 5' CpG islands correlates with lack of estrogen and progesterone receptor gene expression in breast tumors", *Clin. Cancer. Res.*, 2(5):805–10 (1996) *ABSTRACT*.

Rice, et al., "Aberrant methylation of the BCRA1 CpG island promoter is associated with decreased BRCA1 mRNA in sporadic breast cancer cells" *Oncogene*, 17(14):1807–12 (1998) *ABSTRACT*.

Huschtscha, et al., "Loss of p16INK4 expression by methylation is associated with lifespan extension of human mammary epithelial cells", *Cancer Res.*, 58(16):3508–12 (1998) *ABSTRACT*.

Jhaveri, et al., "Methylation–mediated regulation of the glutathione S–transferase P1 gene in human breast cancer cells", *Gene*, 210(1):1–7 (1998) *ABSTRACT*.

Fujii, et al., "Methylation of the HIC–1 candidate tumor suppresor gene in human breast cancer", *Oncogene*, 16(16):2159–64 (1998) *ABSTRACT*.

Foster, et al., "Inactivation of p16 in human mammary epithelial cells by CpG island methylation", *Mol. Cell. Biol.*, 18(4):1793–801 (1998) *ABSTRACT*.

Wicki, et al., "Repression of the candidate tumor suppressor genes S100A2 in breast cancer is mediated by site–specific hypermethylation", *Cell Calcium*, 22(4):243–54 (1997) *ABSTRACT*.

Dobrovic, et al., "Methylation of the BRCA1 gene is sporadic breast cancer", *Cancer Res.*, 57(16):3347–50 (1997) *ABSTRACT*.

Huynh, et al., "Silencing of the mammary–derived growth inhibitor (MDGI) gene in breast neoplasms is associated with epigenetic changes", *Cancer Res.*, 56(21):4865–70 (1996) *ABSTRACT*.

Herman, et al., "Hypermethylation–associated inactivation indicates a tumor suppressor role for p15INK4B", *Cancer Res.*, 56(4):722–7 (1996) *ABSTRACT*.

Herman, et al., "Inactivation of the CDKN2/p16/MTS1 gene is frequently associated with aberrant DNA methylation in all common human cancers", *Cancer Res.*, 55(20):4525–30 (1995) *ABSTRACT*.

Ottaviano, et al., "Methylation of the estrogen receptor gene CpG island marks loss of estrogen receptor expression in human breast cancer cells", *Cancer Res.*, 54(10):2552–5 (1994) *ABSTRACT*.

MacConnell, et al., "TMS1, a novel apoptosis–inducing protein that is silenced by methylation in breast cancer cells" Proceedings of the American Association For Cancer Research, Mar. 2000, vol. 41, p. 464, 91st Annual Meeting of the American Association for Cancer Research; San Francisco, CA, USA; Apr. 1–5, 2000.

Vertino, et al., "Identification of novel targets of methylation–mediated gene silencing: Loss of apoptotic signalling by aberrant methylation" Proceedings of the American Association For Cancer Research, Mar. 2000, vol. 41, p. 896, 91st Annual Meeting of the American Association for Cancer Research; San Francisco, CA, USA; Apr. 1–5, 2000 Abstract S37.

MacConnell, et al., "Activation of a caspase–9–mediated apoptotic pathway by subcellular redistribution of the novel caspase recruitment domain protein TMS1" Cancer Res. 2000, vol. 60, No. 22, pp. 6243–6247.

Levine, et al., "High–resolution methylation mapping of the TMS1 locus in human breast cancer cell lines and primary tumors" Proceedings of the American Association For Cancer Research., Mar. 2001, vol. 42, pp. 708–709, 92nd Annual Meeting of the American Association for Cancer Research; New Orleans, LA, USA; Mar. 24–28, 2001 Abstract 3808.

Written Opinion from International Application No. PCT/US00/28747 (E0355.70003WO), Mar. 18, 2002.*

International Preliminary Examination Report from International Application No. PCT US00/28747 (E0355.70003WO), Jul. 4, 2002.*

* cited by examiner

Fig. 5B

TMS1 COMPOSITIONS AND METHODS OF USE

RELATED APPLICATIONS

This application claims priority to U.S. Provisional Patent Application filed Oct. 18, 1999, entitled "TMS1 COMPOSITIONS AND METHODS OF USE", Ser. No. 60/159,975, the contents of which are incorporated by reference herein in their entirety.

GOVERNMENT SUPPORT

This invention was made in part with government support under grant number CA77337 from the National Institutes of Health. The Government may retain certain rights in the invention.

FIELD OF THE INVENTION

This invention relates to nucleic acid molecules and polypeptides of TMS1, a novel apoptotic regulatory gene silenced as a result of abnormal methylation, and their use in diagnosis and treatment regimens.

BACKGROUND OF THE INVENTION

Methylation of bases in DNA serves a number of cellular functions. In bacteria, methylation of cytosine and adenine residues plays a role in the regulation of DNA replication and DNA repair. DNA methylation also constitutes part of a immune mechanism that allows these organisms to distinguish between self and non-self DNA. In mammalian species, DNA methylation occurs only at cytosine residues, and specifically at cytosine residues that lie next to a guanosine residue, i.e., within the sequence CG. Methylation of DNA is carried out by methyltransferases (sometimes called methylases). Generally both DNA strands can accept methyl groups at opposing CG sites. Replication of these strands yields a hemi-methylated state which is recognized by a class of maintenance methyltransferases capable of restoring full methylation to both strands. Most CG sites in the genome are methylated except for those in CpG 'islands' which remain methylation-free. CpG 'islands' are rich in CG sites and are often found near coding regions within the genome (i.e., genes). About half of the genes in the human genome are associated with CpG islands. Importantly, the vast majority of CpG islands in the genome remain unmethylated in normal adult cells and tissues. Methylation of CpG islands is normally seen only on the inactive X-chromosome in females and at imprinted genes where it functions in the stable silencing of such genes. Strict control over the levels and distribution of DNA methylation are essential to normal animal development.

Alterations in DNA methylation are one manifestation of the genome instability characteristic of human tumors. A hallmark of human carcinogenesis is the loss of normal constraints on cell growth resulting from genetic alterations in the genes that control cell growth. The consequences of such mutations include the activation of positive growth signals and the inactivation of growth inhibitory signals. Gene function can be lost through mutation or deletion. An alternative mechanism by which gene function can be lost is aberrant DNA methylation. Accordingly, such methylation events can be viewed as key steps in both the initiation and progression of neoplastic disease.

Identification of gene targets which when methylated lead to the loss of normal cell responses, as well as identification of agents which desirably prevent or at least control such methylation events would be valuable. Such gene targets and agents will facilitate the diagnosis and treatment of disorders associated with abnormal methylation and any downstream events resulting therefrom.

SUMMARY OF THE INVENTION

The invention relates to the diagnosis and treatment, both prophylactically and therapeutically, of disorders characterized by abnormal expression profiles of TMS1. Abnormal expression profiles of TMS1 include decreased or absent expression of wild-type TMS1 mRNA and/or polypeptides, as well as expression of mutant TMS1 mRNA or polypeptides. The net result of such abnormal TMS1 expression profiles is a reduction in TMS1 activity, which can be accomplished by, among other things, reduced transcription from the TMS1 genomic locus, reduced translation of TMS1 mRNA, reduced production of functional TMS1 polypeptides, and increased production of mutant, including dominant negative, forms of TMS1 polypeptides. In some preferred aspects, the invention is directed at diagnosing and treating disorders characterized by abnormally low levels of TMS1 expression products, such as TMS1 mRNA and polypeptides. One preferred subset of such disorders intended for treatment are those characterized by abnormal methylation of the TMS1 genomic locus (i.e., a CpG island containing TMS1 nucleic acid molecule).

The invention involves, in one aspect, the molecular cloning and characterization of TMS1, a novel polypeptide believed important for normal cell growth. Although not intending to be bound by any particular theory, it is proposed that TMS1 polypeptides exert their normal effects by inducing apoptosis in cells, when and where appropriate. It has been discovered that malignant cells manifest increased methylation of TMS1 genomic DNA sequences and corresponding decreased expression of TMS1 mRNA and polypeptides relative to normal counterparts. It follows that in order for a malignant cell to ensure survival and propagation, inactivation of a cell death mediator, such as TMS1, may be required. In this regard, TMS1 may be considered a tumor-suppressor, since it may be normally involved in the negative selection of pre-malignant and malignant cells in vivo.

The invention provides isolated nucleic acid molecules, unique fragments of those molecules, expression vectors containing the foregoing, and host cells transfected with those molecules. The invention also provides agents which bind TMS1 polypeptides, including antibodies. The foregoing can be used in the diagnosis or treatment of conditions characterized by a decreased expression level and/or an absence of TMS1 mRNA or polypeptides. One particularly important subset of disorders is those in which the decreased levels of TMS1 expression products result from an abnormal methylation of the CpG island in the TMS1 genomic locus. The invention also provides methods for identifying pharmacological agents useful in the diagnosis or treatment of such conditions.

According to one aspect of the invention, isolated nucleic acid molecules that code for a native polypeptide are provided and include: (a) nucleic acid molecules which hybridize under stringent conditions to a complement of a molecule consisting of a nucleotide sequence selected from the group consisting of SEQ ID NO:1, SEQ ID NO:2, SEQ ID NO:5, SEQ ID NO:7, SEQ ID NO:9, SEQ ID NO:20, SEQ ID NO:22 and SEQ ID NO:24, and which code for a native polypeptide, (b) deletions, additions and substitutions of (a) which code for an apoptosis-inducing polypeptide, (c)

nucleic acid molecules that differ from the nucleic acid molecules of (a) or (b) in codon sequence due to the degeneracy of the genetic code, and (d) complements of (a), (b) or (c). In certain embodiments, the isolated nucleic acid hybridizes to a complement of a molecule consisting of a nucleotide sequence selected from the group consisting of SEQ ID NO:1, SEQ ID NO:2, and SEQ ID NO:24. In other embodiments, the isolated nucleic acid hybridizes to a complement of a molecule consisting of a nucleotide sequence selected from the group consisting of SEQ ID NO:20, SEQ ID NO:22. In yet further embodiments, the isolated nucleic acid hybridizes to a complement of a molecule consisting of a nucleotide sequence selected from the group consisting of SEQ ID NO:5, SEQ ID NO:7 and SEQ ID NO:9. In certain embodiments, the isolated nucleic acid molecule comprises a nucleotide sequence selected from the group consisting of SEQ ID NO:2, SEQ ID NO:20, SEQ ID NO:22 and SEQ ID NO:24. In other embodiments, the isolated nucleic acid molecule comprises a nucleotide sequence selected from the group consisting of SEQ ID NO:5, SEQ ID NO:7 and SEQ ID NO:9. In still other embodiments, the isolated nucleic acid molecule comprises a nucleotide sequence of SEQ ID NO:26.

In some embodiments the isolated nucleic acid molecules are those which code for a polypeptide having an amino acid sequence selected from the group consisting of SEQ ID NO:3, SEQ ID NO:21, SEQ ID NO:23 and SEQ ID NO:25. In an important embodiment, the native polypeptide is a native TMS1 polypeptide. A native TMS1 polypeptide is one which possesses a native TMS1 function or activity, such as apoptosis induction. Sequence homology has revealed that TMS1 contains a caspase recruiting domain (i.e., a CARD). Thus, another function of a native TMS1 polypeptide is the ability to bind to either itself or to other CARD containing proteins, specifically through the CARD.

The invention in another aspect provides an isolated nucleic acid molecule selected from the group consisting of (a) a unique fragment of nucleic acid molecule of SEQ ID NO:1, of sufficient length to represent a sequence unique within the human genome, and (b) complements of (a), provided that the fragment includes a sequence of contiguous nucleotides which is not identical to a sequence selected from the sequence group consisting of (1) sequences having the GenBank and EMBL accession numbers of Table I, and having been published prior to the priority date or filing date, and (2) complements of (1).

In one embodiment, the sequence of contiguous nucleotides is selected from the group consisting of (1) at least two contiguous nucleotides nonidentical to the sequence group, (2) at least three contiguous nucleotides nonidentical to the sequence group, (3) at least four contiguous nucleotides nonidentical to the sequence group, (4) at least six contiguous nucleotides nonidentical to the sequence group, (5) at least eight contiguous nucleotides nonidentical to the sequence group, (6) at least ten contiguous nucleotides nonidentical to the sequence group.

In another embodiment, the unique fragment has a size selected from the group consisting of at least: 8 nucleotides, 10 nucleotides, 12 nucleotides, 14 nucleotides, 16 nucleotides, 18 nucleotides, 20 nucleotides, 22 nucleotides, 24 nucleotides, 26 nucleotides, 28 nucleotides, 30 nucleotides, 40 nucleotides, 50 nucleotides, 75 nucleotides, 100 nucleotides, 200 nucleotides, 1000 nucleotides and every integer length therebetween as if fully recited herein.

In other embodiments, the unique fragment encodes a peptide which is a fragment of a polypeptide consisting of an amino acid sequence selected from the group consisting of SEQ ID NO:3 and SEQ ID NO:25.

According to another aspect, the invention provides expression vectors, and host cells transformed or transfected with such expression vectors, comprising the nucleic acid molecules described above.

In yet another aspect, the invention provides an isolated nucleic acid molecule comprising the nucleotide sequence of SEQ ID NO:4. SEQ ID NO:4 represents the nucleotide sequence of nucleotides 1100–1725 of SEQ ID NO:1, corresponding to a CpG island in the TMS1 genomic sequence. Also provided is an expression vector comprising the isolated nucleic acid molecule comprising a nucleotide sequence of SEQ ID NO:4, or a regulatory fragment thereof, operably linked to a reporter coding sequence. In one embodiment, the reporter coding sequence comprises a promoter.

In yet another embodiment, other regulatory sequences of TMS1 are provided including those of introns 1 and 2 in SEQ ID NO:1. Intron 1 in SEQ ID NO:1 corresponds to nucleotides 1530–1742 and intron 2 in SEQ ID NO:2 corresponds to nucleotides 1800–2104.

According to another aspect of the invention, an isolated polypeptide is provided. The isolated polypeptide is encoded by the foregoing isolated nucleic acid molecules of the invention. Preferably the isolated polypeptide is a native TMS1 polypeptide. In important embodiments, the isolated polypeptide consists of an amino acid sequence selected from the group consisting of SEQ ID NO:3, SEQ ID NO:21, SEQ ID NO:23 and SEQ ID NO:25. In other embodiments, an isolated peptide is provided which comprises a fragment or variant of a polypeptide (such as one consisting of an amino acid sequence of SEQ ID NO:3 or SEQ ID NO:25) of sufficient length to represent a sequence unique within the human genome, and to identify a native TMS1 polypeptide. The isolated peptide may comprise at least 6, at least 8, at least 9, at least 10, at least 11, at least 12, at least 14, at least 18 or at least 20 contiguous amino acids having a sequence of a fragment of SEQ ID NO:3 or SEQ ID NO:25. Isolated peptides which are immunogenic are also provided.

According to another aspect of the invention, compositions are provided which comprise an isolated agent that binds selectively to a native TMS1 polypeptide encoded by the foregoing isolated nucleic acid molecules of the invention. Preferably, the isolated agent binds selectively to a polypeptide comprising an amino acid sequence selected from the group consisting of SEQ ID NO:3, SEQ ID NO:21, SEQ ID NO:23 and SEQ ID NO:25, or a fragment thereof. The isolated agent may selectively bind to a polypeptide comprising an amino acid sequence of SEQ ID NO:21 or SEQ ID NO:23 or SEQ ID NO:25. In important embodiments, the isolated agent is a peptide. In a further embodiment, the peptide is an antibody or a fragment thereof (e.g., Fab, F(ab)$_2$, Fd and antibody fragments which include a CDR3 region which binds selectively to the native TMS1 polypeptide). In even more preferred embodiments, the antibody is a humanized antibody or a chimeric antibody. The isolated agent may be conjugated to a detectable label. The detectable label may be selected from the group consisting of a radioactive label, an enzyme, a biotin molecule, an avidin molecule or a fluorochrome.

According to another aspect of the invention, a method is provided for identifying a subject at risk of developing a disorder characterized by abnormal methylation of a CpG island containing TMS1 nucleic acid molecule. The method involves determining a level of methylation of a CpG island containing TMS1 nucleic acid molecule in a biological sample from a subject, and comparing the level of methylation of the CpG island containing TMS1 nucleic acid molecule in the biological sample to a control. The CpG island containing TMS1 nucleic acid molecule is selected from the group consisting of (a) nucleic acid molecules which hybridize under stringent conditions to a complement of a molecule consisting of SEQ ID NO:4 and which code for a native TMS1 polypeptide, and (b) complements of (a). According to the method provided, an increase in the level of methylation of the CpG island containing TMS1 nucleic acid molecule in the biological sample compared to the control identifies a subject at risk of developing the disorder. The disorder may be a tumor. In one embodiment, the level of methylation is determined using a technique selected from the group consisting of methylation-sensitive restriction analysis, methylation specific polymerase chain reaction (MSP), sequencing of bisulfite-modified DNA, methylation-sensitive single nucleotide primer extension (Ms-SNuPE), and combined bisulfite restriction analysis (COBRA).

The biological sample may be selected from the group consisting of breast tissue, ovarian tissue, prostatic tissue, cervical tissue, peripheral blood and bone marrow. In a preferred embodiment, the biological sample is breast tissue. In important embodiments, the control comprises a normal tissue from a normal subject, or normal appearing tissue adjacent to a tumor.

In another aspect, the invention provides a method for determining a risk of developing a disorder characterized by abnormal methylation of a CpG island containing TMS1 nucleic acid molecule. The method in this latter aspect involves measuring a level of an expression product of a CpG island containing TMS1 nucleic acid molecule, by contacting a biological sample isolated from a subject with an agent that selectively binds to a target expression product, determining a level of interaction between the agent and the target expression product, and comparing the level of interaction between the agent and the target expression product with a control. The target expression product is selected from the group consisting of (a) nucleic acid expression products which hybridize under stringent conditions to a complement of a molecule comprising a nucleotide sequence selected from the group consisting of SEQ ID NO:2 and SEQ ID NO:24 and which code for a native TMS1 polypeptide, and (b) polypeptide expression products, and fragments thereof, of (a).

In preferred embodiments, the control comprises a normal tissue from a normal subject. In important embodiments, a decrease in the level of interaction between the agent and the target expression molecule in the biological sample compared to the control indicates a risk of developing the disorder. In one embodiment, the disorder is a proliferative disorder. In a preferred embodiment, the disorder is cancer. In an even more preferred embodiment, the cancer is breast cancer. The agent, in one embodiment, is a nucleic acid molecule. In another embodiment, the agent is a peptide. In still a further embodiment, the peptide is an antibody or a fragment thereof. In the foregoing embodiments, various methods can be used to measure expression, including Northern analysis, reverse-transcriptase polymerase chain reaction (RT-PCR), immunohistochemistry and Western analysis.

The invention in yet another aspect provides a method for treating a subject having, or at risk of developing, a disorder characterized by abnormal methylation of a CpG island containing TMS1 nucleic acid molecule. In another related aspect, a method is provided for treating a subject having, or at risk of developing, a disorder, perhaps in a tissue, characterized by abnormally low levels of a TMS1 expression product. Both methods comprise administering a demethylating agent to a subject in need of such treatment in an amount effective. The effective amount is dependent upon the subject to be treated. If the subject is at risk of developing the disorder, then preferably the demethylating agent is administered in an amount effective to maintain a normal level of methylation in a CpG island containing TMS1 nucleic acid molecule in a tissue of the subject. If, on the other hand, the subject has the disorder, then preferably the demethylating agent is administered in an amount effective to reduce the level of methylation in a CpG island containing TMS1 nucleic acid molecule in a tissue of the subject. In an important embodiment, the level of methylation in the CpG island containing TMS1 nucleic acid molecule is reduced compared to a pre-treatment level of methylation.

In one embodiment, the method further comprises first selecting a subject in need of such treatment. In certain embodiments, the disorder is cancer. In important embodiments, the cancer is breast cancer. In one embodiment of the preceding aspect, the method further comprises administering a disorder-specific therapy to a subject so identified as at risk of developing the disorder. In embodiments in which the disorder is a cancer, the subject is administered an anti-cancer therapy. In one embodiment, the anti-cancer therapy is administered once the level of methylation in a CpG island containing TMS1 nucleic acid molecule in a tissue of the subject is reduced.

The CpG island containing TMS1 nucleic acid molecule is selected from the group consisting of (a) nucleic acid molecules which hybridize under stringent conditions to a complement of a molecule comprising SEQ ID NO:4, and which code for a native TMS1 polypeptide, and (b) complements of (a).

In some embodiments of the foregoing, the demethylating agent is administered to a tissue at risk of developing a tumor. Preferably the demethylating agent is administered locally within a subject in the area of the tissue. The demethylating agent may be an inhibitor of methyltransferase. In preferred embodiments, the inhibitor of methyltransferase is selected from the group consisting of 5-azacytidine, 5-aza-2'deoxycytidine (also known as Decitabine in Europe), 5,6-dihydro-5-azacytidine, 5,6-dihydro-5-aza-2'deoxycytidine, 5-fluorocytidine, 5-fluoro-2'deoxycytidine, and short oligonucleotides containing 5-aza-2'deoxycytosine, 5,6-dihydro-5-aza-2'deoxycytosine, and 5-fluoro-2'deoxycytosine. The demethylating agent may be conjugated to, or more preferably incorporated into, a nucleic acid molecule. The nucleic acid molecule may be selected from the group consisting of (a) nucleic acid molecules which hybridize under stringent conditions to a complement of a molecule comprising SEQ ID NO:1, and (b) complements of (a). Alternatively, the sequence may be unrelated to SEQ ID NO:1 or complements thereof.

In another aspect, the invention provides another method for treating a subject having, or at risk of developing, a disorder characterized by abnormal methylation of a CpG island containing TMS1 nucleic acid molecule. In a related aspect, another method is provided for treating a subject having, or at risk of having, a disorder characterized by abnormally low levels of a TMS1 expression product. When used therapeutically in subjects having the disorder, the methods involve administering a CARD containing molecule to a subject in need of such treatment in an amount effective to increase CARD polypeptide level in a tissue of the subject. When used prophylactically in subjects at risk of developing the disorder, the methods involve administering a CARD containing molecule to a subject in need of such treatment, preferably in an amount effective to establish or maintain a normal level of CARD polypeptide in a tissue of the subject. The method may further comprise first selecting a subject having or at risk of developing the disorder. In important embodiments, the disorder is cancer. According to one embodiment, the cancer is breast cancer. In important embodiments, the level of the CARD polypeptide is increased relative to a pre-treatment level.

In one embodiment, the CARD containing molecule is selected from the group consisting of a CARD containing nucleic acid molecule and CARD containing polypeptide. In an important embodiment, the CARD containing molecule is a TMS1 molecule. The TMS1 molecule may be selected from the group consisting of a TMS1 nucleic acid molecule or a TMS1 polypeptide. In one embodiment, the CARD containing nucleic acid molecule comprises an nucleotide sequence selected from the group consisting of SEQ ID NO:1, SEQ ID NO:2, SEQ ID NO:9, SEQ ID NO:20, SEQ ID NO:22 and SEQ ID NO:24. In another embodiment, the CARD containing polypeptide comprises an amino acid sequence selected from the group consisting of SEQ ID NO:3, SEQ ID NO:10, SEQ ID NO:21, SEQ ID NO:23 and SEQ ID NO:25, and is preferably selected from the group consisting of SEQ ID NO:3, SEQ ID NO:21, SEQ ID NO:23 and SEQ ID NO:25. In one embodiment, the CARD containing molecule is administered to a tissue having, or at risk of developing, the disorder (e.g., a tumor). In one embodiment, the disorder is cancer. The cancer may be breast cancer, but is not so limited.

The invention in another aspect involves a method for increasing TMS1 expression in a subject that fails to express a normal level of wild-type TMS1 or expresses a mutant TMS1. An isolated TMS1 nucleic acid molecule of the invention or an expression product thereof, including mRNA and/or polypeptide, is administered to such a subject, in an amount effective to increase wild-type TMS1 expression in the subject.

In other aspects, the invention provides a method for determining the risk of a subject being non-responsive to a disorder-specific therapy and a method for identifying a subject who is at risk of being non-responsive to disorder-specific therapy. In important embodiments of the immediately foregoing methods, the subject has cancer, and the disorder-specific therapy is an anti-cancer therapy or an anti-proliferative therapy. The methods involve determining a level of methylation of a CpG island containing TMS1 nucleic acid molecule in a biological sample from a subject having a disorder (e.g., cancer), and comparing the level of methylation of the CpG island containing TMS1 nucleic acid molecule in the biological sample to a control. The CpG island containing TMS1 nucleic acid molecule is as described herein according to other aspects of the invention. According to the method, an increase in the level of methylation of the CpG island containing TMS1 nucleic acid molecule in the biological sample compared to the control identifies a subject who is at risk of being non-responsive to the disorder-specific therapy (e.g., anti-cancer therapy). The level of methylation is determined using techniques such as those listed above for other aspects of the invention.

In related aspects, methods are provided for determining the risk of a subject being non-responsive to a disorder-specific therapy and identifying a subject who is at risk of being non-responsive to a disorder-specific therapy by measuring a level of an expression product of a CpG island containing TMS1 nucleic acid molecule in a tissue in a subject. Preferably, the subject has the disorder and the disorder exists in the tissue being tested. The methods involve contacting a biological sample isolated from a subject with an agent that selectively binds to a target expression product, determining a level of interaction between the agent and the target expression product, and comparing the level of interaction between the agent and the target expression product with a control. The target expression product can be selected from the group consisting of (a) nucleic acid expression products which hybridize under stringent conditions to a complement of a molecule comprising SEQ ID NO:2 and which code for a native TMS1 polypeptide, and (b) polypeptide expression products, and fragments of (a) or (b).

In preferred embodiments, the control comprises a normal tissue from a normal subject. In a related embodiment, the control is normal tissue from the subject having cancer. In important embodiments, a decrease in the level of interaction between the agent and the target expression molecule in the biological sample compared to the control indicates a risk of developing the disorder. In one embodiment, the disorder is a proliferative disorder. In a preferred embodiment, the disorder is cancer. The cancer may be breast cancer, but is not so limited. In one embodiment, the biological sample is a breast cancer tumor. The agent, in one embodiment, is a nucleic acid molecule. In another embodiment, the agent is a peptide. In still a further embodiment, the peptide is an antibody or a fragment thereof. In the foregoing embodiments, various methods can be used to measure expression, including Northern analysis, reverse-transcriptase polymerase chain reaction (RT-PCR), immunohistochemistry, and Western analysis.

The disorder-specific therapy may be anti-cancer therapy. In some embodiments, it is a DNA-damaging anti-cancer therapy. A DNA damaging anti-cancer therapy is a therapy that is effective due to its ability to induce DNA damage and, thus ultimately, lead to the death of the cell via apoptosis. In one embodiment, the DNA damaging anti-cancer therapy is radiation therapy or some form of chemotherapy. The method may further comprise administering to the subject an anti-cancer therapy which is not dependent upon DNA damage or alternatively an anti-cancer therapy which is not dependent upon apoptosis. In important embodiments, the subject is administered an anti-cancer therapy selected from the group consisting of biological response modifying therapy, immunotherapy, cancer vaccine therapy, hormone therapy and angiogenesis inhibiting therapy.

The method may further comprise administering to the subject at risk of being non-responsive to an anti-cancer therapy, a demethylating agent and an anti-cancer therapy. Alternatively, the method may further comprise administering to the subject at risk of being non-responsive to an anti-cancer therapy, a TMS1 molecule selected from the group consisting of a TMS1 nucleic acid molecule and a TMS1 polypeptide, and an anti-cancer therapy. In one embodiment, the preferred TMS1 nucleic acid molecule comprises an nucleotide sequence selected from the group consisting of SEQ ID NO:1, SEQ ID NO:2, SEQ ID NO:20, SEQ ID NO:22 and SEQ ID NO:24. In another embodiment, the preferred TMS1 polypeptide comprises an amino acid sequence selected from the group consisting of SEQ ID NO:3, SEQ ID NO:21, SEQ ID NO:23 and SEQ ID NO:25.

The invention further provides, in yet another aspect, a method for treating a subject having a cancer comprising administering a demethylating agent and an anti-cancer therapy to a subject in need of such treatment in an amount effective to treat the cancer. In a related aspect, the invention provides another method for treating a subject having a cancer comprising administering a TMS1 molecule and an anti-cancer therapy to a subject in need of such treatment in an amount effective to treat the cancer. The cancer may be one which is characterized by abnormal methylation of a CpG island containing TMS1 nucleic acid molecule (as described for preceding aspects). Alternatively, the cancer may be characterized by an abnormally low levels of a TMS1 expression product. In yet another embodiment, the disorder may be characterized by the presence of a mutant TMS1 molecule, in which case, treatment with a TMS1 molecule alone or with an anti-cancer therapy may be suitable. The demethylating agent or the TMS1 molecule may be administered prior to, or concurrently with, the anti-cancer therapy.

In one embodiment, the TMS1 molecule is selected from the group consisting of a TMS1 nucleic acid molecule and a TMS1 polypeptide. In another embodiment, the preferred TMS1 nucleic acid molecule comprises an nucleotide sequence selected from the group consisting of SEQ ID NO:1, SEQ ID NO:2, SEQ ID NO:20, SEQ ID NO:22 and SEQ ID NO:24. The preferred TMS1 polypeptide comprises an amino acid sequence selected from the group consisting of SEQ ID NO:3 and SEQ ID NO:25, while in other embodiments, the amino acid sequence may be SEQ ID NO:10, SEQ ID NO:21 or SEQ ID NO:23.

In related aspects, the demethylating agent or the TMS1 molecule may be administered to the subject in an amount effective to sensitize the cancer to the anti-cancer therapy (e.g., an amount of demethylating agent or TMS1 molecule effective to make the cancer responsive to the anti-cancer therapy, or to decrease the dose of anti-cancer therapy required to treat the cancer).

In yet a further aspect, the invention provides a method for treating a subject having a disorder characterized by abnormal cell proliferation. In a preferred embodiment, the abnormal cell proliferation is a cancer. The method involves administering a TMS1 molecule to a tissue having the disorder in an amount effective to increase the level of TMS1 polypeptide to an above-normal level. The above-normal level may be at least 10%, at least 20%, at least 30%, at least 50%, at least 100% or at least 150% above normal levels. Preferably, the level of TMS1 polypeptide is one which induces the apoptosis of the cells in which it is expressed. The disorder may or may not be one characterized by abnormal methylation of a CpG island containing TMS1 nucleic acid molecule or by an abnormally low level of a TMS1 expression product. In one embodiment, the disorder is breast cancer.

The invention further provides a method for identifying other nucleic acid molecules that are silenced as a result of methylation and which may be involved in cancer. Thus, in another aspect of the invention, a method is provided for identifying a nucleic acid molecule transcriptionally down-regulated following methylation. The method comprises overexpressing a methyltransferase molecule in an experimental cell, and identifying a differentially expressed molecule which has a lower level of expression in the experimental cell than in a control. In a preferred embodiment, the methyltransferase is a human DNA methyltransferase. In important embodiments, the experimental cell is one which overexpresses a DNA methyltransferase. The cell may be a primary cell or a cell from an established cell line. In a preferred embodiment, the experimental cell is HMT.1E1. The control may be an immortalized fibroblast cell line. In a preferred embodiment, the control is an SV40 immortalized variant of the IMR90 fibroblast cell line. In one embodiment, the expression product is an mRNA. The differentially expressed molecule may be identified using a technique selected, for example, from the group consisting of subtractive hybridization, differential display, representational difference analysis and cDNA microarray analysis.

The invention also provides screening assays for identifying binding partners (e.g., ligands) of TMS1. The binding partners may be naturally occurring (e.g., natural ligands of TMS1) or they may be synthetic. Additionally, they may be activating (i.e., capable of promoting apoptosis in the context of TMS1) or inhibiting (i.e., capable of interfering with apoptosis in the context of TMS1).

In one aspect, the invention provides a method for identifying a TMS1 polypeptide binding partner comprising obtaining a binding assay result from a binding assay between a library member and a TMS1 polypeptide, and comparing the binding assay result to a control binding assay result. According to one method, a binding assay result that is greater than a control binding assay result indicates that the library member is a TMS1 polypeptide binding partner. In one embodiment, the preferred TMS1 polypeptide comprises an amino acid sequence selected from the group consisting of SEQ ID NO:3, SEQ ID NO:21, SEQ ID NO:23 and SEQ ID NO:25. In one embodiment, the library member is derived from a natural source library.

In a related aspect, the invention provides a method for identifying a TMS1 N-terminal polypeptide binding partner comprising obtaining a binding assay result from a binding assay between a library member and a TMS1 N-terminal polypeptide, and comparing the binding assay result to a control binding assay result. According to one method, a binding assay result that is greater than a control binding assay result indicates that the library member is a TMS1 N-terminal polypeptide binding partner. The TMS1 N-terminal polypeptide may comprise an amino acid sequence selected from the group consisting of SEQ ID NO:6, SEQ ID NO:8 and SEQ ID NO:27, but it is not so limited. In another embodiment, the TMS1 N-terminal polypeptide comprises an amino acid sequence selected from the group consisting of SEQ ID NO:3, SEQ ID NO:21, SEQ ID NO:23 and SEQ ID NO:25, and the control binding assay result is obtained from a control binding assay between a library member and a polypeptide consisting of an amino acid sequence of SEQ ID NO:10. In one embodiment, the library member is derived from a natural source library.

Another aspect of the invention provides compositions comprising any of the foregoing isolated nucleic acid molecules of the invention, or expression products thereof, in amounts effective to increase levels of wild-type TMS1 expression products, and a pharmaceutically acceptable carrier.

The invention also contemplates kits comprising a package including assays for TMS1 epitopes, TMS1 nucleic acids or TMS1 methylation. The kit further comprises instructions and optionally related materials such as controls, for example, a number, color chart, or an epitope of the expression product of the foregoing isolated nucleic acid molecules of the invention, for comparing the level of wild-type and/or mutant TMS1 polypeptides, wild-type or mutant TMS1 nucleic acid forms or the level of TMS1 methylation in a test sample to the level in the control. This comparison can be used to assess a risk of developing a disorder characterized by abnormally low levels of wild-type TMS1 expression products or a risk of developing a disorder characterized by abnormal methylation of CpG island containing TMS1 nucleic acid molecules.

Thus, the present invention thus involves, in several aspects, TMS1 polypeptides, genes encoding such polypeptides, functional modifications and variants of the foregoing, useful fragments of the foregoing, as well as therapeutics and diagnostics relating thereto. These and other objects of the invention will be described in further detail in connection with the detailed description of the invention.

BRIEF DESCRIPTION OF THE FIGURES

FIG. 5B illustrates the amino acid alignment of TMS1 with the CARD motif of other apoptotic signaling proteins. Numbers in parentheses indicate the position in the amino acid sequence. Reverse type indicate ≧50% amino acid identity; gray shading indicates ≧50% similarity through conserved amino acid substitutions.

BRIEF DESCRIPTION OF THE SEQUENCE LISTING

Figure 1A:
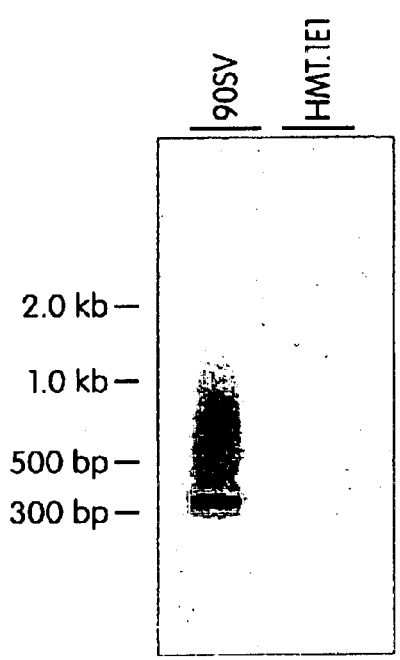
FIG. 1A is a representation of a Southern blot analysis of cell lines 90SV and HMT.1E1. Hybridization shows clone RDA-2.15 is differentially represented in cDNA derived from 90SV and HMT.1E1 cells

SEQ ID NO:1 is the nucleotide sequence of human TMS1 genomic DNA (Accession No. AF184072).

SEQ ID NO:2 is the nucleotide sequence of human TMS1 cDNA (Accession No. AF184073).

SEQ ID NO:3 is the amino acid sequence of human TMS1 polypeptide.

SEQ ID NO:4 is the nucleotide sequence of nucleotides 1100–1725 of SEQ ID NO:1, corresponding to the TMS1 CpG island.

SEQ ID NO:5 is the nucleotide sequence of nucleotides 1190–1529 of SEQ ID NO:1, corresponding to TMS1 exon 1.

SEQ ID NO:6 is the amino acid sequence encoded by nucleotides 1190–1529 of SEQ ID NO:1, corresponding to TMS1 exon 1.

SEQ ID NO:7 is the nucleotide sequence of nucleotides 1743–1799 of SEQ ID NO:1, corresponding to TMS1 exon 2.

SEQ ID NO:8 is the amino acid sequence encoded by nucleotides 1743–1799 of SEQ ID NO:1, corresponding to TMS1 exon 2.

SEQ ID NO:9 is the nucleotide sequence of nucleotides 2105–2460 of SEQ ID NO:1, corresponding to TMS1 exon 3.

SEQ ID NO:10 is the amino acid sequence encoded by nucleotides 2105–2460 of SEQ ID NO:1, corresponding to TMS1 exon 3.

SEQ ID NO:11 is the nucleotide sequence of a TMS1 specific forward primer.

SEQ ID NO:12 is the nucleotide sequence of a TMS1 specific reverse primer.

SEQ ID NO:13 is the nucleotide sequence of a TMS1 specific forward RT-PCR primer.

SEQ ID NO:14 is the nucleotide sequence of a β-actin specific forward RT-PCR primer.

SEQ ID NO:15 is the nucleotide sequence of a β-actin specific reverse RT-PCR primer.

SEQ ID NO:16 is the nucleotide sequence of a unmethylated TMS1 specific forward primer.

SEQ ID NO:17 is the nucleotide sequence of a unmethylated TMS1 specific reverse primer.

SEQ ID NO:18 is the nucleotide sequence of a methylated TMS1 specific forward primer.

SEQ ID NO:19 is the nucleotide sequence of a methylated TMS1 specific reverse primer.

SEQ ID NO:20 is the nucleotide sequence of mouse TMS1 cDNA.

SEQ ID NO:21 is the amino acid sequence of mouse TMS1 polypeptide.

SEQ ID NO:22 is the partial nucleotide sequence of rat TMS1 cDNA.

SEQ ID NO:23 is the partial amino acid sequence of rat TMS1 polypeptide.

SEQ ID NO:24 is the nucleotide sequence of an alternatively spliced form of human TMS1 cDNA (Accession No. AF255794) which is missing exon 2.

SEQ ID NO:25 is the amino acid sequence of an alternatively spliced form of human TMS1 polypeptide which is missing exon 2.

SEQ ID NO:26 is the nucleotide sequence of an alternatively spliced form of TMS1 cDNA which is missing exon 3.

SEQ ID NO:27 is the amino acid sequence of an alternatively spliced form of TMS1 cDNA which is missing exon 3.

DETAILED DESCRIPTION OF THE INVENTION

Cancers arise from any number of cellular perturbations in a cell. Most of these perturbations take the form of a genetic mutation at the genomic DNA level. Genetic mutations can in turn manifest their effects in a number of ways including alterations in expression levels and/or function of an mRNA or a polypeptide. The end result is always an uncontrolled growth of the mutated population of cells as a result of either increased proliferative rates, decreased apoptotic rates and/or failure to respond to normal growth control signals.

Gene loci which are altered in the progression of such disorders are not always the primary or direct target of the initial mutation however. Rather, a mutation may exist in a genomic locus which codes for an "upstream" factor. Mutation of the upstream factor may not produce a malignant phenotype to a cell by itself. However, the mutation of the upstream factor does impact upon "downstream" factors, the genomic locus of which remains essentially wild-type.

One such upstream factor is a factor capable of methylating genomic sequences. Abnormal methylation of genomic loci has been reported to cause altered expression levels from that genomic locus. The mammalian genome is widely methylated except for regions rich in CG dinucleotides (e.g., CpG islands) which are undermethylated as compared to the rest of the genome, in normal cells. Aberrant methylation, particularly at CpG islands, is reportedly accompanied by gene silencing and is reportedly one mechanism responsible for the inactivation of several tumor suppressor genes in human cancers. The invention described herein is premised, in part, on the finding that cells overexpressing methyltransferase can be used to identify genomic loci susceptible to abnormal methylation. The discovery was thus made that a cell overexpressing a methyltransferase exhibited abnormal methylation of CpG island in particular loci, thereby leading to the silencing of these loci. More specifically, the TMS1 (Target of Methylation-induced Silencing-1) gene was identified as one such genomic locus which is silenced in the presence of methyltransferase overexpression due to abnormal methylation of a CpG island in its 5' regulatory region. It was further discovered that TMS1 is a target of methylation associated silencing in human cancer.

Thus, one aspect of the invention involves the cloning of a human cDNA, 770 bp in size, encoding TMS1, represented by SEQ ID NO:2. The human TMS1 polypeptide is predicted to be a 25 kDa protein, believed to function in the regulation of cell death. The predicted amino acid sequence of the encoded human protein product is presented as SEQ ID NO:3. "TMS1 activity" intends, at least, an apoptosis inducing activity. The human TMS1 genomic sequence comprises the sequence of SEQ ID NO:1. SEQ ID NO:20 represents the nucleotide sequence of the mouse TMS1 cDNA, with the amino acid sequence of the polypeptide it is predicted to encode shown in SEQ ID NO:21. SEQ ID NO:22 represents the partial nucleotide sequence of the rat TMS1 cDNA, with the partial amino acid sequence of the polypeptide it is predicted to encode shown in SEQ ID NO:23. SEQ ID NO:24 is the nucleotide sequence of an alternatively spliced form of TMS1 which lacks exon 2. This latter nucleic acid encodes the polypeptide having amino acid sequence of SEQ ID NO:25. SEQ ID NO:26 represents the nucleotide sequence of an alternatively spliced form of TMS1 that lacks exon 3, with the amino acid sequence it is predicted to encode shown in SEQ ID NO:27.

Apoptosis is a programmed cell death available to almost every normal non-malignant cell and is triggered in such a cell when cell age or integrity dictate. It is an active process often morphologically characterized by cleavage of the genomic DNA into fragments, giving rise to a DNA "ladder" pattern upon gel electrophoresis. "Blebbing" of the plasma membrane is also a common feature of apoptosing cells. Apoptotic pathways are believed to play an integral role in ensuring the elimination of cells which have undergone mutation and have failed to repair such mutation. Thus, apoptosis is a normal process by which normal cells are selected for and potentially mutant cells are selected against. Commonly, cancer cells de-activate apoptotic pathways, and therefore are capable of propagating themselves in spite, and perhaps as a result, of the mutation they have acquired. Mutation which prohibits or reduces the likelihood of apoptosis suffices as one of the several mutations necessary for cancer development. As used herein, the term mutation is used broadly to encompass both mutation (i.e., change) at the genetic level and overall alteration of a cell profile which may or may not be due to a recognized mutation at the genetic level. Abnormal methylation, particularly when accompanied by inappropriate gene silencing, may also suffice as one such mutation in the development of a malignancy.

Comparison of TMS1 nucleic acid sequences (e.g., SEQ ID NO:1, SEQ ID NO:2, SEQ ID NO:20, SEQ ID NO:22 or SEQ ID NO:24) to nucleic acid and protein databases show that TMS1 possesses a carboxy terminal caspase-recruiting domain (CARD), a recently described interaction motif common to some apoptotic signaling molecules and reported to mediate homophilic interactions between such molecules. Similar in structure and function to the death domain and the death effector domain, the CARD is a homotypic protein interaction domain found in proteins that function in the regulation and execution of apoptosis. (Hofmann, K., et al., Trends.Biochem.Sci. 22:155–156, 1997) The CARD exists within the prodomain of several caspases, and homotypic oligomerization with upstream CARD signaling proteins mediates their cleavage and activation. (Hofmann, K. Cell Mol.Life Sci. 55:1113–1128, 1999) Other CARD-containing proteins with known roles in apoptosis include the C. elegans CED-3 and CED-4, the human homolog of CED-4, Apaf1, the cellular and viral inhibitors of apoptosis (cIAPs), the cellular homolog of herpesvirus EHV2 E10, Bc110/mE10/CIPERTCLAP/CARMEN, and several proteins involved in the activation of NF-κB. (Hofmann, K. Cell Mol.Life Sci. 55:1113–1128, 1999) An alignment of TMS1 with other known human CARDs indicated that the TMS1 CARD was most similar to that of the serine/threonine kinase RICK/CARDIAK/RIP2 (25% identity, 51% similarity) and CARD4/Nod1 (24% identity, 44% similarity), a CED-4/Apaf1 family member that binds to RICK as well as procaspase 9. (Inohara, N. et al., J.Biol.Chem. 273:12296–12300, 1998; McCarthy, J. V. et al., J.Biol.Chem. 273:16968–16975, 1998; Thome, M., et al., Curr.Biol. 8:885–888, 1998; Bertin, J., et al., J.Biol.Chem. 274:12955–12958, 1999; Inohara, N., et al., J.Biol.Chem. 274:14560–14567, 1999)

Thus, one function of native TMS1 polypeptides is apoptosis induction. Induction of apoptosis can be assayed in a number of ways. Commonly, a TMS1 nucleic acid molecule or a polypeptide would be introduced into a cell. The cell can then be observed for any number of phenotypic changes such as DNA ladder formation, blebbing of the plasma membrane, and for adherent cells particularly, condensation, rounding up and detachment from a growth substratum. Functional measurements can also be used to assess apoptosis. One example of a functional assay is the ability of TMS1 molecules to decrease, or halt altogether, the proliferation of cells which lack endogenous TMS1, such as some breast cancer cells (e.g., ZR75-1, Hs578t and MB231). Cell proliferation can be measured by incorporation of tritiated thymidine or in vitro cell growth as indicated by cell count and/or colony forming ability. Compounds which have ar; apoptotic function should inhibit or reduce colony forming activity, or prevent increases in cell counts and/or tritiated thymidine incorporation. As the Examples will show, TMS1 and variants of TMS1 retaining the CARD are able to promote apoptosis and inhibit colony formation when ectopically expressed. As also shown in the Examples, overexpression of TMS1 nucleic acid molecules induces apoptosis of cells, regardless of whether they express TMS1 expression products prior to treatment.

The invention thus involves in one aspect an isolated TMS1 polypeptide, the genomic DNA (including the promoter region and the CpG island) and cDNA encoding this polypeptide, the genomic locus necessary for assessment of CpG island methylation, functional modifications and variants of the foregoing, useful fragments of the foregoing, as well as diagnostics and therapeutics relating thereto.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein with respect to polypeptides, the term "isolated" means separated from its native environment in sufficiently pure formn so that it can be manipulated or used for any one of the purposes of the invention. Thus, isolated means sufficiently pure to be used (i) to raise and/or isolate antibodies, (ii) as a reagent in an assay, or (iii) for sequencing, etc.

According to the invention, isolated TMS1 nucleic acid molecules include: (a) nucleic acid molecules which hybridize under stringent conditions to a complement of a molecule consisting a nucleotide sequence selected from the group consisting of SEQ ID NO:1, SEQ ID NO:2, SEQ ID NO:5, SEQ ID NO:7, SEQ ID NO:9, SEQ ID NO:20, SEQ ID NO:22, SEQ ID NO:24 and SEQ ID NO:26 and which code for a native TMS1 polypeptide, (b) deletions, additions and substitutions of (a) which code for an apoptosis-inducing polypeptide, (c) nucleic acid molecules that differ from the nucleic acid molecules of (a) or (b) in codon sequence due to the degeneracy of the genetic code, and (d) complements of (a), (b) or (c). In one embodiment, the nucleotide sequence is selected from the group consisting of SEQ ID NO:1, SEQ ID NO:2, SEQ ID NO:20, SEQ ID NO:22 and SEQ ID NO:24, while in others it is SEQ ID NO:26.

Homologs and alleles of the TMS1 nucleic acids of the invention can be identified by conventional techniques. Thus, an aspect of the invention is those nucleic acid sequences which code for TMS1 polypeptides and which hybridize to a nucleic acid molecule consisting of the coding region of preferably SEQ ID NO:1, SEQ ID NO:2 or SEQ ID NO:24, or in other embodiments SEQ ID NO:20, SEQ ID NO:22, or in still other embodiments SEQ ID NO:26, and in yet other embodiments SEQ ID NO:5, SEQ ID NO:7 or SEQ ID NO:9, under stringent conditions. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, New York, 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrolidone, 0.02% Bovine Serum Albumin, 2.5 mM $NaH_2PO_4$(pH7), 0.5% SDS, 2 mM EDTA). SSC is 0.15M sodium chloride/ 0.015M sodium citrate, pH7; SDS is sodium dodecyl sulphate; and EDTA is ethylenediaminetetracetic acid. After hybridization, the membrane upon which the DNA is transferred is washed at 2×SSC at room temperature and then at 0.1×SSC/0.1% SDS at temperatures up to 68° C.

There are other conditions, reagents, and so forth which can be used, and would result in a similar degree of stringency. The skilled artisan will be familiar with such conditions, and thus they are not given here. It will be understood, however, that the skilled artisan will be able to manipulate the conditions in a manner to permit the clear identification of homologs and alleles of TMS1 nucleic acids of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 75% nucleotide identity to SEQ ID NO:1, SEQ ID NO:2 or SEQ ID NO:24, and/or at least 90% amino acid identity to SEQ ID NO:3 or SEQ ID NO:25. Preferably, homologs and alleles will share at least 85% nucleotide identity and/or at least 95% amino acid identity and, even more preferably, at least 95% nucleotide identity and/or at least 99% amino acid identity will be shared. The homology can be calculated using various, publicly available software tools developed by NCBI (Bethesda, Md.) that can be obtained through the NCBI website on the internet. Exemplary software tools include the BLAST system (available on the internet at the NIH website) using default settings. Pairwise and ClustalW alignments (BLOSUM30 and/or BLOSUM62 matrix settings) as well as Kyte-Doolittle hydropathic analysis can be obtained using the MacVetor sequence analysis software (Oxford Molecular Group). Watson-Crick complements of the foregoing nucleic acids also are embraced by the invention. Homologs and alleles having nucleotide identity as stated above to SEQ ID NO:5, SEQ ID NO:7, SEQ ID NO:9, SEQ ID NO:20, SEQ ID NO:22 or SEQ ID NO:26, or having amino acid identity to SEQ ID NO:6, SEQ ID NO:8, SEQ ID NO:10, SEQ ID NO:21, SEQ ID NO:23 or SEQ ID NO:27 are also embraced by the invention.

In screening for TMS1 related genes, such as homologs and alleles of TMS1, a Southern blot may be performed using the foregoing conditions, together with a radioactive probe. After washing the membrane to which the DNA is finally transferred, the membrane can be placed against X-ray film or a phosphoimager plate to detect the radioactive signal.

Given that the TMS1 gene is expressed in certain tissues, and given the teachings herein of a full-length human, murine and partial rat TMS1 cDNA clone, sequences from other mammalian species corresponding to the TMS1 gene can be isolated from a cDNA library prepared from one or more of the tissues in which TMS1 expression is abundant, using standard colony hybridization techniques.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating TMS1 polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

In another aspect, the invention provides a genomic nucleic acid sequence of TMS1 (i.e., SEQ ID NO:1). This sequence contains at least one native regulatory sequence of TMS1. One such native regulatory sequence or element of TMS1 is a CpG island located at nucleotides 1100–1725 of SEQ ID NO:1 and surrounding exon 1. The nucleotide sequence of this CpG island is herein referred to as SEQ ID NO:4. In some abnormal cells, CpG islands become methylated at the cytosine residue by a host of methylating enzymes, including methylases and methyltransferases. Methyltransferases are enzymes which add methyl groups from S-adenosyl methionine to bases in DNA strands. This region of SEQ ID NO:1 possesses at least one CpG island, the methylation of which induces TMS1 silencing. Nucleic acid sequences and expression vectors comprising the CpG island are useful for studying the mechanism of TMS1 methylation and identifying methylases or methyltransferases which act upon this CpG island and therapeutic agents which block such methylation.

Examples of methylating enzymes capable of CpG methylation include human DNA methyltransferases such as DNMT1 (e.g., Accession numbers X63692 and NM_001379; Yen, R. W., Nuc.Acids Res. 20:2287–2291, 1992), DNMT2, DNMT3a and DNMT3a variants, DNMT3b and DNMT3b variants, as well as corresponding murine DNA methyltransferases such as Dnmt1, Dnmt2, Dnmt3a and Dnmt3b (e.g., Accession number U70051; Tucker, K. L., Proc.Natl.Acad.Sci.U.S.A. 93:12920–12925, 1996). The methylation events with which the invention is most concerned are methylation of cytosines, specifically, events leading to the formation of 5-methylcytosine. The genomic sequence (i.e., SEQ ID NO:1) is useful in elucidating the mechanisms through which TMS1 is silenced. The sequence facilitates the identification of (a) methylating agents which target the CpG island, (b) inhibitors of such methylating agents, (c) mutations within the sequence which would render it less susceptible to methylation induced silencing, (d) other regulatory sequences within nucleic acid sequences comprising SEQ ID NO:1 which control the transcription or translation of TMS1 expression products, and (e) factors which bind to such regulatory sequences. Regulatory sequences, other than the CpG islands, which are present within genomic TMS1 nucleic acids include, are not limited to, promoters, enhancers and still other repressors sequences. Agents which bind to these sequences can be readily identified using standard nucleic acid binding assays that are well known in the art.

The invention also provides isolated unique fragments of SEQ ID NO:1, SEQ ID NO:2 and SEQ ID NO:24 or complements thereof. A unique fragment is one that is a 'signature' for the larger nucleic acid. For example, the unique fragment is long enough to assure that its precise sequence is not found in molecules within the human genome outside of the TMS1 nucleic acids defined above (and human alleles). Those of ordinary skill in the art may apply no more than routine procedures to determine if a fragment is unique within the human genome. Unique fragments, however, exclude fragments completely composed of the nucleotide sequences of any of GenBank accession numbers listed in Table I which were published prior to the priority or filing date of the present invention (see below), or other previously published sequences as of the priority date or filing date of this application.

A fragment which is completely composed of the sequence described in the foregoing GenBank deposits is one which does not include any of the nucleotides unique to the sequences of the invention. Thus, a unique fragment must contain a nucleotide sequence other than the exact sequence of those in GenBank or fragments thereof, provided that the GenBank or fragment sequences were published prior to the priority or filing date of the present application, depending on the sequence disclosed herein. The difference may be an addition, deletion or substitution with respect to all or part of the GenBank sequence or it may be a sequence wholly separate from the GenBank sequence.

Unique fragments can be used as probes in Southern and Northern blot assays to identify such nucleic acids, or can be used in amplification assays such as those employing PCR. As known to those skilled in the art, large probes such as 200, 250, 300 or more nucleotides are preferred for certain uses such as Southern and Northern blots, while smaller fragments will be preferred for uses such as PCR. Unique fragments also can be used to produce fusion proteins for generating antibodies or determining binding of the polypeptide fragments or for generating immunoassay components. Likewise, unique fragments can be employed to produce nonfused fragments of the TMS1 polypeptides, useful, for example, in the preparation of antibodies, immunoassays or therapeutic applications.

As will be recognized by those skilled in the art, the size of the unique fragment will depend upon its conservancy in the genetic code. Thus, some regions of SEQ ID NO:1, SEQ ID NO:2, or SEQ ID NO:24, or complements thereof will require longer segments to be unique while others will require only short segments, typically between 12 and 32 nucleotides long (e.g. 12, 13, 14, 15, 16, 17, 18, 19, 20, 21, 22, 23, 24, 25, 26, 27, 28, 29, 30, 31 and 32 bases) or more, up to the entire length of the disclosed sequence. As mentioned above, this disclosure intends to embrace each and every fragment of each sequence listed, beginning at the first nucleotide, the second nucleotide and so on, up to 8 nucleotides short of the end, and ending anywhere from nucleotide number 8, 9, 10 and so on for each sequence listed, up to the very last nucleotide, provided the sequence is unique as described above. Taking into account the exclusion described above, virtually any segment of the region of SEQ ID NO:1 beginning at nucleotide 1 and ending at nucleotide 2821, or SEQ ID NO:2 beginning at nucleotide 1 and ending at nucleotide 770, or complements thereof, that is 20 or more nucleotides in length will be unique. Those skilled in the art are well versed in methods for selecting such sequences, typically on the basis of the ability of the unique fragment to selectively distinguish the sequence of interest from other sequences in the human genome. Comparison of the fragment to those on known databases typically is all that is necessary, although in vitro confirmatory hybridization and sequencing analysis may be performed.

The invention also involves expression vectors coding for TMS1 proteins and fragments and variants thereof and host cells containing those expression vectors. Virtually any cells, prokaryotic or eukaryotic, which can be transformed with heterologous DNA or RNA and which can be grown or maintained in culture, may be used in the practice of the invention. Examples include bacterial cells such as E.coli and mammalian cells such as mouse, hamster, pig, goat, primate, etc. They may be of a wide variety of tissue types, including mast cells, fibroblasts, oocytes and lymphocytes, and they may be primary cells or cell lines. Specific examples include CHO cells and COS cells. Cell-free transcription systems also may be used in lieu of cells.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

In aspects involving the native regulatory sequences of TMS1, for example, the CpG island located at nucleotides 1100–1725 of SEQ ID NO:1 (i.e., SEQ ID NO:4) or the intronic sequences of TMS1, useful expression vectors are those which comprise a reporter coding sequence. Intronic sequences of TMS1 correspond to nucleotides 1530–1742 of SEQ ID NO:1 (intron 1) and nucleotides 1800–2104 of SEQ ID NO:1 (intron 2). A reporter coding sequence as used herein refers to at least a marker sequence, the expression of which when it is operably linked to a foreign regulatory sequence reflects the transcriptional function of the foreign sequence. The regulatory potential of such a foreign sequence can be deduced by assaying for the presence of an expression product of the marker sequence. Foreign regulatory sequences which can be tested in this manner include, but are not limited to, promoters, and other elements which although capable of affecting transcriptional levels are not, in and of themselves, sufficient for such transcription. Examples of these latter elements include enhancers and repressor elements. In order to assess the activity of enhancers and repressors, it may be necessary for the reporter coding sequence to consist of a regulatory sequence, such as a minimal promoter element, as well as the requisite marker sequence. Minimal promoter elements have been recognized in the art and include sequences such as a CCAAT box or a TATA sequence. Suitable marker sequences for these purposes are similar to those described above.

As used herein, a marker or coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CCAAT sequence, and the like. Especially, such 5' non-transcribed regulatory sequences will include a promoter region which includes a promoter sequence for transcriptional control of the operably joined coding sequence. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous nucleic acid, usually DNA, molecules, encoding a TMS1 polypeptide or fragment or a variant thereof. The heterologous nucleic acid molecules are placed under operable control of transcriptional elements to permit the expression of the heterologous nucleic acid molecules in the host cell.

Preferred systems for mRNA expression in mammalian cells are those such as pcDNA3.1 (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen, Carlsbad, Calif.), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (Nuc. Acids Res. 18:5322, 1990), and its use in transfection experiments is disclosed by, for example, Demoulin (Mol. Cell. Biol. 16:4710–4716, 1996). Still another preferred expression vector is an adenovirus, described by Stratford-Perricaudet, which is defective for E1 and E3 proteins (J. Clin. Invest. 90:626–630, 1992). The use of the adenovirus as an Adeno.P1A recombinant is disclosed by Warnier et al., in intradermal injection in mice for immunization against P1A (Int. J. Cancer, 67:303–310, 1996).

The invention also embraces so-called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

It will also be recognized that the invention embraces the use of the above described, TMS1 cDNA sequence containing expression vectors, to transfect host cells and cell lines, be these prokaryotic (e.g., *E. coli*), or eukaryotic (e.g., CHO cells, COS cells, yeast expression systems and recombinant baculovirus expression in insect cells). Especially useful are mammalian cells such as human, mouse, hamster, pig, goat, primate, etc., from a wide variety of tissue types including primary cells and established cell lines. Specific examples include mammalian epithelial cells, fibroblast cells and kidney epithelial cells, either as primary cells or cell lines. Of particularly importance according to some of the embodiments of the invention are cells which can be easily induced to apoptose such as epithelial cells.

The invention also provides isolated polypeptides (including whole proteins and partial proteins), encoded by the foregoing TMS1 nucleic acids, and include the polypeptides having amino acids sequences selected from the group consisting of SEQ ID NO:3, SEQ ID:21, SEQ ID NO:23, and SEQ ID NO:25 and in some instances, unique fragments thereof. Such polypeptides are useful, for example, alone or as fusion proteins that retain at least one TMS1 activity (e.g., apoptosis induction), in the generation of antibodies, as components of an immunoassay, or as a binding partner in a binding assay. Polypeptides can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Short polypeptides, including antigenic peptides (such as those presented by MHC molecules on the surface of a cell for immune recognition) also can be synthesized chemically using well-established methods of peptide synthesis.

A unique fragment of a TMS1 polypeptide, in general, has the features and characteristics of unique fragments of nucleic acids as discussed above. As will be recognized by those skilled in the art, the size of the unique fragment will depend upon factors such as whether the fragment constitutes a portion of a conserved protein domain. Thus, some regions of SEQ ID NO:3 or SEQ ID NO:24, for example, will require longer segments to be unique while others will require only short segments, typically between 5 and 12 amino acids (e.g., 5, 6, 7, 8, 9, 10, 11, 12, 13, 14, 15, 20, 25, 30, 40, 50, 60, 70, 80, 90, 100, 110, 120, 130, 140, and 150 amino acids long or more, including each integer from 15 up to the full length, 195 amino acids long). Virtually any segment of, for example, SEQ ID NO:3 that is 9 or more amino acids in length will be unique. A similar rationale applies to the unique fragments of SEQ ID NO:24.

Unique fragments of a polypeptide preferably are those fragments which retain at least one distinct functional capability of the native TMS1 polypeptide. Functional capabilities which can be retained in a unique fragment of a polypeptide include interaction with antibodies and/or other polypeptides or fragments thereof (including other TMS1 polypeptides, or other CARD containing polypeptides, or fragments thereof), as well as, for a subset of unique fragments, the ability to induce apoptosis. One important activity is the ability to act as a signature for identifying the polypeptide. Those skilled in the art are well versed in methods for selecting unique amino acid sequences, typically on the basis of the ability of the unique fragment to selectively distinguish the sequence of interest from non-family members. A comparison of the sequence of the fragment to those in known databases is all that is typically required. Preferably, the unique fragment is unique in humans, i.e., it is long enough to assure that its precise sequence is not found in molecules encoded by the human genome outside of TMS1 polypeptides including alleles.

The invention embraces variants of the TMS1 polypeptides described above. As used herein, a "variant" of a TMS1 polypeptide is a polypeptide which contains one or more modifications to the primary amino acid sequence of a TMS1 polypeptide. Modifications which create a TMS1 polypeptide variant are typically made to the nucleic acid which encodes the TMS1 polypeptide, and can include deletions, point mutations, truncations, amino acid substitutions and addition of amino acids or non-amino acid moieties to: 1) reduce or eliminate an activity of a TMS1 polypeptide; 2) enhance a property of a TMS1 polypeptide, such as protein stability in an expression system or the stability of protein-protein binding; 3) provide a novel activity or property to a TMS1 polypeptide, such as addition of an antigenic epitope or addition of a detectable moiety; or 4) to provide equivalent or better binding to a TMS1 polypeptide receptor or other molecule. Alternatively, modifications can be made directly to the polypeptide, such as by cleavage, addition of a linker molecule, addition of a detectable moiety, such as biotin, addition of a fatty acid, and the like. Variants which reduce or eliminate TMS1 activity are useful, for example, as experimental tools to study the effects of progressively reduced TMS1 expression product levels. Therapeutic tools, on the other hand, might employ variants which provide an enhanced TMS1 activity (e.g., enhanced apoptosis induction). Modifications also embrace fusion proteins comprising all or part of the TMS1 amino acid sequence.

One of skill in the art will be familiar with methods for predicting the effect on protein conformation of a change in protein sequence, and can thus "design" a variant TMS1 polypeptide according to known methods. One example of such a method is described by Dahiyat and Mayo in Science 278:82–87, 1997, whereby proteins can be designed de novo. The method can be applied to a known protein to vary only a portion of the polypeptide sequence. By applying the computational methods of Dahiyat and Mayo, specific variants of a TMS1 polypeptide can be proposed and tested to determine whether the variant retains a desired conformation.

Variants can include TMS1 polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a TMS1 polypeptide by eliminating proteolysis by proteases in an expression system (e.g., dibasic amino acid residues in yeast expression systems in which KEX2 protease activity is present).

Mutations of a nucleic acid which encodes a TMS1 polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant TMS1 polypeptides) which are silent as to the amino acid sequence of the polypeptide, but which provide preferred codons for translation in a particular host. The preferred codons for translation of a nucleic acid in, e.g., E. coli, are well known to those of ordinary skill in the art. Still other mutations can be made to the noncoding sequences of a TMS1 gene or cDNA clone to enhance expression of the polypeptide.

The skilled artisan will realize that conservative amino acid substitutions may be made in TMS1 polypeptides to provide functionally equivalent variants of the foregoing polypeptides, i.e., the variants retain the functional capabilities of the TMS1 polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, New York, 1989, or *Current Protocols in Molecular Biology*, F. M. Ausubel, et al., eds., John Wiley & Sons, Inc., New York. Exemplary functionally equivalent variants of the TMS1 polypeptides include conservative amino acid substitutions of SEQ ID NO:3. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Thus, functionally equivalent variants of TMS1 polypeptides, i.e., variants of TMS1 polypeptides which retain the function of the natural TMS1 polypeptides, are contemplated by the invention. Conservative amino-acid substitutions in the amino acid sequence of TMS1 polypeptides to produce functionally equivalent variants of TMS1 polypeptides typically are made by alteration of a nucleic acid encoding TMS1 polypeptides (e.g., SEQ ID NO:1, SEQ ID NO:2, SEQ ID NO:20, SEQ ID NO:22, and SEQ ID NO:24). Such substitutions can be made by a variety of methods known to one of ordinary skill in the art. For example, amino acid substitutions may be made by PCR-directed mutation, site-directed mutagenesis according to the method of Kunkel (Kunkel, Proc. Nat. Acad. Sci. U.S.A. 82: 488–492, 1985), or by chemical synthesis of a nucleic acid molecule encoding a TMS1 polypeptide. The activity of functionally equivalent fragments of TMS1 polypeptides can be tested by cloning the gene encoding the altered TMS1 polypeptide into a bacterial or mammalian expression vector, introducing the vector into an appropriate host cell, expressing the altered TMS1 polypeptide, and testing for a functional capability of the TMS1 polypeptides as disclosed herein.

The invention as described herein has a number of uses, some of which are described elsewhere herein. First, the invention permits isolation of TMS1 nucleic acid molecules which code for a TMS1 polypeptide. As described above, nucleic acid isolation can be performed using hybridization under stringent conditions. A second use of the invention is the isolation of TMS1 polypeptides, using a variety of methodologies well-known to the skilled practitioner. The TMS1 polypeptide may be purified from cells which naturally produce it by chromatographic means or immunological recognition. Alternatively, an expression vector which incorporates a coding TMS1 nucleic acid molecule, such as SEQ ID NO:1 and perhaps preferably SEQ ID NO:2, SEQ ID NO:20, SEQ ID NO:22 and SEQ ID NO:24, may be introduced into cells to cause production of the TMS1 polypeptide. In still other embodiments, expression vectors which incorporate SEQ ID NO:5, SEQ ID NO:7, SEQ ID NO:9 or SEQ ID NO:26 may be introduced into cells as well. In another method, mRNA transcripts may be microinjected or otherwise introduced into cells to cause production of the encoded polypeptide. Translation of TMS1 mRNA in cell-free extracts such as the reticulocyte lysate system also may be used to produce TMS1 polypeptides. Those skilled in the art also can readily follow known methods for isolating TMS1 polypeptides. These include, but are not limited to, immunochromatography, HPLC, size-exclusion chromatography, ion-exchange chromatography and immune-affinity chromatography.

The invention further provides efficient methods of identifying agents or lead compounds for agents active at the level of a TMS1 or TMS1 fragment dependent cellular function. Generally, the screening methods involve assaying for compounds which enhance TMS1 activity. Such methods are adaptable to automated, high throughput screening of compounds.

The invention provides TMS1-specific binding agents, methods of identifying and making such agents, and their use in diagnosis, therapy and pharmaceutical development. For example, TMS1-specific pharmacological agents are useful in a variety of diagnostic and therapeutic applications, especially where disease or disease prognosis is associated with altered TMS1 binding characteristics. Novel TMS1-specific binding agents include TMS1-specific antibodies, cell surface receptors, and other natural intracellular binding agents identified with assays such as two hybrid screens, and non-natural intracellular and extracellular binding agents identified in screens of chemical libraries and the like.

Accordingly, the invention also embraces agents that bind to the TMS1 polypeptides. One category of such agents is isolated peptide binding agents which, for example, can be antibodies or fragments of antibodies ("binding polypeptides"), having the ability to selectively bind to TMS1 polypeptides. Antibodies include polyclonal and monoclonal antibodies and can be prepared according to conventional methodology. Such antibodies can be further manipulated to create chimeric or humanized antibodies as will be discussed in greater detail below.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of co-specific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions has been replaced by FR regions of human origin. Such antibodies, including fragments of intact antibodies with antigen-binding ability, are of ten referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention provides a variety of polypeptides of varying size and type that bind specifically to TMS1 polypeptides, and complexes of both TMS1 polypeptides and their binding partners. These polypeptides may be derived also from sources other than antibody technology. For example, such polypeptide binding agents can be provided by degenerate peptide libraries which can be readily prepared in solution, in immobilized form, as bacterial flagella peptide display libraries or as phage display libraries. Combinatorial libraries of peptides containing one or more amino acids also can be synthesized. Similarly, libraries of peptides and non-peptide synthetic moieties can be synthesized.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the TMS1 polypeptide or a complex of a TMS1 polypeptide and a binding partner. This process can be repeated through several cycles of reselection of phage that bind to the TMS1 polypeptide or complex. Repeated rounds lead to enrichment of phage bearing particular sequences. DNA sequence analysis can be performed to identify the sequences of the expressed polypeptides. The minimal linear portion of the sequence that binds to the TMS1 polypeptide or complex can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the TMS1 polypeptides. Thus, the TMS1 polypeptides of the invention, or a fragment thereof, or complexes of TMS1 polypeptides and a binding partner can be used to screen peptide libraries, including phage display libraries, to identify and select peptide binding partners of the TMS1 polypeptides of the invention. Such molecules can be used, as described, for screening assays, for purification protocols, for interfering directly with the functioning of TMS1 polypeptides and for other purposes apparent to those of ordinary skill in the art.

A TMS1 polypeptide, or a fragment thereof, also can be used to isolate their native binding partners, according to one aspect of the invention. Isolation of binding partners may be performed according to well-known methods. For example, isolated TMS1 polypeptides can be attached to a substrate, and then a solution suspected of containing a TMS1 binding partner may be applied to the substrate. If the binding partner for TMS1 polypeptides is present in the solution, then it will bind to the substrate-bound TMS1 polypeptide. The binding partner then may be isolated. Other proteins capable of binding to TMS1 polypeptides may be similarly isolated using no more than routine experimentation.

As an example of one such method, the invention provides a method for identifying a TMS1 polypeptide binding partner. The method involves performing a test binding assay between a TMS1 polypeptide and a library member and comparing the extent of binding between the TMS1 polypeptide and the library member with a control. The control binding assay can be performed using the same environment as the test binding assay but lacking the TMS1 molecule. The test binding assay result indicates the extent of binding between the TMS1 molecule and the library member. The method further involves comparing the test binding assay result with the control binding assay result. A test binding assay result that is greater than a control binding assay result indicates that the library member is a TMS1 polypeptide binding partner.

The TMS1 polypeptide to be used in the test binding assay will depend upon the type of specific binding partner desired. For example, if a binding partner for the CARD of TMS1 polypeptide was desired, polypeptides useful in the test binding assay would preferably be those that comprise a CARD. Even more preferably, the polypeptides may derive from the TMS1 genomic locus. Examples include polypeptides which comprise an amino acid sequence selected from the group consisting of SEQ ID NO:3, SEQ ID NO:10, SEQ ID NO:21, SEQ ID NO:23 and SEQ ID NO:25. In this latter example, the library member may be pre-selected by prior exposure to polypeptides which lack the CARD such as polypeptides consisting of an amino acid sequence selected from the group consisting of SEQ ID NO:5, SEQ ID NO:7, and SEQ ID NO:27. This pre-selection step is most appropriate where the CARD-containing polypeptide used in the test binding assay also includes regions and/or domains of TMS1 other than the CARD domain. An agent that is capable of binding to the CARD of TMS1 polypeptide is referred to herein as a TMS1 CARD binding partner.

As another example, a similar assay can be used to identify binding partners of the N-terminal domain of TMS1 (i.e., TMS1 N-terminal binding partners). Such assays and terminal domains are an aspect of the present invention. A TMS1 N-terminal polypeptide as used herein is a polypeptide that comprises at a minimum the N-terminal domain of TMS1, including either or both exon 1 and exon 2. In preferred embodiments, the TMS1 N-terminal polypeptide comprises at a minimum exon 1 from a TMS1 nucleic acid molecule. It should be understood that some but not necessarily all TMS1 molecules are TMS1 N-terminal molecules. In this screening method, a test binding assay is performed between a TMS1 N-terminal polypeptide and a library member and compared to a control binding assay. A test binding assay result that is greater than the control binding assay result is indicative of a library member that is a TMS1

N-terminal binding partner. The TMS1 N-terminal polypeptide preferably has an amino acid sequence selected from the group consisting of SEQ ID NO:6, SEQ ID NO:8 and SEQ ID NO:27, but is not so limited. In one embodiment, the TMS1Δ100–195 construct described in the Examples may be used as a TMS1 N-terminal molecule. The TMS1 N-terminal polypeptide used in the test binding assay may have an amino acid sequence selected from the group consisting of SEQ ID NO:3, SEQ ID NO:21, SEQ ID NO:23 or SEQ ID NO:25. However, in these instances it may be preferably that the control binding assay is performed between a library member and a polypeptide having an amino acid sequence of SEQ ID NO:10. In this way, library members that are specific for the CARD rather than the N-terminal domain of TMS1 can be identified based on the comparison of the test result with the control. Alternatively, the library members may be undergo a round of negative pre-selection in which they are allowed to contact and bind to a polypeptide having an amino acid sequence of SEQ ID NO:10, prior to exposure to a TMS1 N-terminal polypeptide. Library members which bind to the CARD of TMS1 will be removed and those that bind to the N-terminal domain of TMS1 will be enriched.

TMS1 N-terminal polypeptides can be used as dominant negative forms of TMS1 which potentially bind to wild-type TMS1 (e.g., polypeptides having an amino acid sequence comprising SEQ ID NO:3 or SEQ ID NO:25) and thereby prevent the normal interactions of TMS1 with naturally occurring TMS1 binding partners. Alternatively, the TMS1 N-terminal polypeptides may function as dominant negatives by complexing with wild-type TMS1 polypeptides and thereby inhibiting their normal function (i.e., apoptosis induction). Accordingly, TMS1 N-terminal binding partners can be used to inhibit a potential dominant negative function of TMS1 N-terminal polypeptides, if and where this is required for therapeutic benefit.

Candidate binding partners are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily modified through conventional chemical, physical, and biochemical means. Further, known pharmacological agents may be subjected to directed or random chemical modifications such as acylation, alkylation, esterification, amidification, etc. to produce structural analogs of the agents.

The library member may be synthesized or it may be derived from natural sources (e.g., a cell or tissue lysate). In some important embodiments, the TMS1 polypeptide binding partner is naturally occurring. Binding partners identified according to the above methods may be further screened for their ability to either inhibit or promote the function of TMS1 using apoptosis assay described in the Examples and those known in the art.

An agent that binds TMS1 polypeptides, such as an antibody, may be conjugated to a detectable label. Conjugation of the agent to a detectable label facilitates, among other things, the use of such agents in diagnostic assays. A detectable label is a moiety, the presence of which can be ascertained directly or indirectly. Generally, detection of the label involves an emission of energy by the label. The label can be detected directly by its ability to emit and/or absorb light of a particular wavelength. A label can be detected indirectly by its ability to bind, recruit and, in some cases, cleave another moiety which itself may emit or absorb light of a particular wavelength. An example of indirect detection is the use of a first enzyme label which cleaves a substrate into visible products. The label may be of a chemical, peptide or nucleic acid nature although it is not so limited. Other detectable labels include radioactive isotopes such as $P^{32}$ or $H^3$, luminescent markers such as fluorochromes, optical or electron density markers, etc., or epitope tags such as the FLAG epitope or the HA epitope, biotin, avidin and enzyme tags such as horseradish peroxidase, β-galactosidase, etc.

A wide variety of assays for binding partners are provided, including, labeled in vitro protein-protein binding assays, electrophoretic mobility shift assays, immunoassays, cell-based assays such as two- or three-hybrid screens, expression assays, etc. For example, two-hybrid screens are used to rapidly examine the effect of transfected nucleic acids on the intracellular binding of TMS1 or TMS1 fragments to intracellular targets. The transfected nucleic acids can encode, for example, combinatorial peptide libraries or cDNA libraries. Convenient reagents for such assays, e.g., GAL4 fusion proteins, are known in the art. An exemplary cell-based assay involves transfecting a cell with a nucleic acid encoding a TMS1 polypeptide fused to a GAL4 DNA binding domain and a nucleic acid encoding a reporter gene operably linked to a gene expression regulatory region, such as one or more GAL4 binding sites. Activation of reporter gene transcription occurs when the TMS1 and reporter fusion polypeptides bind such as to enable transcription of the reporter gene. Agents which modulate a TMS1 polypeptide mediated cell function are then detected through a change in the expression of reporter gene. Methods for determining changes in the expression of a reporter gene are known in the art.

TMS1 fragments used in the methods, when not produced by a transfected nucleic acid are added to an assay mixture as an isolated polypeptide. TMS1 polypeptides preferably are produced recombinantly, although such polypeptides may be isolated from biological extracts. Recombinantly produced TMS1 polypeptides include chimeric proteins comprising a fusion of a TMS1 protein with another polypeptide, e.g., a polypeptide capable of providing or enhancing protein-protein binding, sequence specific nucleic acid binding (such as GAL4), enhancing stability of the TMS1 polypeptide under assay conditions, or providing a detectable moiety, such as green fluorescent protein or Flag epitope.

The invention also provides novel kits which could be used to measure the levels of the nucleic acids of the invention, expression products of the invention, anti-TMS1 antibodies, or levels of methylation of genomic TMS1 nucleic acid molecules. In the case of nucleic acid detection, pairs of primers for amplifying TMS1 nucleic acids cadf be included. The preferred kits would include controls such as known amounts of nucleic acid probes, TMS1 epitopes (such as TMS1 expression products), anti-TMS1 antibodies, or TMS1 genomic nucleic acid molecules with known amounts of methylation, as well as instructions or other printed material. In certain embodiments the printed material can characterize a risk of developing a disorder based upon the outcome of the assay. The reagents may be packaged in containers and/or coated on wells in predetermined amounts, and the kits may include standard materials such as labeled immunological reagents (such as labeled anti-IgG antibodies) and the like. As an example, one kit may contain a packaged polystyrene microtiter plate coated with TMS1 protein and a container housing labeled anti-human IgG antibodies. A well of the plate is contacted with, for example, serum, washed and then contacted with the anti-IgG antibody. The label is then detected. Various other kit components are described below in connection with performing the various assays of the invention.

The invention also provides a method for identifying nucleic acid molecules which are transcriptionally down-regulated following methylation. The method first involves overexpressing a methyltransferase molecule in an experimental cell. A differentially expressed molecule can then be identified as one which has a lower level of expression in the experimental cell than in a control. The control can be a cell, a tissue, a lysate of either, or a predetermined quantity of expression products present in a cell which does not overexpress a methyltransferase. Preferably, the control corresponds to the amount of expression products present in a parent cell from which the experimental cell was derived.

The differentially expressed molecules are essentially expression products (i.e., mRNA and/or polypeptides) which are differentially expressed in the experimental cell overexpressing a methyltransferase, as compared to a control. The differentially expressed molecule can be identified in a number of ways. If the expression product is a nucleic acid (i.e., an mRNA), then it may be identified using techniques such as subtractive hybridization, differential display or representational difference analysis. Virtually all approaches aimed at identifying differentially expressed transcripts require the conversion of RNA to at least a first strand cDNA. Moreover, since these strategies intend to capture as many difference sequences as possible, some of which may be known and some of which may be novel, a global cDNA synthesis is performed. A global cDNA synthesis is one in which an attempt is made to convert all RNA transcripts to cDNA. One way of doing this involves the reverse-transcription of RNA molecules with an oligo-dT primer, which hybridizes to the polyadenylated tail of RNA transcripts and primes the first strand synthesis reaction. The vast majority of mRNA transcripts are polyadenylated and thus can be captured in this way. In some instances, it is desirable that the proportional representation of mRNA transcripts be maintained through the cDNA synthesis and subsequent amplification. One way of achieving this is to limit the size of the first strand cDNA to about 700 bp. In so doing, the over-representation of shorter transcripts and under-representation of longer sequences, which would normally otherwise occur, is minimized. The first strand synthesis is then followed by the addition of a nucleic acid tract of known sequence onto the 3' end of the first cDNA strand. As an example, a homopolymer dA tract can be added to the 3' end using terminal transferase. At this point, the first strand cDNA having a dT stretch at its 5' end and a dA stretch at its 3' end, can be used as a template for the second cDNA strand using an oligo-dT primer. All subsequent amplifications require only oligo-dT as a primer. cDNA should be amplified equivalently due to their common priming ends. Another approach for synthesizing first strand cDNA involves the use of random hexamers which hybridize to mRNA transcripts with complementary sequences.

Subtractive hybridization generally involves the melting, combining and subsequent re-annealing of cDNA pools from a tester population and a driver population. Usually, when the aim of the subtractive hybridization is to identify a transcript which is expressed, the tester population is the population which expresses the transcript and the driver is the population which does not. In the present invention, the aim is to identify transcripts which as a result of methylation at the genomic level are down-regulated or silenced, the tester will be the population which expresses the transcript, i.e., the control, and the driver will be the experimental cell overexpressing the methyltransferase.

Driver cDNA is generally used in vast excess as compared to tester cDNA, in order to effect as much of a subtraction as possible. In some instances, it is desirable to self-subtract each population (i.e., the tester and the driver) prior to performing the subtraction. This serves to remove as many of the common, sometimes called housekeeping, genes which represent in some cell types the vast majority of transcripts. It is also desirable to convert each population into a single stranded form and to use these single stranded forms for the hybridization. The driver population commonly carries a marker which allows it to be removed after the hybridization, such as a biotin molecule. Biotin molecules can be easily added to nucleic acid using photobiotinylation as described by Barr et al. in Anal Biochem 186:369–373, 1990. The single stranded tester and biotinylated driver are then combined and allowed to hybridize under suitable salt and temperature conditions. Once annealing is complete, streptavidin is added and the entire mixture is phenol extracted. The phenol extraction serves to remove any nucleic acids to which the streptavidin has bound, including pure driver sequences and driver/tester hybrids. Ideally, the only nucleic acid sequences which remain in the aqueous phase are those which are expressed by the tester and not the driver populations. However, this is rarely accomplished with only one round of subtraction, and as a result, several rounds of subtraction must be performed to arrive at true difference sequences.

A modification of this technique described by Diatchenko et al. and called suppression subtractive hybridization, incorporates a normalization step to equalize cDNA abundance, and thereby reportedly requires only one cycle of hybridization. (Methods Enzymol 303:349–380, 1999) This latter approach was reported to increase the probability of obtaining low-abundance differentially expressed cDNA, a feature which may be desirable in the method of the invention, particularly if the gene which is silenced due to methylation is not expressed at high levels in the control. Difference sequences so identified can then be cloned, amplified, sequenced and used to isolate full-length transcripts.

Still other modifications of a basic subtractive hybridization have been reported. One of these includes the use of covalent bonding between specific complementary nucleotides. This approach, described by Ying and Lin in Biotechniques 26:966–8, 1999, chemically carboxylates pyrimidines in the driver population in order to achieve covalent affinity to the purines of the tester DNA. Still other methods aim to directly clone a full length differentially expressed sequence using multiple rounds of long-distance PCR, combined with a magnetic bead based subtraction. (Zhao et al., J Biotechnol 73:35–41, 1999) The experimentation required to achieve the foregoing is well within the realm of the ordinary artisan, and is reviewed by Blumberg and Belmonte in Methods Mol Biol 97:555–574, 1999.

Another important method in the analysis of differentially expressed transcripts is RDA. RDA was developed as a PCR-based subtraction method for cloning the 'difference' between two complex genomes. The technique has been adapted as a method to clone the differences between mRNA pools. Briefly, mRNA is converted to double stranded cDNA which is then digested with a four-base cutter like DpnII.

With an average cutting length of ~250 base pairs, most cDNA species will have at least one amplifiable fragment. Adapters are ligated to the digested cDNA and 'tester' (i.e., the control untreated cells) and 'driver' (i.e., DNMT overexpressing cells) cDNA pools are amplified using primers specific for the adapter. After removal of the adapter by re-digestion with DpnII, a second adapter is added only to the tester DNA. By using an unphosphorylated adapter only the top 24-mer is ligated to the 5' phosphate of the digested DNA. Tester and driver amplicons are then mixed, melted and reannealed using an excess of driver DNA. After filling in the overhangs, the resulting hybrids are then amplified using a primer specific for the adapter sequence present only on tester DNA. Whereas driver:driver hybrids will not amplify and tester:driver hybrids (i.e., sequences common between driver and tester pools) amplify linearly, tester:tester hybrids (i.e., those messages present only in the control cell population) will be amplified exponentially. By then subjecting the difference product to 1–2 further rounds of subtraction with successively higher driver:tester ratios, an enrichment for sequences present only in the tester population is achieved. Final difference products are then subcloned and sequenced. The RDA technique has been successfully applied by others to the isolation of target genes of transcriptional activators and differentially expressed genes during organ development.

The cloned difference products resulting from RDA are then used as probes on Northern blots to confirm down-regulation of expression resulting from DNMT overexpression. As a control, newly transfected or infected experimental cells are prepared along with their normal, control (i.e., untransfected, uninfected, or mock transfected or mock infected) counterparts. Expression of the newly identified difference clone is studied by Northern blot analysis using the subdloned difference product as the probe or by reverse transcriptase PCR using primers designed from sequence analysis of the difference product. Of particular interest are those genes that are specifically down-regulated as a result of overexpression of DNMT. Those difference products representing mRNAs that are consistently down-regulated in response to DNMT overexpression in independently generated experimental cells are reasonable candidates.

Sequences isolated in this manner that display DNMT-dependent silencing are then sequenced and compared to the GenBank non-redundant and EST databases using the BLAST algorithm. Subclones derived from the RDA technique will be small (200–300 bp) and could be derived from any part of the mRNA (i.e., the 3' end). Consequently, sequences may lie quite far on a genomic scale from the potential promoter and CpG island. Since CpG islands of ten surround exon 1 (for example, the CpG island of the TMS1 genomic locus), isolation of the 5' end of the cDNA will allow analysis of the methylation status of the CpG island.

If the database search reveals a known gene, cDNA clones and genomic promoter region clones/sequence information are likely to be available. If a novel gene is isolated, the 5' end of the corresponding cDNA is isolated using a variation of 5' RACE (rapid amplification of cDNA ends) developed and commercially available from Clontech. This procedure can be used to amplify the 5' end of the differentially expressed cDNAs from the 'tester' cDNA pool (i.e., the cDNA pool from which it was isolated ). Briefly, using the same full length oligo-dT primed double-stranded cDNA that was used to generate the 'tester' cDNA amplicon, a blunt-ended double-stranded adapter is ligated to either end without prior restriction such that the cDNA remains 'full-length'. Finally, a primer derived from the isolated sequence is paired with a primer specific to the adapter to yield either a product extending to the 5' or 3' end of the cDNA which can be distinguished based on the inclusion of the poly(A) tail in the 3' end product. Amplified product containing the 5' end is then subcloned.

Another commonly used technique includes differential display, which involves the amplification of two cDNA pools using arbitrary primers and visual comparison of the amplified pools in toto after separation on polyacrylamide gels. Although this technique is relatively simple to perform and somewhat less time consuming than RDA, the addition of a 'subtractive' component in the RDA technique greatly enriches for differentially expressed products and reduces the risk of false positives, a common pitfall of the differential display technique.

Another important technique for identifying differentially expressed transcripts involves DNA chip technology and cDNA microarray hybridization. This technique is gaining wide acceptance in the art due to its ability to analyze hundreds if not thousands of coding sequences at a time. Standard and custom-made DNA chips are now commercially available from manufacturers such as Affymetrix and InCyte. These approaches have evolved to the extent that high throughput screening for difference sequences can be readily accomplished. (Von Stein, et al., Nucleic Acids Res 25:2598–602, 1997; Carulli, et al., J Cell Biochem Suppl 30–31:286–96, 1998)

If the expression product is a polypeptide, then it may be identified using, for example, gel electrophoresis separation followed by Coomassie Blue staining. In this latter approach, differences between the experimental cell and a control may be revealed by the presence or absence of stained protein bands. Further separation, sequencing and cloning of these "difference band" would then be required, all of which are within the realm of the ordinary artisan.

The methyltransferase molecule may be a nucleic acid molecule or a polypeptide, as long as sufficient and sustained levels of methyltransferase activity can be effected in the experimental cell. Methyltransferase activity as used herein refers to the ability to methylate nucleic acid residues, particularly cytosines. Any type of methyltransferase can be used provided it is able to methylate cytosine residues in the experimental cell. Examples of methyltransferases useful in the invention include human DNA methyltransferases such as DNMT1, DNMT2, DNMT3a and variants thereof, and DNMT3b and variants thereof, as well as murine DNA methyltransferases such as Dnmt1, Dnmt2, Dnmt3a and Dnmt3b.

The experimental cell can be chosen from any number of cells, including primary cells and established cell lines. The use of established cell lines is more convenient in some instances. Examples of suitable experimental cells are epithelial cells and fibroblasts. In an important embodiment, the experimental cell is an SV40 immortalized version of a fibroblast cell line such as IMR90, which has been engineered to overexpress a DNA methyltransferase nucleic acid. Where primary cells are used, a breast epithelial cell or a fibroblast are suitable choices. The control cell is usually the non-DNMT expressing version of the experimental cell. As an example, if the experimental cell is an SV40 immortalized version of IMR90 overexpressing DNMT, the control would be an untreated SV40 immortalized version of IMR90 cells. SV40 immortalized versions of IMR90 cells are available from the National Institute on Aging Mutant Cell Repository (AG02804C).

The DNA methyltransferase (DNMT) nucleic acid can be introduced into experimental cells in any number of ways including calcium phosphate transfection, DEAE transfection, Lipofectamine® transfection, as well as infection methods using retro- or adenoviruses as an example. Suitable promoters for the constitutive expression of a coding sequence in a mammalian cell include the retroviral promoters contained in long-terminal repeats and the promoter and enhancer elements of CMV. The DNA methyltransferase can be constitutively overexpressed in the experimental cell as a result of being operably linked to a constitutive promoter. A preferred method for generating cells which overexpress DNMT is described in more detail in Vertino, P. M. et al., Mol.Cell Biol. 16:4555–4565, 1996. Alternatively, DNMT can be inducibly expressed through the use of inducible systems which are commercially available. Examples of inducible expression systems include zinc-inducible metallothionein promoters, tetracycline-inducible promoters and tetracycline-sensitive transcriptional repressors, RU 486-inducible promoters, ecdysone-inducible promoters and FK506 inducible promoters together with new rapamycin analogues.

The invention also provides a number of diagnostic and therapeutic methods and tools relating to disorders broadly characterized by decreased or absent TMS1 activity such as apoptotic induction activity. Such disorders can result from a decrease or an absence of TMS1 expression products, or a mutation in TMS1 nucleic acid molecules which thereby encode a mutant rather than wild-type TMS1 polypeptide. As used herein, a TMS1 expression product is meant to embrace TMS1 mRNA and TMS1 polypeptides. A particular subset of such disorders are characterized by, or associated with, an abnormal methylation of CpG island containing TMS1 nucleic acid molecules. CpG island containing TMS1 nucleic acid molecules are defined as those nucleic acid molecules inherently integrated in the genome of the subject. That is, CpG island containing TMS1 nucleic acid molecules represent the genomic TMS1 nucleic acid molecule. In some instances, the CpG island containing molecules also encode a TMS1 polypeptide. The CpG island region of TMS1 (i.e., SEQ ID NO:4) or fragments thereof could also be used to study methylation patterns apart from any coding region contained therein. Thus, the disorder is defined as the presence of a cell or a tissue which, compared to a normal cell population, exhibits increased methylation of the genomic locus of TMS1, decreased levels of TMS1 expression products and/or the presence of TMS1 nucleic acid or polypeptide mutants, including dominant negative mutants. As used throughout this specification, decreased levels, of for example expression, intend to encompass a complete absence of, or a reduction relative to normal. A subset of these disorders is defined as those in which the nucleotide sequence of SEQ ID NO:1, particularly the CpG island located at nucleotides 1100–1725, is methylated to a greater extent than that which is observed in normal tissue counterparts.

Thus, the invention seeks to diagnose and treat, prophylactically and/or therapeutically, disorders characterized by abnormal levels of TMS1 expression products or abnormal levels of methylation. Within an otherwise CpG-poor, heavily methylated genome, about one half of human genes are characterized by unmethylated, CpG-dense islands. (Bird, A. P., Nature 321, 209–213, 1986) A "normal" level, as used herein in reference to the level of TMS1 expression, TMS1 polypeptide, or TMS1 methylation, may be a level in a control population, which preferably includes subjects having similar characteristics as the treated individual, such as age and sex. The "normal" level can also be a range, for example, where a population is used to obtain a baseline range for a particular group into which the subject falls. Thus, the "normal" value can depend upon a particular population selected. Preferably, the normal levels are those of apparently healthy subjects who have no prior history of methylation- or TMS1-mediated disorders. More preferably, the normal level is that level in a tissue of a normal subject corresponding to the tissue sampled for the test subject. In other instances, the normal levels can also be determined by measuring expression, translation and/or methylation levels in a sample of normal tissue adjacent to the suspected diseased tissue in the subject. As an example, breast tumors are, in some cases, sufficiently delineated to the extent that such tissue can be distinguished from the surrounding normal breast tissue. This delineation facilitates selective removal of diseased breast tissue, such as occurs in non-radical mastectomies (e.g., lumpectomy). Similarly, such delineation can be used in the present invention to harvest both suspected diseased tissue and normal tissue from a given subject. Such normal levels, then can be established as preselected values, taking into account the category in which an individual falls. Appropriate ranges and categories can be selected with no more than routine experimentation by those of ordinary skill in the art. Either the mean or another preselected number within the range can be established as the normal preselected value.

Abnormally low levels of a TMS1 molecule are defined as levels lower than those observed in a control population itself defined as a normal as described herein. The control is preferably a tissue which corresponds to the tissue analyzed in the subject at risk or the subject having the disorder. Thus, as an example, if the subject is at risk of developing a breast tumor, then the control is preferably breast tissue from a normal subject, or more specifically levels of TMS1 molecules in breast tissue from normal subjects. The TMS1 molecules may be administered directly to a tissue, particularly one which is at risk of developing a tumor. By native TMS1 nucleic acid molecules is meant a subset of TMS1 nucleic acid molecules which are naturally occurring in a cell or tissue. Naturally occurring means those present or coded for in the genome of a cell which has not been the recipient of gene transfer by transfection, transformation, electroporation or any other gene transfer method known in the art.

Preferably, the disorder being diagnosed or treated is a proliferative disorder such as cancer. A cancer is defined as an uncontrolled, abnormal growth of cells, which can either remain localized or may disseminate throughout the body via the bloodstream or the lymphatic system, and thereby seed a secondary site (i.e., a metastasis). Diagnosis and treatment as used herein are directed to a cancer at its primary site and/or at a metastatic site. Examples of cancers to be diagnosed or treated include: biliary tract cancer; brain cancer, including glioblastomas and medulloblastomas; breast cancer; cervical cancer; choriocarcinoma; colon cancer; endometrial cancer; esophageal cancer; gastric cancer; hematological neoplasms, including acute lymphocytic and myelogenous leukemia; chronic lymphocytic and myelogenous leukemia, multiple myeloma; AIDS associated leukemias and adult T-cell leukemia lymphoma; intraepithelial neoplasms, including Bowen's disease and Paget's disease; liver cancer; lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; colorectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma teratomas and choriocarcinomas), stromal tumors and germ cell tumors; thyroid cancer, including thyroid adenocarcinoma and medullar carcinoma; and renal cancer including adenocarcinoma and Wilms' tumor. Preferably, the invention seeks to diagnose and treat breast cancer, cervical cancer, leukemia, ovarian cancer and prostate cancer. Even more preferably, the invention is directed at breast cancer.

In one aspect, the invention is directed to a method for identifying a subject at risk of developing a disorder, such as a tumor, characterized by methylation of a CpG island containing TMS1 nucleic acid molecule. The method involves determining a level of methylation of a CpG island containing TMS1 nucleic acid molecule and comparing such level of methylation to a control. The CpG island containing TMS1 nucleic acid molecule, in this embodiment, is selected from the group consisting of (a) nucleic acid molecules which hybridize under stringent conditions to a complement of a molecule consisting of SEQ ID NO:4 (i.e., nucleotides 1100–1725 of SEQ ID NO:1) and which code for a native TMS1 polypeptide, and (b) complements of (a). According to this method, an increase in the level of methylation of the CpG island containing TMS1 nucleic acid molecules in the biological sample compared to the control identifies a subject at risk of developing, for example, the tumor. Subjects having a disorder characterized by methylation of a CpG island containing TMS1 nucleic acid molecule can also be identified using a similar approach.

The level of methylation of a CpG island can be determined using a number of techniques available in the art. These include methylation-sensitive restriction analysis, methylation-specific polymerase chain reaction (MSP), sequencing of bisulfite-modified DNA, Ms-SnuPE, and COBRA.

Methylation-sensitive restriction analysis is derived from the existence in nature of restriction enzymes which are methylation sensitive (i.e., these enzymes do not recognize restriction sites which contain methylated residues). For example, the restriction enzyme NotI recognizes the sequence containing 2 'CG' dinucleotides. If either of the CG sites is methylated, the enzyme will not digest DNA. This fact has been heavily utilized in the analysis of DNA methylation in genomic DNA. In this approach, DNA is digested with a methylation-sensitive restriction enzyme and then electrophoresed on an agarose gel which separates DNA based on its size. The DNA is then transferred to a membrane and hybridized to a radiolabeled probe, as is routinely done in a Southern analysis. Based on the sizes of the bands which hybridize to the probe, the digested, and therefore unmethylated, DNA can be distinguished from the undigested, and therefore methylated, DNA. Other methylation-sensitive enzymes include SacI, EagI, SmaI, ThaI, HpaII, all of which are commercially available.

Another method useful for measuring methylation status of a nucleic acid is methylation specific PCR (i.e., MSP) which is disclosed in U.S. Pat. No. 5,786,146. This method is based on the differential reactivity of cytosine and 5-methylcytosine with sodium bisulfite. In the presence of sodium bisulfite, cytosines are deaminated to uracils and 5-methylcytosines remain as cytosines. Primers used to amplify such bisulfite treated nucleic acid molecules are able to hybridize specifically either to the 'unmethylated' or the 'methylated sequences. A multitude of parallel PCR reactions can be performed and analyzed on a gel simultaneously. Reaction vessels contain either methylation specific primers or primers specific for the unmethylated sequence, and thus an amplified product is formed only if the appropriate primers are present. It is preferred that two reactions are performed for each sample, one with methylation specific primers, and one with non-methylation specific primers. This technique allows the methylation status of virtually any CG dinucleotide to be known. Moreover, it requires minute amounts of DNA, on the order of nanograms or less. The nucleotide sequence of SEQ ID NO:1 can be used to design appropriate primers for use in this technique.

Genomic sequencing of bisulfite modified DNA is another method for determining methylation level of TMS1 genomic DNA. Like the methods described above, this method is also based on the differential reactivity of cytosine and 5-methylcytosine with sodium bisulfite. In this approach however, primers are designed to avoid potential methylation sites (e.g., CG dinucleotides) and a non-specific PCR is performed in order to amplify all alleles equally. Following amplification, the PCR product is sequenced directly, or can be subcloned into a plasmid and individual subclones sequenced. The sequence of amplified products is compared to that of non-bisulfite treated DNA. CG dinucleotides present in the non-bisulfite treated sample that read as TG as a result of bisulfite treatment were unmethylated in the original sample, while those which continue to read as CG even after bisulfite treatment were originally methylated. This approach is quantitative to the extent that it provides an absolute number of methylated residues in a particular nucleic acid sequence.

COBRA is a quantitative technique described by Xiong and Laird for determining DNA methylation levels at specific genetic loci in small amounts of genomic DNA. (Nucleic Acids Res 25:2532–4, 1997) The technique uses restriction enzyme digestion to reveal methylation-dependent sequence differences in PCR products of sodium bisulfite-treated DNA. Xiong and Laird reported that methylation levels in a original DNA sample are represented by the relative amounts of digested and undigested PCR product. This ratio has been shown to be linearly quantitative over a broad range of DNA methylation levels. The method has also been applied to DNA sample harvested from microdissected paraffin-embedded tissue samples, thus facilitating the analysis of tissue from a subject by eliminating the need for immediate processing of such samples.

Ms-SNuPE has been reported by Gonzalgo and Jones as a method for rapid quantitation of altered methylation patterns at specific sites, particularly CpG sites, in the genome. (Nucl. Acids Res. 25:2529–31, 1997) The approach relies on methylation sensitive single nucleotide primer extension and involves bisulfite treatment of DNA followed by single nucleotide primer extension. It does not involve restriction enzyme analysis. Briefly, genomic DNA is first reacted with sodium bisulfite to convert unmethylated cytosine to uracil without modification of 5-methylcytosine, as in other approaches described above. The bisulfite treated DNA is then amplified using PCR primers specific for bisulfite-converted DNA. The amplified product is then used as a template for methylation analysis at the CpG site(s) of interest. The method is amenable to the analysis of small amounts of DNA. Like MSP, bisulfite sequencing, COBRA and most all other PCR based strategies, Ms-SNuPE can be used in the analysis of microdissected pathology sections.

Cytosine methylation can also be measured using a approach which combines automated genomic DNA sequencing and GENESCAN analysis. This approach has been reported by Paul and Clark in Biotechniques 21:126–133, 1996. Similarly to the aforementioned approaches, this technique requires bisulfite treatment and PCR amplification of DNA. Cloning and sequencing of the modified and amplified products is then performed to determine the methylation of individual DNA molecules. The sequencing of the entire population of amplified products provides the average methylation status over the population, and thus may not be appropriate if the methylation status of individual molecules is desired. By employing fluorescence-based automated genomic sequencing, Paul and Clark were able to directly quantitate methylation status of any cytosine residue in a DNA molecule. The technique involves sequencing only cytosine and thymine residues of modified and amplified DNA and using fluorescent dyes to identify and visualize signals from these residues. GENESCAN analysis is then performed to estimate methylation at every cytosine in a rapid and accurate manner. The approach permits a rapid overview of DNA methylation profiles for a number of DNA molecules.

Yet another approach for quantitating genomic methylation was reported by McGrew and Rosenthal and involves the use of ligation-mediated PCR. (Biotechniques 15:722–9, 1993) This technique, like others described herein, is particularly suited to the measurement of CpG methylation. It involves the measurement of conversion of large genomic DNA fragments to shorter DNA fragments as a function of demethylation. The cleavage of large genomic DNA is accomplished using pairs of non-isoschizometic enzymes, one of which is methylation specific. The digestion products are then amplified with ligation-mediated, radiolabeled PCR, and used as a measure of cleavage with the methylation sensitive restriction enzyme. Specifically, the ratio of the two amplified fragments is related to the degree of methylation at the particular restriction site. Internal control of the amplification reaction confers the quantitative aspect of the approach.

The biological sample can be a tissue or a biological fluid. The term tissue as used herein refers to both localized and disseminated cell populations including brain, heart, serum, breast, colon, bladder, uterus, prostate, stomach, testis, ovary, pancreas, pituitary gland, adrenal gland, thyroid gland, salivary gland, mammary gland, kidney, liver, intestine, spleen, thymus, bone marrow, blood, trachea, and lung. In certain embodiments, test samples originate from colon, breast and prostate tissues. Biological fluids include saliva and urine, but are not so limited. In preferred embodiments, the tissue is breast tissue. Both invasive and non-invasive techniques can be used to obtain such samples and are well documented in the art.

As described herein, the level of methylation of a CpG island containing TMS1 nucleic acid molecule present in the biological sample is compared to a control. The control in some embodiments, is a normal tissue from a normal subject. In certain embodiments, the control is normal tissue from a subject having the disorder. As an example, the control may be normal breast tissue from a subject having breast cancer.

In another aspect, the invention provides a method for determining a risk of developing a disorder characterized by methylation of a CpG island containing TMS1 nucleic acid molecule. The method involves measuring a level of a TMS1 expression product (e.g., an expression product of a CpG island containing TMS1 nucleic acid molecule) in a biological sample by contacting the biological sample isolated from a subject with an agent that selectively binds to a TMS1 expression product. The TMS1 expression product can be a nucleic acid expression product which hybridizes under stringent conditions to a complement of a molecule comprising a nucleotide sequence of SEQ ID NO:2 or SEQ ID NO:24, for example, and which codes for a native TMS1 polypeptide. Such nucleic acid expression products include mRNA species and 2nd strand cDNA species synthesized from the mRNA. The TMS1 expression product can also be a polypeptide expression product, or a fragment thereof, of the TMS1 nucleic acid expression products. The level of interaction between the agent and the TMS1 expression product is determined and compared with a control. If the level of TMS1 nucleic acid expression products is being measured, such a determination can be carried out via any standard nucleic acid determination assay, including the polymerase chain reaction, or assaying with labeled hybridization probes, as in a Northern analysis. In these latter embodiments, the agent is preferably a nucleic acid molecule. If the level of TMS1 polypeptide expression products is being measured, such a determination can be carried out via any standard immunological assay using, for example, polyclonal or monoclonal antibodies or antisera which bind to the secreted TMS1 protein. In these latter embodiments, the agent is preferably a peptide, such as an antibody or antibody fragment, but it is not so limited. A decrease in the level of interaction between the agent and the target expression product in the biological sample compared to the control indicates a risk of developing the disorder.

A control can include a known amount of a nucleic acid probe or a TMS1 epitope (such as a TMS1 expression product). In preferred embodiments the control is a similar tissue sample from a subject with a control or 'normal' level of TMS1 expression, or with a control or normal level of methylation in the TMS1 locus.

It should be understood that the invention intends to embrace similar approaches for determining the risk of developing, or identifying subjects at risk of developing, a disorder characterized by abnormally low levels of TMS1 expression products.

Alternatively, the invention embraces a method of diagnosing in a subject a disorder characterized by the presence of a mutant TMS1 molecule. A TMS1 molecule as used herein includes a nucleic acid molecule and a polypeptide. Thus a mutant TMS1 molecule may be a mutant TMS1 nucleic acid molecule, which in turn encompasses both genomic and cDNA TMS1 nucleic acid molecules, or alternatively, it may be a mutant TMS1 polypeptide or a fragment thereof. The method involves (a) characterizing TMS1 molecules in a biological sample and (b) comparing the TMS1 molecules of the biological sample to TMS1 molecules of a control. An observed alteration or match, as the case may be, in a TMS1 molecule in the biological sample as compared to TMS1 molecules in the control, is indicative of a disorder characterized by the presence of a mutant TMS1 molecule. Preferably, the mutant TMS1 molecules are defined as those which account for a diminished or absent native TMS1 activity (e.g., apoptosis induction).

In some embodiments, the control may contain wild-type TMS1 molecules, while in others, it may contain mutant TMS1 molecules. By observed "alteration", it is meant that a TMS1 molecule in the biological sample is different from the normal TMS1 molecule contained in the normal control. Alternatively, an observed "match" occurs when the TMS1 molecule in the biological sample is identical to a mutant TMS1 sequence in a mutant control. Appropriate differences and/or matches in the sequences can be determined with no more than routine experimentation by those of ordinary skill in the art.

As used herein, a subject is a human, non-human primate, cow, horse, pig, sheep, goat, dog, cat or rodent. In all embodiments, human subjects are preferred, The invention provides various methods for the treatment of subjects having a variety of disorders. As used herein, the term "treat" encompasses both prophylactic and therapeutic treatment, and it embraces the prevention of disorders, inhibition and/or amelioration of pre-existing disorders. The subject may be at risk of developing a disorder, or alternatively, the subject may have such a disorder. Thus, a treatment may reduce or eliminate a disorder altogether or prevent it from becoming worse.

The invention provides prophylactic and therapeutic methods for increasing levels of TMS1 nucleic acid molecules and/or their expression products. Expression products as used herein is intended to embrace both transcriptional expression products (i.e., RNA species) and translational expression products (i.e., peptides and polypeptides).

The invention, in one aspect, embraces the treatment of subjects that express abnormal levels of TMS1 expression products in a tissue or a cell, preferably the tissue or cell suspected of having the disorder. Although not intending to be bound by any particular theory, it is postulated that down-modulation or absence of TMS1 polypeptides results in or predisposes a malignant phenotype to a cell. The abnormal levels of TMS1 expression products can be the result of, among other things, abnormal, preferably increased, methylation of the TMS1 genomic locus, and/or production of mutant rather than wild-type TMS1 expression products. Mutations to TMS1 nucleic acid molecules or polypeptides which prohibit normal functioning of the polypeptide can also serve to cause or predispose a malignant phenotype to a cell.

In one aspect, the invention provides a method for treating a subject having, or at risk of developing, a disorder characterized by abnormal methylation of a CpG island containing TMS1 nucleic acid molecule. According to the method, a subject at risk of developing is administered a demethylating agent in an amount effective to maintain a normal level of methylation in a CpG island containing TMS1 nucleic acid molecule in a tissue of the subject. In embodiments involving the treatment of subjects having the disorder, the effective amount is that amount required to reduce the level of methylation, preferably to normal or to below normal levels.

A demethylating agent is agent which directly or indirectly causes a reduction in the level of methylation of a nucleic acid molecule. Demethylating agents include inhibitors of methylating enzymes such as methylases and methyltransferases. Examples of demethylating agents useful in the invention include 5-azacytidine, 5-aza-2'deoxycytidine (also known as Decitabine in Europe), 5,6-dihydro-5-azacytidine, 5,6-dihydro-5-aza-2'deoxycytidine, 5-fluorocytidine, 5-fluoro-2'deoxycytidine, and short oligonucleotides containing 5-aza-2'deoxycytosine, 5,6-dihydro-5-aza-2'deoxycytosine, and 5-fluoro-2'deoxycytosine. All of the foregoing agents act as DNA methyltransferase inhibitors. Agents like these, such as the derivatives mentioned, are most effective if capable of being incorporated into a nucleic acid, preferably, DNA. Other agents reported to inhibit DNA methyltransferases and/or cause demethylation in vitro include procanamide and S-adenosyl homocysteine. Several candidate small molecule demethylating agents, including inhibitors of methyltransferase, which do not require nucleic acid incorporation to manifest their effects, are currently being developed.

Preferably, the demethylating agent is an agent which is inherently specific for a particular tissue or tumor type or alternatively, the agent is one which is modified in such a manner to achieve the desired specificity. These latter modifications may include the coupling of the agent to a cell-specific or tissue-specific targeting moiety, as described herein. In still a further embodiment, the demethylating agent may be coupled to a nucleic acid molecule which is specific for the TMS1 genomic locus. Such a targeting nucleic acid molecule can be a nucleic acid molecule which hybridizes under stringent conditions to a complement of a molecule consisting of SEQ ID NO:1, or it may be a complement of such a molecule.

The demethylating agent may be administered to a tissue at risk of developing or already having the disorder. In some important embodiments, the disorder is a cancer, such as tumor. Such tissues are preferably selected from breast tissue, prostate tissue, ovarian tissue, cervical tissue and bone marrow.

The prophylactic method may further comprise, in another embodiment, the selection of a subject at risk of developing a disorder prior to the administration of the demethylating agent. Such a subject may be identified using the diagnostic methods provided herein. Namely, a subject at risk may be one who exhibits an abnormal level of TMS1 expression products or one who exhibits an abnormal level of methylation in the TMS1 genomic locus. Preferably, subjects to be administered a demethylating agent are selected on the basis of an abnormal level of methylation in the TMS1 genomic locus. Other subjects at risk of developing such a disorder may be those with a family history of such disorders. As an example, subjects with a family history of breast cancer and/or abnormal TMS1 methylation may be considered subjects for prophylactic treatment regardless of whether the TMS1 genomic locus in the specific subject is methylated. Similarly, when used therapeutically, the method may also involve the prior selection of a subject having the disorder, either using the diagnostic methods described herein, or other procedures known in the art. For example, subjects intended to be treated according to the present invention include those diagnosed with breast cancer. This diagnosis may use the methods described herein, including the analysis of the level of methylation of TMS1 nucleic acid molecules or the level of TMS1 expression products. Alternatively, the subject may be diagnosed according to well known procedures such as mammography and cytological analysis following biopsy. Regardless of the form of diagnosis, the subject is intended to be treated for such a disorder according to the methods of the invention.

In another aspect, the invention provides a method for treating a subject having or at risk of developing, a disorder, perhaps in a tissue, characterized by abnormally low levels of a TMS1 expression product. If the subject has the disorder, the method involves administering to such a subject a demethylating agent in an amount effective to reduce the level of methylation in the TMS1 genomic locus (i.e., the CpG island containing TMS1 nucleic acid molecule) in a tissue (which has the disorder) of the subject. An effective amount of the demethylating agent may be defined as that amount necessary to reduce the level of methylation in the TMS1 genomic locus to below pre-treatment levels. In other embodiments, the effective amount may that amount necessary to reduce the level of methylation to a normal level of methylation. If the subject is at risk of having the disorder, the effective amount is that amount effective to maintain methylation levels in the TMS1 genomic locus at normal levels or to reduce the level of methylation to normal or below normal levels. An anticipated and measurable outcome of any suitable reduction in methylation of the TMS1 genomic locus is an increase in the level of TMS1 expression products as compared to pre-treatment levels.

In a further aspect, the invention also embraces a method for treating subjects expressing a mutant TMS1. These methods involve an initial determination of whether the subject, and in particular a specific tissue of the subject, expresses a wild-type or a mutant TMS1, and if wild-type is expressed, the level of its expression. As used herein, "wild-type" refers generally to a molecule which is ordinary, common, without defect or affect, and not mutant. An ordinary molecule, also refers generally to sequences or structures that, while they may vary from a canonical sequence or structure, comprise neutral polymorphisms and do not vary in function from a molecule having a non-mutant sequence or structure. According to the invention, a wild-type TMS1 is, for example, a nucleic acid molecule of SEQ ID NO:2 and its encoded wild-type polypeptide presented as SEQ ID NO:3. Another example of a wild-type TMS1 nucleic acid molecule is one having the nucleotide sequence of SEQ ID NO:24, and another wild-type TMS1 polypeptide is one having the amino acid sequence of SEQ ID NO:25. Wild-type TMS1 polypeptide (i.e., native TMS1 polypeptide) is capable of apoptosis induction, as described herein. Conversely, a "mutant" TMS1 typically has undergone a nucleic acid substitution that results in a non-conservative amino acid substitution at the polypeptide level that changes the functional characteristics of TMS1, thus rendering, for example, a proliferative or drug-resistant phenotype to the cell. In particular, TMS1 mutants may function as dominant negatives which interact, in a non-productive manner, with other TMS1 polypeptides or with other binding partners of wild-type TMS1, to prevent the normal functioning of TMS1 polypeptides. In other words, the dominant negative TMS1 mutants remove, or titrate out, functional wild-type TMS1 polypeptides or their wild-type binding partners, from the intracellular environment. The mutant TMS1 polypeptides may interfere with or inhibit normal TMS1 polypeptides and their naturally occurring binding partners (i.e., TMS1 ligands), and by doing so ultimately decrease the apoptotic capacity of a cell (i.e., the ability of a cell to undergo apoptosis in response to normally inducing apoptotic signals). An example of a mutant TMS1 molecule may be one having only exon 1 or exon 2 or one lacking exon 3.

The invention also intends to treat subjects having disorders characterized by expression of a mutant TMS1, or abnormally low levels of TMS1 expression products, or abnormal methylation level of a TMS1 nucleic acid, by administering an effective amount of a CARD-containing molecule to, preferably a tissue of the subject having the disorder. The effective amount is generally that amount, effective to increase the level of CARD-containing polypeptides in the affected tissue (or cells or cell population) of the subject. Methods directed at treating such subjects using CARD-containing molecules may also include the prior selection of a subject in need of such treatment (i.e., a subject having or at risk of developing a disorder characterized as above).

A CARD-containing molecule is a molecule that contains either the nucleotide sequence or the amino acid sequence of a CARD and is able to induce apoptosis in a manner similar to that of native TMS1 polypeptides, as described herein. The CARD-containing molecule includes both CARD-containing nucleic acid molecules and CARD-containing polypeptides. A CARD is found in exon 3 of SEQ ID NO:1 and SEQ ID NO:2 which code for TMS1 polypeptide. In particularly preferred embodiments, if the CARD molecule is a nucleic acid molecule it is one having a nucleotide sequence selected from the group consisting of SEQ ID NO:1, SEQ ID NO:2, SEQ ID NO:9, SEQ ID NO:20, SEQ ID NO:22 and SEQ ID NO:24, while if it is a polypeptide it is one having an amino acid sequence selected from the group consisting of SEQ ID NO:3, SEQ ID NO:10, SEQ ID NO:21, SEQ ID NO:23 and SEQ ID NO:25. Although it is preferred in some embodiments that the CARD-containing molecule be a TMS1 molecule, it is not so limited. A TMS1 molecule as used herein embraces TMS1 nucleic acid molecules (e.g., genomic, cDNA and mRNA species) and functional TMS1 peptides and polypeptides. The invention embraces the molecules described in this paragraph.

The TMS1 molecule may also be a TMS1 polypeptide. Preferably, the TMS1 molecule is a polypeptide which comprises SEQ ID NO:3. In other embodiments, the TMS1 nucleic acid molecule can be SEQ ID NO:20 or SEQ ID NO:22, and the TMS1 polypeptide can be SEQ ID NO:21 or SEQ ID NO:23. The invention also embraces fragments of TMS1 molecules that include a CARD. Such fragments may be of various lengths, as described previously herein.

Methods of the invention that embrace the use of CARD-containing or TMS1 nucleic acid molecules may be performed using embraces gene therapy. The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject which contains a defective copy of the gene, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy using vectors such as adenovirus, retroviruses, herpes virus, and targeted liposomes also is contemplated according to the invention.

In another aspect, the invention provides a method for treating a subject having a disorder characterized by abnormal cell proliferation. This aspect of the invention is premised, in part, on the unexpected finding that overexpression of a TMS1 nucleic acid molecule in a cell induces the cell to undergo apoptosis, regardless of whether the cell expresses TMS1 expression products prior to treatment. Thus, the method involves administering a TMS1 molecule to a tissue having the disorder in an amount effective to increase the level of TMS1 polypeptide to an above-normal level. The above-normal level may be at least 10%, at least 20%, at least 30%, at least 40%, at least 50%, at least 100%, at least 150%, at lest 200% or at least 300% above normal levels. Preferably, the level of TMS1 polypeptide is one which is sufficient to induce apoptosis of the cell in which it is expressed.

As used herein abnormal cell proliferation refers to a population of cells which exhibit an abnormal (e.g., increased) rate of division or an abnormal response or dependency on growth stimuli, as compared to their normal tissue counterparts. The population of cells may be localized (e.g., a tumor) or they may be disseminated (e.g., a leukemia). Disorders characterized by an abnormal cell proliferation, as used herein, include but are not limited to conditions involving solid tumor masses of benign, pre-malignant or malignant character. Although not wishing to be bound by a particular theory or mechanism, some of these solid tumor masses arise from at least one genetic mutation, some may display an increased rate of cellular proliferation as compared to the normal tissue counterpart, and still others may display factor independent cellular proliferation. Factor independent cellular proliferation is an example of a manifestation of loss of growth control signals which some, if not all, tumors or cancers undergo. The disorder need not be one characterized by abnormal methylation of a CpG island containing TMS1 nucleic acid molecule or by an abnormally low level of a TMS1 expression product, or by the presence of a mutant TMS1. Thus, the method may be used to treat a subject having a cancer which is not related to deregulation of the TMS1 genomic locus.

The TMS1 nucleic acid molecule useful in gene therapy may be selected from the group consisting of (a) nucleic acid molecules which hybridize under stringent conditions to a complement of a molecule comprising a nucleotide sequence of SEQ ID NO:2 or SEQ ID NO:24, for example, and which code for a functional TMS1 polypeptide, (b) deletions, additions and substitutions of (a) which code for a functional TMS1 polypeptide, (c) nucleic acid molecules that differ from the nucleic acid molecules of (a) or (b) in codon sequence due to the degeneracy of the genetic code, and (d) complements of (a), (b) or (c). In a preferred embodiment, the TMS1 nucleic acid molecule comprises SEQ ID NO:2 or SEQ ID NO:24. In a more preferred embodiment, the TMS1 nucleic acid molecule encodes a polypeptide, or a fragment of a polypeptide, comprising an amino acid sequence of SEQ ID NO:3, or SEQ ID NO:25.

In important embodiments, the gene therapy envisioned by the invention includes the use of TMS1 polypeptide encoding nucleic acid vectors which are regulated by tissue specific regulatory elements. Suitable vectors include adenovirus and retroviruses, both of which have been approved for human gene therapy trials. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W. H. Freeman C.O., New York (1990) and Murry, E. J. Ed. "Methods in Molecular Biology," vol. 7, Humana Press, Inc., Cliffton, N.J. (1991). Suitable promoters for expression in particular tissues are known in the art. Of particular interest are those which direct expression in breast tissue cells and these include estrogen receptor (ER) binding elements and whey acidic protein promoter elements. Alternatively, the promoter element may be one which is ubiquitously expressed (e.g., a promoter within the LTR of a retrovirus) and specificity of expression can be imparted by the selective delivery of the vector within the subject. Methods and compositions for specific targeting of tissues within a subject are described herein.

In another aspect, the invention relates to the administration of a CpG island containing TMS1 nucleic acid molecule to a subject at risk of developing such disorders. Preferably, the molecule comprises nucleotides 1100–1725 of SEQ ID NO:1 (i.e., SEQ ID NO:4). The purpose of administering a CpG island containing nucleic acid molecule to such a subject is to redirect, and in some instances saturate, the methylating activity which would otherwise be directed at the genomic TMS1 locus.

The invention is also useful in the generation of knock-out and/or transgenic non-human animals. As used herein, "knock-out non-human animals" include animals in which the endogenous TMS1 genomic locus has been mutated to an extent that it either can no longer be transcribed to produce mRNA, or any mRNA so produced does not lead to the production of wild-type TMS1 polypeptide. Such knock-outs are generally referred to as nulls, since neither wild-type nor mutant TMS1 polypeptides are detectably produced by the cells after mutation. Other "knock-out" animals embraced by the invention are those in which mutation and/or deletion of one or more coding regions within a genomic locus still results in the production of a protein species, albeit one which is mutant usually in the form of a truncation. This latter type of mutation, in some instances, results in the production of dominant negative forms of TMS1 polypeptide. Dominant negative forms of TMS1 polypeptides, as described herein, are mutants which still possess function, usually in the form of a negative function. An example of a dominant negative mutation is one which promotes the binding of mutant TMS1 polypeptide to its natural wild-type binding partners but prevents the natural disassociation of this interaction and/or prevents the wild-type binding partner from functioning as would normally under such association. Such animals are useful since they can simulate varying degrees of null mutations, based on the proportion of wild-type TMS1 polypeptides which exist in the cell unassociated with the dominant negative forms of the TMS1 polypeptide.

As used herein, "transgenic non-human animals" includes non-human animals having one or more exogenous nucleic acid molecules incorporated in germ line cells and/or somatic cells. Thus transgenic animals include "knockout" animals having a homozygous or heterozygous gene disruption by homologous recombination, animals having episomal or chromosomally incorporated expression vectors, etc. Knockout animals can be prepared by homologous recombination using embryonic stem cells as is well known in the art. The recombination may be facilitated using, for example, the cre/lox system or other recombinase systems known to one of ordinary skill in the art. In certain embodiments, the recombinase system itself is expressed conditionally, for example, in certain tissues or cell types, at certain embryonic or post-embryonic developmental stages, inducibly by the addition of a compound which increases or decreases expression, and the like. In general, the conditional expression vectors used in such systems use a variety of promoters which confer the desired gene expression pattern (e.g., temporal or spatial). Conditional promoters also can be operably linked to TMS1 nucleic acid molecules to increase expression of TMS1 in a regulated or conditional manner. Trans-acting negative regulators of TMS1 activity or expression also can be operably linked to a conditional promoter as described above. Such trans-acting regulators include antisense TMS1 nucleic acids molecules, nucleic acid molecules which encode dominant negative TMS1 molecules, ribozyme molecules specific for TMS1 nucleic acids, and the like. The transgenic non-human animals are useful in experiments directed toward testing biochemical or physiological effects of diagnostics or therapeutics for conditions characterized by increased or decreased TMS1 expression. Other uses will be apparent to one of ordinary skill in the art.

The agent of the invention can be administered with a disorder-specific therapy. As used herein, a disorder-specific therapy is a therapy, other than the administration of demethylating agents and/or TMS1 molecules of the invention, which has been reported to possess therapeutic effectiveness toward the disorder being treated. A disorder-specific therapy may include chemotherapy (i.e., treatment using chemical substances referred to herein as disorder-specific agents), as well as interventional therapies including surgery and radiation, but is not so limited. In some embodiments, the demethylating agents or TMS1 molecules may be administered substantially simultaneously with the disorder-specific therapy including the disorder-specific agents. By substantially simultaneously, it is meant that a demethylating agent or TMS1 molecule of the invention is administered to a subject close enough in time with the administration of , for example, the disorder-specific agent so that the two compounds may exert an additive or even synergistic effect, (e.g., reducing a tumor mass).

According to other embodiments, the agents of the invention may be administered prior to, concurrent with, or following the disorder-specific therapy, although in some embodiments it is preferred that the agents of the invention (i.e., the demethylating agents or the TMS1 molecules) be administered prior to or concurrently with the disorder-specific therapy. The administration schedule may involve administering the different agents in an alternating fashion. In other embodiments, the agent may be delivered before and during, or during and after, or before and after treatment with other therapies. In some cases, the agent is administered more than 24 hours before the administration of the other therapy.

One important category of disorder-specific therapy is that intended for proliferative disorders such as cancer. Thus, in some important embodiments relating to the treatment of subjects who have cancer including both solid mass cancer ((e.g., tumors) and non-solid mass cancers (e.g., leukemia), the subject may be administered an agent of the invention and an anti-cancer therapy. As used herein, an anti-cancer therapy is a therapeutic regimen which is intended to inhibit or stabilize the growth of a primary cancer or tumor and/or prevent the growth of a secondary cancer or tumor such as a metastatic lesion. Anti-cancer therapy embraces a number of therapies including but not limited to radiation therapy and chemotherapy (i.e., chemical mediated therapy). In certain embodiments, the anti-cancer therapy may include more than one therapy (e.g., radiation and chemotherapy both administered to the subject). Thus, as an example, the subject may receive the agents of the invention, in combination with both radiation and at least one chemotherapeutic agent. Alternatively, the agent may be administered in combination with more than one chemotherapeutic agent.

The invention provides in another aspect a method for treating a subject having a cancer which involves administering an agent of the invention (i.e., a demethylating agent or a TMS1 molecule) and an anti-cancer therapy to a subject in need of such treatment in a combined amount effective to treat the cancer. Preferably, the cancer is selected from the group consisting of a cancer characterized by abnormal methylation of a CpG island containing TMS1 nucleic acid molecule, and a cancer characterized by an abnormally low level of a TMS1 expression product, or a cancer characterized by the expression or presence of a mutant TMS1 molecule. In one aspect, the agent of the invention and the anti-cancer therapy are administered in a manner that allows for a synergistic response. As used herein, a synergistic response is one in which the combined administration of the two or more agents or therapies yield a result that is greater than the additive effects of either of the agents or therapies alone. In some instances, one or both the agent of the invention and the anti-cancer therapy may be administered in a sub-therapeutic dose. A sub-therapeutic dose is one which alone would not result in a therapeutic benefit to the subject but which may be combined with another agent in order to effectuate therapeutic benefit. The agent of the invention may be administered prior to or concurrently with the anti-cancer therapy.

In another aspect, the agent of the invention is administered prior to or concurrently with an anti-cancer therapy, in an amount effective to sensitize the cancer to the anti-cancer therapy. An amount of agent that sensitizes a cancer means that amount that renders the cancer (which would be non-responsive otherwise) responsive to anti-cancer therapy. In some instances, the amount of demethylating agent which is effective to sensitize a cancer may be less than that amount effective to restore or maintain a normal level of methylation in a CpG island containing TMS1 nucleic acid molecule. Thus, according to the invention it is possible to treat a disorder such as a cancer that is characterized by abnormal methylation of a TMS1 nucleic acid molecule either by the use of a demethylating agent alone, or with a demethylating agent coupled with an anti-cancer therapy. It is conceivable that when used alone, a higher dose of a demethylating agent may be required to effect a beneficial outcome in the subject. Similarly, in some instances, the combined use of a demethylating agent and an anti-cancer therapy is expected to require a lower dose of the anti-cancer therapy for a beneficial outcome. This latter result is desirable given the side-effects of most anti-cancer therapies. It is to be understood that the invention provides similar methods of treatment of subjects having cancer using CARD-containing molecules, and preferably TMS1 molecules, and an anti-cancer therapy.

One common therapy for subjects diagnosed with cancer is administration of chemotherapy or exposure to radiation, for the purpose of inducing DNA damage and ultimately apoptosis of cancer cells so treated. The ability of cancer cells with DNA damage to recognize this apoptotic signal and to undergo apoptosis is dependent upon the presence of caspase-9, a pro-apoptotic factor. However, a frequent occurrence in the treatment of some, if not all, forms of cancer is their ability to become resistant to chemotherapy during or following treatment, as well as the non-responsiveness of some subjects even prior to treatment. As described in the Examples, it was unexpectedly found according to the invention that the ability of TMS1 to induce apoptosis is dependent upon caspase-9. Furthermore, it was found that TMS1 is an upstream factor of the caspase-9 dependent apoptosis pathway. These findings indicate that TMS1 can be a controlling factor in determining whether a subject is capable of undergoing apoptosis in response to particular forms of anti-cancer therapy.

Accordingly, in yet a further aspect, the invention provides methods for identifying a subject who is at risk of being non-responsive to a particular disorder-specific therapy. Preferably, the subject has the particular disorder which is sought to be treated with the therapy. As an example, the subject may be one who has been diagnosed with cancer using standard diagnostic procedures known in the art. Generally such a subject may be administered conventional (e.g., DNA damaging) anti-cancer therapy such as radiation therapy and some forms of chemotherapy. It is well known however that some patients so treated with radiation therapy, and more commonly some forms of chemotherapy, become unresponsive (i.e., refractory) to the therapeutic regimen. The ability to identify subjects likely to be non-responsive to particular forms of anti-cancer therapy would be useful since it would prevent the unnecessary administration of the particular anti-cancer therapy and would increase the likelihood that the subject would be administered a therapeutically effective therapy. In a similar manner, the invention provides a method for individually tailoring a therapeutic regimen for a particular subject.

Subjects at risk of being non-responsive to a particular anti-cancer therapy are identified, according to the invention, in a number of ways. In one instance, the subject is identified by analyzing the methylation of a TMS1 nucleic acid molecule. Briefly, the method involves determining the level of methylation of a CpG island containing TMS1 nucleic acid molecule in a biological sample from a subject having cancer and comparing the level of methylation with a control. An increase in the level of methylation in the biological sample from the subject having cancer when compared to the control is indicative of a subject who is at risk of being non-responsive to an anti-cancer therapy. The level of methylation may be measured according to any of the appropriate methods described herein. In another instance, a non-responsive subject is identified by measuring the level of a TMS1 expression product in a biological sample from the subject having cancer. In both methods, the biological sample is of a tissue or a cell or a cell population in which the disorder exists. The control may be normal tissue from a normal subject, or alternatively it may be normal tissue from the subject having cancer. In some preferred embodiments, the control is normal tissue taken from the same tissue in which the disorder exists (e.g., normal breast tissue from a subject with breast cancer). Subjects identified in this manner can subsequently be administered an agent of the invention (e.g., a demethylating agent or a TMS1 molecule) in an amount effective to ultimately increase the level of TMS1 expression products, most preferably TMS1 polypeptides.

In one embodiment, it is envisioned that subjects who are diagnosed as described herein as having abnormal methylation at the TMS1 locus, or who have an abnormally low level of TMS1 expression products, or who express mutant forms of TMS1, are more likely to be resistant to anti-cancer therapies which require apoptosis to be effective (e.g., DNA damaging treatment regimens). Thus, subjects so identified may be more preferably treated with forms of anti-cancer therapy which are not wholly dependent upon apoptosis (e.g., those that are not primarily DNA damaging agents). Such anti-cancer therapies may include biological response modifying therapy, hormonal therapies, immunomodulating therapies (e.g., immunotherapeutic agents and cancer vaccines), angiogenesis inhibitors, metalloproteinase inhibitors and the like.

DNA damaging anti-cancer therapies include topoisomerase inhibitors (e.g., etoposide, ramptothecin, topotecan, teniposide, mitoxantrone), anti-microtubule agents (e.g., vincristine, vinblastine), anti-metabolic agents (e.g., cytarabine, methotrexate, hydroxyurea, 5-fluorouracil, floxuridine, 6-thioguanine, 6-mercaptopurine, fludarabine, pentostatin, chlorodeoxyadenosine), DNA alkylating agents (e.g., cisplatin, mechlorethamine, cyclophosphamide, ifosfamide, melphalan, chorambucil, busulfan, thiotepa, carmustine, lomustine, carboplatin, dacarbazine, procarbazine), DNA strand break inducing agents (e.g., bleomycin, doxorubicin, daunorubicin, idarubicin, mitomycin C), and radiation therapy.

Immunotherapeutic agents which may be administered to such subjects include Ributaxin, Herceptin (trastuzumab), Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV 103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART 1D10 Ab, SMART ABL 364 Ab, ImmuRAIT-CEA, immunostimulant peptides, oligonucleotides,.

Cancer vaccines may be selected from the group consisting of EGF, Anti-idiotypic cancer vaccines, Gp75 antigen, GMK melanoma vaccine, MGV ganglioside conjugate vaccine, Her2/neu, Ovarex, M-Vax, O-Vax, L-Vax, STn-KHL theratope, BLP25 (MUC-1), liposomal idiotypic vaccine, Melacine, peptide antigen vaccines, toxin/antigen vaccines, MVA-based vaccine, PACIS, BCG vaccine, TA-HPV, TA-CIN, DISC-virus and ImmuCyst/TheraCys.

Biological response modifiers include cytokines such as interferon, interleukins and lymphokines (e.g., IL-2), interferon agonists, hemopoietic growth factors (e.g., erythropoietin, GM-CSF, G-CSF), bFGF inhibitor, insulin-like growth factor-1 receptor inhibitor.

Hormone therapy includes adrenocorticosteriods (e.g., prednisone, methylprednisolone, dexamethasone), androgens (e.g., fluoxymesterone), anti-androgens (e.g., flutamide), estrogens (e.g., diethylstilbestrol, ethinyl estradiol), anti-estrogens (e.g., tamoxifen), progestins (e.g., medroxyprogesterone, megestrol acetate), aromatase (aminoglutethimide), gonadotropin-releasing hormone agonists (e.g., leuprolide), somatostatin analogues (e.g., octreotide).

Angiogenesis inhibitors include basic FGF, VEGF, angiopoietins, angiostatin, endostatin, TNFα, TNP-470, thrombospondin-1, platelet factor 4, CAI, and certain members of the integrin family of proteins.

In a related aspect of the foregoing method, the subjects identified as being at risk of being non-responsive to a disorder-specific therapy may be treated by administering an agent of the invention (e.g., a demethylating agent or a TMS1 molecule) and disorder-specific therapy. The agent of the invention may be administered substantially simultaneously with the disorder-specific therapy or alternatively, the agent may be administered prior to the administration of the disorder-specific therapy. In one important embodiment, the disorder-specific therapy (e.g., an anti-cancer therapy) is administered with a demethylating agent and not a TMS1 molecule. In these embodiments, the anti-cancer therapy may be DNA damaging anti-cancer therapy or not. The intention is these latter embodiments is to make cancers sensitive to the anti-cancer therapy but increasing the level of TMS1 expression products in the tissue (preferably the malignant tissue) of the subject.

One category of anti-cancer therapy is chemotherapy. Examples of chemotherapeutic agents include Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine;

Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Iproplatin; Irinotecan Hydrochloride; Lanreotide Acetate; Letrozole; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Tecogalan Sodium; Tegafur; Teloxantrone Hydrochloride; Taxotere; Temoporfin; Teniposide; Teroxirone; Testolactone; Thiamiprine; Thioguanine; Thiotepa; Tiazofurin; Tirapazamine; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Other chemotherapies include methotrexate, vincristine, adriamycin, cisplatin, non-sugar containing chloroethylnitrosoureas, mitomycin C, dacarbazine, fragyline, Meglamine GLA, valrubicin, carmustaine and poliferposan, MMI1270, BAY 12–9566, RAS famesyl transferase inhibitor, famesyl transferase inhibitor, MMP, MTA/LY231514, LY264618/Lometexol, Glamolec, CI-994, TNP-470, PKC412, Valspodar/PSC833, Novantrone/Mitroxantrone, Metaret/Suramin, Batimastat, E7070, BCH-4556, CS-682, 9-AC, AG3340, AG3433, IncelNX-710, VX-853, ZDO101, ISI1641, ODN 698, TA 2516/Marmistat, BB2516/Marmistat, CDP 845, D2163, PD183805, DX895 If, Lemonal DP 2202, FK. 317, Picibanil/OK-432, AD 32Nalrubicin, Metastron/strontium derivative, Temodal/Temozolomide, Evacet/liposomal doxorubicin, Xeload/Capecitabine, Furtulon/Doxifluridine, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT(Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, Iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, nitrosoureas, alkylating agents such as melphelan, cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Floxuridine, Flutamide, Hydroxyurea (hydroxycarbamide), Ifosfamide, Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Thioguanine, Thiotepa, Vinblastine sulfate, Amsacrine (m-AMSA), Azacitidine, Hexamethylmelamine (HMM), Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate.

Other chemotherapeutic agents include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; antagonist D; antagonist G; antarelix; anti-dorsalizing morphogenetic protein-1; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat;

imidazoacridones; imiquimod; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anti cancer compound; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; $O^6$-benzylguanine; octreotide; okicenone; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

Another anti-cancer therapy that can be used with the agents of the invention include anti-cancer supplementary potentiating chemotherapeutic agents. Examples include Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{++}$ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and multiple drug resistance reducing compounds such as Cremaphor EL.

Other compounds which are useful in combination therapy of the invention include Piritrexim Isethionate; the antiprostatic hypertrophy compound, Sitogluside; the benign prostatic hyperplasia therapy compound, Tamsulosin Hydrochloride; the prostate growth inhibitor, Pentomone; radioactive compounds such as Fibrinogen 1 125, Fludeoxyglucose F 18, Fluorodopa F 18, Insulin I 125, Insulin I 131, Iobenguane I 123, Iodipamide Sodium I 131, Iodoantipyrine I 131, Iodocholesterol I 131, Iodohippurate Sodium I 123, Iodohippurate Sodium I 125, Iodohippurate Sodium I 131, Iodopyracet I 125, Iodopyracet I 131, Iofetamine Hydrochloride 1 123, Iomethin I 125, Iomethin I 131, Iothalamate Sodium I 125, Iothalamate Sodium I 131, Iotyrosine I 131, Liothyronine I 125, Liothyronine I 131, Merisoprol Acetate Hg 197, Merisoprol Acetate Hg 203, Merisoprol Hg 197, Selenomethionine Se 75, Technetium Tc 99m Antimony Trisulfide Colloid, Technetium Tc 99m Bicisate, Technetium Tc 99m Disofenin, Technetium Tc 99m Etidronate, Technetium Tc 99m Exametazime, Technetium Tc 99m Furifosmin, Technetium Tc 99m Gluceptate, Technetium Tc 99m Lidofenin, Technetium Tc 99m Mebrofenin, Technetium Tc 99m Medronate, Technetium Tc 99m Medronate Disodium, Technetium Tc 99m Mertiatide, Technetium Tc 99m Oxidronate, Technetium Tc 99m Pentetate, Technetium Tc 99m Pentetate Calcium Trisodium, Technetium Tc 99m Sestamibi, Technetium Tc 99m Siboroxime, Technetium Tc 99m Succimer, Technetium Tc 99m Sulfur Colloid, Technetium Tc 99m Teboroxime, Technetium Tc 99m Tetrofosmin, Technetium Tc 99m Tiatide, Thyroxine I 125, Thyroxine I 131, Tolpovidone I 131,Triolein I 125 and Triolein I 131.

The invention further embraces pharmaceutical preparations or compositions useful for treating subjects having or at risk of having the disorders described herein. In one aspect of the invention, a pharmaceutical preparation comprising a demethylating agent and a pharmaceutically acceptable carrier is provided. It is to be understood that one or more different demethylating agents may be present in a given pharmaceutical preparation. In another aspect, the pharmaceutical preparation comprising a TMS1 molecule and a pharmaceutically acceptable carrier is provided. The pharmaceutical preparation may contain one or more different forms of TMS1 molecules. In yet another aspect, the invention provides a pharmaceutical preparation comprising both demethylating agents and TMS1 molecules along with a pharmaceutically acceptable carrier. Each and every pharmaceutical preparation described herein may also optionally contain one or more disorder-specific therapeutic agents, as described herein.

The invention further provides a medicament and a method of making a medicament. The medicament comprises an agent and a pharmaceutically acceptable carrier. The method involves placing an agent in a pharmaceutically acceptable carrier. The agent may be a demethylating agent or a TMS1 molecule. Alternatively, the medicament may contain both a demethylating agent and a TMS1 molecule. Optionally, any of the foregoing medicaments may also contain a disorder-specific agent, other than the demethylating agents and the TMS1 molecules of the invention. In one embodiment, the medicament is formulated in a dose and/or a delivery formulation particularly tailored to the treatment of breast cancer.

The pharmaceutical preparations, as described above, are administered in effective amounts.

The effective amount will depend upon the mode of administration, the particular condition being treated and the desired outcome. It will also depend upon, as discussed above, the stage of the condition, the age and physical condition of the subject, the nature of concurrent therapy, if any, and like factors well known to the medical practitioner. For therapeutic applications, it is that amount sufficient to achieve a medically desirable result. In some cases this is a decrease in cell proliferation or an increase in apoptosis induction.

Generally, doses of active compounds of the present invention would be from about 0.0001 mg/kg per day to 1000 mg/kg per day. It is expected that doses ranging from 50–500 mg/kg will be suitable. A variety of administration routes are available. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule. When peptides are used therapeutically, in certain embodiments a desirable route of administration is by pulmonary aerosol. Techniques for preparing aerosol delivery systems containing peptides are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences*, 18th edition, 1990, pp 1694–1712; incorporated by reference). Those of skill in the art can readily determine the various parameters and conditions for producing antibody or peptide aerosols without resort to undue experimentation.

The mode of administration and dosage of the agent will vary with the particular stage of the condition being treated, the age and physical condition of the subject being treated, the duration of the treatment, the nature of the concurrent therapy (if any), the specific route of administration, and the like factors within the knowledge and expertise of the health practitioner.

Compositions suitable for oral administration may be presented as discrete units, such as capsules, tablets, lozenges, in both immediate release or controlled release formulations, each containing a predetermined amount of the active agent,. Other compositions include suspensions in aqueous liquids or non-aqueous liquids such as a syrup, elixir or an emulsion.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

The TMS1 molecules including but not limited to polypeptides or fragments thereof may be combined, optionally, with a pharmaceutically-acceptable carrier. The term "pharmaceutically-acceptable carrier" as used herein means one or more compatible solid or liquid filler, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Various techniques may be employed for introducing nucleic acids of the invention into cells, depending on whether the nucleic acids are introduced in vitro or in vivo in a host. Such techniques include transfection of nucleic acid-CaPO$_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

Other delivery systems can include time-release, delayed release or sustained release delivery systems. Such systems can avoid repeated administrations of the anti-inflammatory agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides and non-polymer systems such as melted and recrystallized sterols including cholesterol. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. No. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

In still other embodiments, the agent of the invention (e.g., the demethylating agent or the TMS1 molecule) is targeted to a cell, a cell population or a tissue that has, or is at risk of having (i.e., developing), the disorder sought to be prevented or treated through the use of a targeting compound specific for a particular cell or tissue. As an example, if the tissue has developed a tumor, the targeting compound may be specific for the tumor type. The agents of the invention may be targeted to primary or in some instances, secondary (i.e., metastatic) lesions through the use of targeting compounds which preferentially recognize a cell surface marker. The targeting compound may be directly conjugated to the agents of the invention via a covalent linkage. The agent may be indirectly conjugated to a targeting compound via a linker. Alternatively, the targeting compound may be conjugated or associated with an intermediary compound such as, for example, a liposome within which the agent is encapsulated. Liposomes are artificial membrane vessels which are useful as a delivery vector in vivo or in vitro. It has been shown that large unilamellar vessels (LUV), which range in size from 0.2–4.0 µm can encapsulate large macromolecules. Liposomes may be targeted to a particular tissue, such as the vascular cell wall, by coupling the liposome to a specific ligand such as a monoclonal antibody, sugar, glycolipid, or protein. Liposomes are commercially available from Gibco BRL, for example, as LIPOFECTIN™ and LIPOFECTACE™, which are formed of cationic lipids such as N-[1-(2,3 dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in *Trends in Biotechnology*, V. 3, p. 235–241 (1985). In still other embodiments, the targeting compound may be loosely associated with the agents of the invention, such as within a microparticle comprising a polymer, the agent of the invention and the targeting compound.

Targeting compounds useful according to the methods of the invention are those which direct the agent to a site having a disorder or at risk of developing a disorder such as a tumor site. The targeting compound of choice will depend upon the nature of the tumor or the tissue origin of the metastasis. In some instances it may be desirable to target the agent to the tissue in which the tumor is located. For example, agents can be delivered to breast epithelium by using a targeting compound specific for breast tissue. In preferred embodiments, the target is specific for malignant breast epithelium. Examples of compounds which may localize to malignant breast epithelium include, but are not limited to, estrogen and progesterone, epithelial growth factor (EGF) and HER-2/neu ligand, among others. The HER-2/neu ligand may also be used to target agents to ovarian cancers. Ovarian cancers are also known to express EGFR and c-fms, and thus could be targeted through the use of ligands for either receptor. In the case of c-fms which is also expressed by macrophages and monocytes, targeted delivery to an ovarian cancer may require a combination of local administration such as a vaginal suppository as well as a targeting compound. Prostate cancers can be targeted using compounds such as peptides (e.g., antibodies or antibody fragments) which bind to prostate specific antigen (PSA) or prostate specific membrane antigen (PSMA). Other markers which may be used for targeting of the agent to specific tissues include, for example, in liver: HGF, insulin-like growth factor I, II, insulin, OV-6, HEA-125, hyaluronic acid, collagen, N-terminal propeptide of collagen type III, mannose/N-acetylglucosamine, asialoglycoprotein, tissue plasminogen activator, low density lipoprotein, carcinoembryonic antigen; in kidney cells: angiotensin II, vasopressin, antibodies to CD44v6; in keratinocytes and skin fibroblasts: KGF, very low density lipoprotein, RGD-containing peptides, collagen, laminin; in melanocytes: kit ligand; in gut: cobalamin-intrinsic factor, heat stable enterotoxin of *E. Coli*; in breast epithelium: heregulin, prolactin, transferrin, cadherin-11. Other markers specific to particular tissues are available and would be known to one of ordinary skill in the art.

In still other embodiments, the agent of the invention may be targeted to fibroblasts, via ligands or binding partners for fibroblast specific markers. Examples of these markers include, but are not limited to fibroblast growth factors (FGF) and platelet derived growth factor (PDGF).

TABLE I

Sequences with partial homologies to TMS1

Sequences with GenBank and EMBL (*) accession numbers:

SEQ ID NO: 1

AW009953.1, AI991236.1,
AL023575.1, AC005588, AL022313, AC003080, AC003043, AC006023.2, AL031055, AC003009,
AC002449, AL021807.1,
AA516955, AA516629, W64166, AA517646, AI326216, AI503861, AI616330.1, AA823826, AA036192,
AI923691.1, R48326, AI148558, AI262374, AI346818, AW009953.1, AI991236.1, AA278825, AI650407.1,
AI879821.1, AA582937, AA573948, AA528254, AA568456, AA441911, AI277160, AA148254, AI368975,
AA148255, AA928164, W17108, AA442018, AA769741, H16108, AI675866.1, AI910530.1, AI024901,
AA282250, T25032, AA278827,
AI066909, AI145414.1,
A58551.1, A43445.1, A51134.1, AR020909, I25678
AX017270 NM_013258, AK000211, AB023416, AF255794, AF086332,
AI923691, R48326, AI148558, AI262374, AI346818, BE908204, AW337649, BE906296, AW009953,
AI991236, AW973297, AW292443, AA278825, BE909218, AI650407, AI879821, AA582937, AA573948,
AA528254, AA568456, AA441911, AI277160, AA148254, BE560228, AI368975, AW770914, AA148255,
AA928164, BE560247, W17108, AA442018, AA769741, H16108, AI675866, AW799740, AI910530,
BE170951, AI024901, AA282250, T25032, AA278827, BE071843, W73558, AW059668
AA036192, W78666, AA015254, AA616380, AA050695, W13611, AA266479, AA047994,

SEQ ID NO: 2

AF086332,
AW009953.1, AI991236.1,
AA036192, AA266479, AA015254, W78666, AA616380, AA050695, AA047994, W13611,
AI148558, AA528254, AA582937, AA573948, AA278825, AI262374, AA148254, AI346818, AW009953.1,
AA148255, AI991236.1, AI879821.1, AA568456, AA441911, AI277160, AI368975, AA928164, W17108,
AI024901, AA442018, AA769741, H16108, AI675866.1, AI910530.1, AA282250, T25032, AA278827,
AI237542, AA944962, AA851245, AI071267.1, AI411217, AB016922.1,
E15920.1, I09517, I07886, E08092, A08832.1, E15921.1, I40161, I91798, A00196.1, A06986.1, A06987.1,
I61404, I34189,
E05044, AR005279, A42329.1

SEQ ID N0: 24:

NM_013258.1, AX017270.1, AK000211.1, AB023416.1, AF086332.1,
BE906296.1, AX017270.1, BE908204.1, BE909218.1, BE753025.1,
AI991236.1, BE906296.1, AI346818.1, AW009953.1, AI262374.1, AI148558.1, BE908204.1, AW337649.1,
AW973297.1, AW292443.1, AA278825.1, BE909218.1, AI879821.1, AA582937.1, AA573948.1,
AA528254.1, AA568456.1, AA441911.1, AI277160.1, AA148254.1, BE560228.1, AI368975.1,
AW770914.1, AA928164.1, AA148255.1, AA769741.1, W17108.1, AA442018.1, H16108.1, AI675866.1,
AW799740.1, AI910530.1, BE560247.1, BE170951.1, AI024901.1, AA282250.1, T25032.1, AV664060.1,
AW479270.1, AA278827.1, BE071843.1, AV664059.1, BE753025.1,
G33295.1, G28555.1, AL146304.1, D25453.1, G27934.1, G19810.1, L18488.1, G57929.1, G53082.1,
G50720.1, G18374.1, AL156359.1, AL1S1001.1, AL149657.1, AL147151.1, AL146079.1, AL144969.1,
AL141138.1, G34804.1, G11610.1, G10503.1, AB044684.1, Z30389.1, Z70868.1
AA036192.1, BE860311.1, BE627788.1, AW323711.1, AA616380.1, AA266479.1, AA050695.1,
AA047994.1, AA015254.1, W78666.1, W13611.1,
AI991236.1, BE906296.1, AI346818.1, AW009953.1, AI262374.1, AI148558.1, BE908204.1, AW337649.1,
AW973297.1, AW292443.1, AA278825.1, BE909218.1, AI879821.1, AA582937.1, AA573948.1,
AA528254.1, AA568456.1, AA441911.1, AI277160.1, AA148254.1, BE560228.1, AI368975.1,
AW770914.1, AA928164.1, AA148255.1, AA769741.1, W17108.1, AA442018.1, H16108.1, AI675866.1,
AW799740.1, AI910530.1, BE560247.1, BE170951.1, AI024901.1, AA282250.1, T25032.1, AA278827.1,
BE071843.1,
AV664060.1, AW479270.1, AV664059.1, BE753025.1,
AR036571.1, AR076110.1, AR070492.1, AR070491.1, AR031690.1, I91798.1, I81460.1, I73184.1,
AQ374921.1, AQ667847.1, AQ440094.1,
AC009088.5,

EXAMPLES

Example 1

Methods and Materials

Cell Lines:

IMR90 normal human diploid fibroblasts and SV40 immortalized IMR90 cells (called here '90SV') were obtained from the National Institute on Aging Cell Repository and were maintained in EMEM containing 2 mM glutamine and 10% FCS. The isolation and maintenance of 90SV derivative cell lines stably overexpressing human DNMT1 (HMT.IEI) has been reported. (Vertino, P. M. et al., Mol.Cell Biol. 16:4555–4565, 1996) HMT.1E1, expresses 50-fold increased levels of human DNA methyltransferase relative to the parental 90SV fibroblasts. HMT.1E1 cells were maintained in EMEM plus 2mM glutamine, 10% fetal calf serum and 400 µg/ml G418 (Life Technologies). The human breast epithelial cell line MCF10A was obtained from the Karmanos Cancer Institute, Detroit, Mich., and were maintained in DMEM/F12 plus 5% fetal calf serum, 20 ng/ml epidermal growth factor, 0.5 µg/ml hydrocortisone, 100 ng/ml cholera toxin, 10 µg/ml insulin and 2 mM glutamine. Other human breast cell lines and 293 human embryonic kidney cells were obtained from the American Type Culture Collection (Manassas, Va.) and were maintained in DMEM (4.5 g/l glucose) plus 10% fetal calf serum and 2 mM glutamine. For Hs578Bst, Hs578t, MCF7, MDA MB435 and T47D cells, medium was supplemented with 10 µg/ml insulin. Passage seven HMEC primary breast epithelial cells were obtained from Clonetics (Walkersville, Md.) and were cultured according to the recommendations of the supplier. SKBR3 cells were maintained in McCoys 5A medium plus 10% fetal calf serum and 2 mM glutamine. All cells were maintained at 37° C. and 5% $CO_2$.

DNA isolated from primary breast tissues and tumors was generously provided by Dr. Sara Sukumar (Johns Hopkins University). Primary breast tissue from reduction mammoplasties or from breast tumors was obtained immediately following surgical resection at Johns Hopkins University Hospital or Duke University and frozen at −80° C. Tumors were estimated to contain at least 50% tumor cells by microscopic examination of representative tissue sections.

Representational Difference Analysis:

Total RNA was isolated from 90SV cells at PD 144 and HMT.1E1 cells at passage 10 by lysis in guanidinium isothiocyanate followed by acid/phenol extraction and isopropanol precipitation. Poly (A)+ RNA was selected on oligo-dT cellulose and used to synthesize double-stranded cDNA using the cDNA CHOICE system (Life Technologies) and a modified oligo-dT primer according to the manufacturer's recommendations. Double stranded cDNA was digested with DpnI, ligated to linkers, and amplified by PCR using linker-specific primers to generate the tester (90SV) and driver (HMT.1E1) amplicons. The cDNA pools were then subjected to representational difference analysis as described. (Hubank, M. et al., Nucleic Acid Res. 22:5640–5648, 1994) Three rounds of subtraction and amplification of tester-only sequences were performed using ester-to-driver ratios of 1:80, 1:400, and 1:80, 000. After three rounds, a predominant 350 bp difference product was isolated, digested with DpnI and subcloned into the BamHI site of pBluescript SK+. Plasmid subdones were screened for differential representation by hybridization to Southern blots of the starting tester and driver amplicons. One of these subclones (RDA 2.15) was selected for further analysis.

TMS1 Expression Constructs:

The TMS1 cDNA derived from EST yl28a06 (Accession No. H16108) was subcloned into pcDNA3.1 (Invitrogen) to generate pcDNA-TMS1. A myc-epitope tag was fused to amino acid 2 of TMS1 was generated by PCR and subcloned into pcDNA3.1 to create pcDNAmycTMS1. A COOH-terminal truncation mutant (mycTMS1Δ100–195) was created from pcDNAmycTMS1 by Klenow fill-in of an internal BamHI site causing a frame shift at amino acid 100 followed by an in-frame stop codon. An $NH_2$-terminal mutant (pmycTMS1Δ2–99) was derived from pcDNAmycTMS1 by deletion of sequences between the myc tag and an internal BamHI site of TMS1, resulting in deletion of amino acids 2–99.

Bac Isolation and Radiation Hybrid Mapping:

A pooled human BAC library (Release III, Research Genetics) was screened by PCR using TMS1-specific primers in the 3' untranslated region of TMS1 5'-GCACTTTATAGACCAGCA-3' (SEQ ID NO:8) and 5'-ATTTGGTGGGATTGCCAG-3' (SEQ ID NO:9) and four positive BACs were identified. A TMS1 positive BAC was digested with HindIII, cloned into pBluescript SK+, and TMS1 positive subclones were identified by colony hybridization to an 175 bp fragment of the TMS1 cDNA. A 6 kb genomic HindIII subclone containing the TMS1 gene was identified. Sequence analysis was performed by the Emory University Sequencing Core Facility.

The same primers were used in a PCR-based screen of the human/rodent somatic cell hybrid mapping panel 2 (Coriell Cell Repository) to localize TMS1 to human chromosome 16. Fine mapping was carried out using radiation hybrid panels (Stanford RH Panel G3 and Stanford RH panel TNG4; Research Genetics). Results were analyzed using the Stanford Human Genome Center RHserver (available at the Stanford University website on the internet) and indicated linkage to markers SHGC-35326 on the G3 panel (lod score 7.16) and SHGC-61092 on the TNG4 panel (lod score 4.91).

Methylation-sensitive Restriction and Southern Blot Analysis:

Ten µg DNA isolated from 90SV or HMT.1E1 cells was digested with 200 units of the methylation-sensitive restriction enzyme Sac II or Eag I for 16 h followed by an additional 16 h digestion with 100 units of the methylation-insensitive enzyme HindIII. Digested DNA was separated by electrophoresis on a 1% agarose gel, transferred to a nylon filter (Zeta-Probe, BioRAD) and hybridized overnight with a random-prime labeled, 1.8 kb EcoRI TMS1 genomic probe. Blots were washed to a final stringency of 0.1×SSC, 0.1% SDS at 65° C. and exposed to X-ray film using intensifying screens (BioMAX-MS, Kodak).

Northern BlotAnalysis:

One µg poly A+ selected RNA was fractionated on a 1.5% agarose/formaldehyde gel, transferred to nylon filters, and hybridized with a random-prime labeled full length TMS1 cDNA fragment. Blots were washed to a final stringency of 0.1×SSC, 0.1% SDS at room temperature and exposed to X-ray film using an intensifying screen (BioMAX-MS, Kodak). Blots were stripped and re-hybridized with a human β-actin cDNA probe.

RT-PCR:

Six µg total RNA was pretreated with DNAse I (Life Technologies) and reverse transcribed using random hexamer primers and MMLV-reverse transcriptase according to the manufacturers instructions (Life Technologies). One/30th of the reverse transcriptase reaction equivalent to 200 ng starting RNA was used directly in a PCR reaction. The PCR reaction conditions were: 67 mM Tris-HCl, pH 8.8, 16.6 mM $NH_4SO_4$, 6.7 µM EDTA, 10 mM β-mercaptoethanol, 4.7 mM $MgCl_2$, 10% DMSO, 400 nM each primer in a 25 µl reaction. Hot start PCR was performed using an initial 5 minute incubation at 95° C. followed by the addition of 0.5 U Taq polymerase and 35 cycles of PCR (95° C., 30 s; 50–55° C., 60 s; 72° C., 60 s). Primers used for analysis of TMS1 were TGGGCCTGCAGGAGATG-3' (SEQ ID NO:13) and 5'-ATTTGGTGGGATTGCCAG-3' (SEQ ID NO:9) with an annealing temperature of 50° C. Primers used for the analysis for β-actin were 5'-CCTTCCTGGGCATGGAGTCCTG-3' (SEQ ID NO:14) and 5'-GGAGCAATGATCTTGATCTTC-3' (SEQ ID NO:15) with an annealing temperature of 55° C. Reaction products were separated by electrophoresis on a 5% or 6% polyacrylamide/Tris-borate-EDTA gel, stained with ethidium bromide and photographed.

Bisulfite Modification and Methylation-specific PCR:

Bisulfite modification and methylation-specific PCR were performed as previously described. (Herman, J. G., et al., Proc. Natl. Acad. Sci. U.S.A. 93:9821–9826, 1996) Briefly, 2 μg genomic DNA was denatured by incubation at 37° C. in 0.2N NaOH for 10 min. then treated with 3M sodium metabisulfite and 0.5 M hydroquinone at 50° C. for 16 h. DNA was desalted using Wizard DNA Clean-Ups (Promega). Modification was completed by the addition of NaOH to a final concentration of 0.3M and DNA was recovered by ethanol precipitation. Approximately 50 ng bisulfite-modified DNA was amplified by PCR with the following reaction conditions: 67 mM Tris-HCl, pH 8.8, 16.6 mM NH4SO$_4$, 6.7 μM EDTA, 10 mM β-mercaptoethanol, 6.7 mM MgCl$_2$, 1 μM each primer in a 25 μl reaction. Hot start PCR was performed using an initial 5 minute incubation at 95° C. followed by the addition of 0.5 U Taq polymerase (Life Technologies) and 35 cycles of PCR (95° C., 30 s; 58° C., 30 s; 72° C., 30 s). Reaction products were separated by electrophoresis on a 5% or 6% polyacrylamide gel, stained with ethidium bromide and photographed. Primers were designed from the interpolated sequence following bisulfite conversion assuming the DNA was either methylated or unmethylated at CpG sites within the primer sequence. To ensure maximal discrimination of unmethylated and methylated DNA, each primer was designed to overlap three potential methylation sites, one of which occurred at the 3' end of each primer. Primers utilized in the analysis of TMS1 methylation were 5'-GGTTGTAGTGGGGTGAGTGGT-3' (SEQ ID NO:16) and 5'-CAAAACATCCATAAACAACAACACA-3' SEQ ID NO:17) for the unmethylated reaction, and 5'-TTGTAGCGGGGTGAGCGGC-3' (SEQ ID NO:18) and 5'-AACGTCCATAAACAACAACGCG-3' (SEQ ID NO:19) for the methylated reaction.

Colony Formation Assays:

Breast cancer cells, including Hs57 8t, (3×10$^5$) were seeded into six well dishes and transfected with 1 μg pcDNA3.1 or the TMS1 expression constructs using 5 μl Lipofectamine reagent (Life Technologies). Twenty-four hours after transfection, cells were diluted 1:100–1:500 and seeded into 100 mm dishes in medium containing 400 μg/ml G418. After 14 days of selection, stable G418-resistant colonies were fixed and stained with 50% methanol, 0.25% crystal violet, and counted. The total number of colonies recovered per transfection cells was extrapolated from counting at least 300 G418$^r$ colonies per experiment. The number of colonies recovered from cells transfected with pcDNA3.1 in each experiment was considered to be 100%. Three independent transfection experiments were performed.

Apoptosis Assays:

293 human embryonic kidney cells were plated on glass coverslips in 24 well dishes at 1×10$^5$ cells per well, and were transfected with 0.4 μg of pcDNA3.1 or the TMS1 expression constructs plus 0.1 μg β-galactosidase expression vector (pCMVβgal, Clonetech) using the calcium phosphate precipitation method. Where indicated, 40 μM zVADfmk (Enzyme System Product, Livermore, Calif.) was included during the recovery period. Forty-eight hours after transfection, coverslips were fixed in 4% paraformaldehyde and stained for β-galactosidase activity, using X-gal, and for nuclear morphology, using Hoecsht 33528 dye. Cells were visualized by phase contrast microscopy. At least 200 β-galactosidase positive cells from randomly selected fields were counted from each transfection. Apoptotic cells were distinguished based on morphologic features typical of adherent cells undergoing apoptosis, including becoming condensed, rounded and detached from the growth surface as described. (McCarthy, J. V. et al., J.Biol.Chem. 273:16968–16975, 1998). At least 200 β-galactosidase positive cells from randomly selected fields were counted from each transfection. Each transfection experiment was repeated three times.

Results

At present, the mechanism in which CpG islands become abnormally methylated is not known, but this event can be induced in human somatic cells by ectopic expression of DNA methyltransferase-1 (DNMT1). Human fibroblasts overexpressing DNMT1 undergo progressive de novo methylation of endogenous CpG island sequences. (Vertino, P. M. et al., Mol.Cell Biol. 16:4555–4565, 1996) To identify potential downstream targets of methylation-mediated gene silencing, cDNA representational difference analysis was used to isolate genes that were down-regulated in cells overexpressing DNMT1 (referred to as HMT.1E1) relative to the immortalized human fibroblasts (90SV) from which they were derived. (Hubank, M. et al., Nucleic Acid Res. 22:5640–5648, 1994) After three rounds of subtraction, a predominant 350 bp fragment (RDA-2.15) was isolated, and shown to be differentially represented in cDNA derived from 90SV and HMT.1E1 cells. FIG. 1a shows the presence of the 350 bp fragment in 90SV cells but not HNMT.1E1.

Sequence analysis and BLAST homology searches of the Genbank and dbEST databases indicated that RDA-2.15 was derived from a novel gene represented by multiple human ESTs that defined a tentative human consensus (THC253346, TIGR Human Gene Index) as well as a unique Unigene cluster (Hs. 71869, NCBI Unigene project). A 770 bp cDNA was assembled from the complete sequence of two EST clones (yl28a06 and qwI3b06) that overlapped the entire Unigene cluster. The assembled cDNA sequence contains a 588 bp ORF with 5' and 3' UTRs of 74 bp and 97 bp, respectively, and includes the poly(A) tail. No additional 5' sequence was obtained using a 5' rapid amplification of cDNA ends protocol indicating that the cDNA sequence was full-length.

Figure 1B:
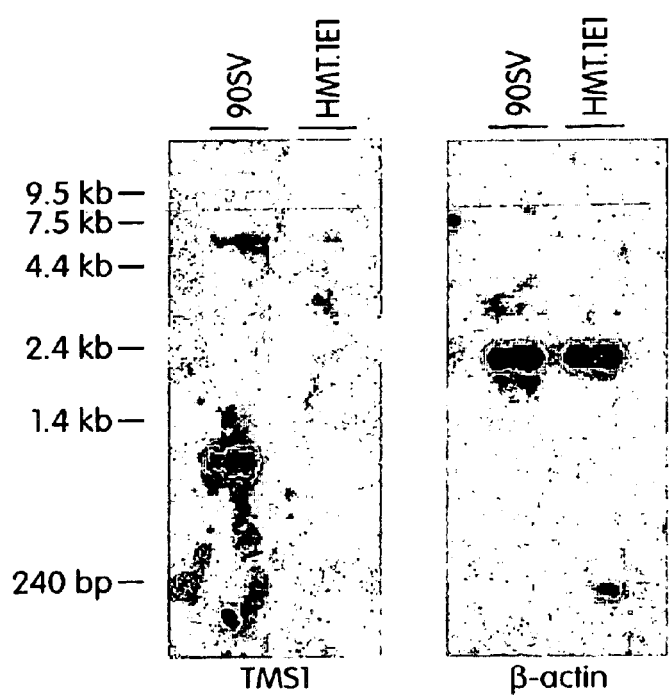
FIG. 1B is a representation of a Northern blot analysis of TMS1 and β-actin expression in cell lines 90SV and HMT.1E1.
Figure 1C:
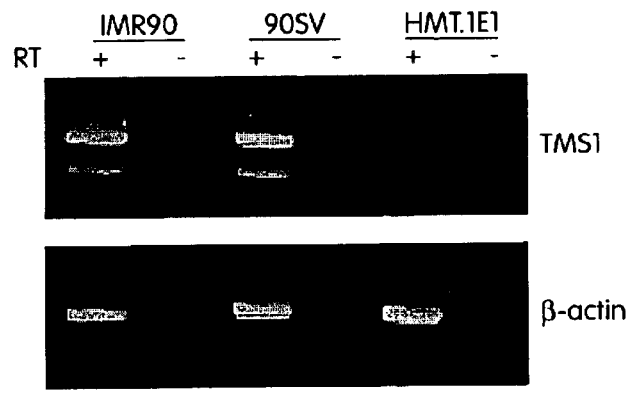
FIG. 1C is a representation of an RT-PCR analysis of TMS1 and β-actin expression in cell lines IMR90, 90SV and HMT.1E1, showing down-regulation of TMS1 in fibroblasts overexpressing DNMT1 (i.e., HMT.1E1) relative to control cells (i.e., 90SV and IMR90). Control reactions in which reverse transcriptase was omitted (-RT) were amplified under the same conditions.

The TMS1 cDNA probe hybridized to a ~0.8 kb message which was expressed at low, but clearly detectable levels in IMR90 normal human diploid fibroblasts and their immortalized derivatives, the 96SV cells (FIG. 1b). The same message was undetectable by Northern blot analysis in the DNMT1 overexpressing cell line, HMT.1E1, confirming that the gene identified by RDA was silenced in HMT.1E1 cells.(FIG. 1b). The same blot was stripped and rehybridized with a β-actin probe, revealing a ~2.4 kb band of equal intensity in all cell samples tested and confirming that the absence of TMS1 in HMT.1E1 was specific to that transcript, and probably not the result of unequal RNA loading. The exposure time for TMS1 was 3 days whereas that for β-actin was 4 hours.

Reverse-transcriptase polymerase chain reaction (RT-PCR) was also performed with the same cell lines. An amplified band corresponding to TMS1 was detected in IMR90 and 90SV but not in HMT.1E1. No band was detected in any sample in the absence of reverse transcriptase, confirming that the amplified band derived from RNA rather than genomic DNA. Again, amplification with β-actin specific primers resulted in an equal intensity band in all samples, indicating that the absence of a TMS1 transcript was most probably not the result of unequal sample loading. The differentially expressed gene was named TMS1 for target of methylation-induced silencing-1.

Figure 2A:
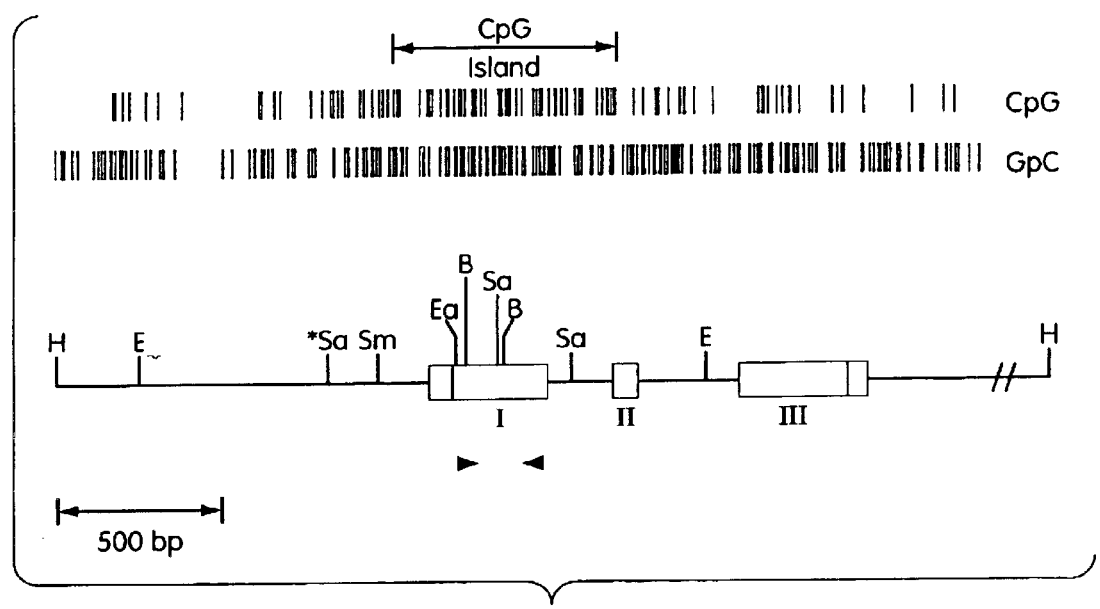
FIG. 2A shows the genomic structure of the TMS1 locus.

Restriction mapping and Southern blot analysis of the TMS1 locus confirmed that the absence of TMS1 expression in the HMT.1E1 cells was not a result of gene deletion or gross chromosomal rearrangement. To determine whether loss of TMS1 expression in the HMT.1E1 cells was related to methylation of the TMS1 gene, the genomic structure of TMS1 was first determined by partial sequencing of a human genomic BAC clone. Intron/exon boundaries were determined by comparison of the cDNA and genomic sequence. The TMS1 locus is composed of a coding region of ~1.8 kb including three exons of 449 bp (SEQ ID NO:5), 58 bp (SEQ ID NO:7), and 355 bp (SEQ ID NO:9) size (FIG. 2a). The first and third exons also contain 5' and 3' untranslated regions at their beginning and end, respectively. A ~600 bp CpG island was identified in the 5' end of TMS1 surrounding exon 1. This region showed a high C+G content (69%), a CpG/GpC ratio of 0.82, and the presence of multiple sites for methylation-sensitive, CpG-recognizing restriction enzymes that of ten cluster within CpG islands (SacII, EagI, BssHII, SmaI) (FIG. 2a). (Bird, A. P., Nature 321, 209–213, 1986) Other restriction sites located in this locus include 2 HindIII sites and 2 EcoRI sites.

Figure 2B:
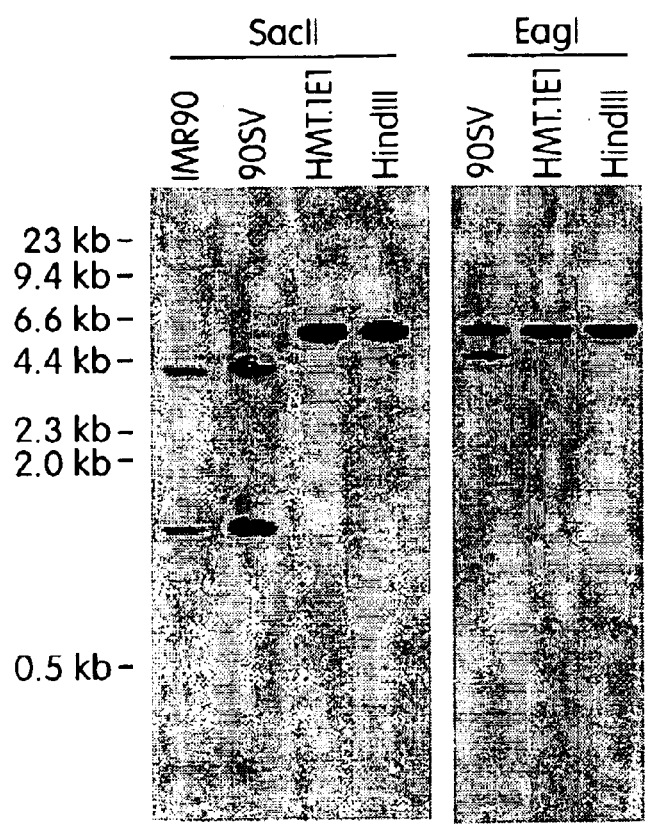
FIG. 2B shows the methylation status of the TMS1 CpG island as determined by Southern analysis following methylation-sensitive restriction analysis.

Examination of the methylation status of the TMS1 CpG island by Southern blot analysis using methylation-sensitive restriction enzymes in the TMS1 expressing (1MR90 and 90SV) and non-expressing (HMT.1E1) cells indicated that silencing of TMS1 correlated with hypermethylation of the TMS1 CpG island (FIG. 2b). The probe used was the 1.8 kb EcoRI TMS1 genomic fragment, containing the first and second exons. HindIII digestion alone released a ~6 kb genomic fragment containing the entire TMS1 locus. Absence of methylation at SacII sites within the CpG island is indicated by bands of 4.4 kb, 1.4kb and 0.23 kb. The 5' most SacII site (*Sa, see FIG. 2a) was found to lie outside the CpG island and was methylated in all normal tissue samples tested. Absence of methylation at the EagI site is indicated by bands of 1.2 kb and 4.8 kb. HindIII plus SacII digestion of IMR90 DNA resulted in three bands of 4.4 kb, 1.4 kb and 0.23 kb size. Similar digestion of DNA from 90SV cells revealed bands of 6 kb, 4.4 kb, 1.6 kb, 1.4 kb and 0.23 kb. HMT.1E1 DNA digestion with HindIII and SacII resulted only in the 6 kb band. Digestion of SV90 DNA with HindII and EagI revealed three bands of sizes 6.0 kb, 4.8 kb, and 1.2 kb. Again, HMT.1E1 DNA was not further digested with EagI. These results indicated that IMR90 normal diploid fibroblasts were unmethylated at SacII and EagI sites within the TMS1 CpG island. However, the TMS1 CpG island exhibited a partially methylated pattern in the 90SV cells, with both methylated and unmethylated alleles present in the population (FIG. 2b). This result is similar to some other CpG islands which have been studied in this model system which have accumulated some methylation as result of immortalization, prior to insertion of DNMT1. (Vertino, P. M. et al., Mol.Cell Biol. 16:4555–4565, 1996) HMT.1E1 cells exhibited complete methylation of Sacil and EagI sites in the TMS1 CpG island, as observed from its complete protection from digestion with these enzymes (FIG. 2b).

Figure 2C:
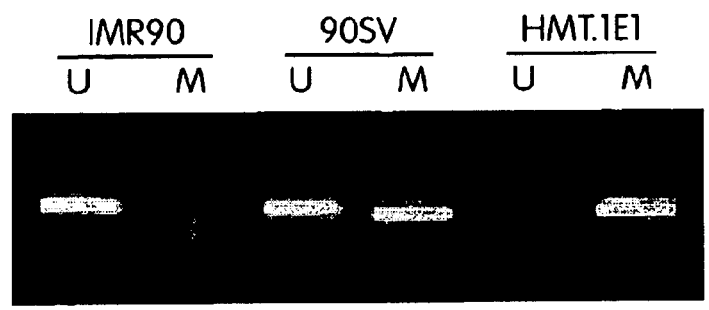
FIG. 2C shows the results of methylation-specific PCR of DNA from HMT.1E1, 90SV and IMR90 cell lines.

The methylation status of the TMS1 CpG island was further analyzed by a more sensitive methylation-specific PCR (MSP) technique in which methylated and unmethylated alleles in the population can be specifically amplified following chemical modification of the DNA with sodium bisulfite. (Herman, J. G., et al., Proc.Natl.Acad.Sci.U.S.A. 93:9821–9826, 1996) Bisulfite modified DNA was used as a template for parallel PCR amplification reactions using primers designed to anneal specifically to unmethylated (U) or methylated (M) DNA. The product of the methylated reaction was 191 bp, and that of the unmethylated reaction was 196 bp due to differences in the length of the primers. The primers used for the reactions were located in the first exon. IMR90 DNA was amplified only in the unmethylated reaction, HMT.1E1 DNA was amplified only in the methylated reaction and DNA from 90SV was amplified in both. These data were consistent with those obtained by methylation-sensitive restriction analysis and confirmed that the IMR90 cells were unmethylated and the 90SV cells were partially methylated whereas the HMT.1E1 cells were fully methylated at the TMS1 CpG island (FIG. 2c). These data indicated that overexpression of DNMT1 in the HMT.1E1 cells promoted both hypermethylation of the TMS1 CpG island and silencing of TMS1.

Figure 3A:
FIG. 3A shows methylation specific PCR analysis of bisulfite-modified DNA from primary human mammary epithelial cells (HMEC) and two immortal, non-tumorigenic breast epithelial cell lines (MCF10A, Hs578Bst) compared to that of nine breast cancer cell lines (MCF-7, T47-D, ZR-75-1, Hs578t, MDA MB231, MDA MB468, SKBR3, CAMA1, BT-20). Parallel amplifications reactions were performed using primers specific to methylated (M) and unmethylated (U) DNA.
Figure 3B:
FIG. 3B shows the TMS1 mRNA expression profile of breast epithelial cells and breast cancer cells using reverse transcribed RNA amplified with primers to TMS1 (top panel) and β-actin (bottom panel). Control reactions in which reverse transcriptase was omitted (-RT) were amplified under the same conditions.

Several CpG island loci that are methylated and silenced in human tumors are also subject to de novo methylation in the DNMT1 overexpression model. In particular, the CpG islands of the E-cadherin, estrogen receptor and HIC1 genes are progressively de novo methylated in the DNMT1 overexpressors (although not expressed in fibroblasts), and are methylated and silenced in human breast and other tumors. (Graff, J. R., et al., Cancer Res. 55:5195–5199, 1995; Vertino, P. M. et al., Mol.Cell Biol. 16:4555–4565, 1996; Fujii, H., et al., Oncogene 16:2159–2164, 1998; Ottaviano, Y. L., et al., Cancer Res. 54:2552–2555, 1994) To determine whether TMS1 was also a target for methylation-associated silencing in human cancer, the expression of TMS1 and the methylation status of the TMS1 CpG island in primary human mammary epithelial cells (HMEC), two immortal, non-tumorigenic breast epithelial cell lines, (Hs578Bst and MCF10A) and six breast cancer cell lines (MCF-7, T47-D, ZR-75-1, Hs578t, MDA MB231 and MDA MB468) were determined. Parallel amplifications were performed as described above. Expression levels were determined by RT-PCR with β-actin controls. TMS1 was predominantly unmethylated and expressed in HMEC cells and the two immortalized, non-tumorigenic breast epithelial cell lines (FIG. 3a and b). In stark contrast, 3 of 6 breast carcinoma cell lines (ZR75-1, Hs578t and MB23 1) were completely methylated at the TMS1 CpG island locus and similarly did not express TMS1 (FIG. 3a and b). As seen in the fibroblast system, breast cancer cell lines that were either completely unmethylated (MCF-7) or only partially methylated (T47D, MDA MB468) at the TMS1 CpG island retained expression of TMS1 (FIG. 3a and b).

Figure 3C:
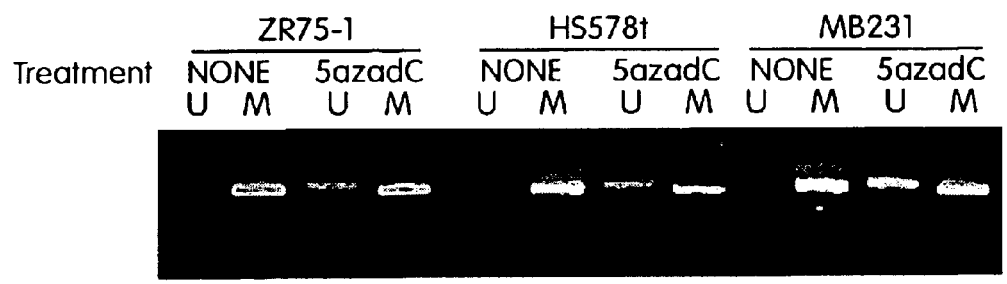
FIG. 3C shows the effect of a demethylating agent (5-aza-2'deoxycytidine) on TMS1 methylation and re-expression in normal and breast cancer cell lines.
Figure 3D:
FIG. 3D shows the TMS1 and β-actin MRNA expression profile in normal and breast cancer cell lines (ZR75-1, Hs578t and MDA MB231 cells) treated with DNA methyltransferase inhibitor 5-aza-2'deoxycytidine at 0.5 µM concentration for 3 days.

The ZR75-1, Hs578t and MDA MB231 breast cancer cell lines exhibited complete methylation of TMS1 and failed to express TMS1 message. If loss of TMS1 expression is directly related to methylation of the CpG island, then expression of TMS1 should be restored following treatment with a demethylating agent. Treatment of ZR75-1, Hs578t and MDA MB231 cells with the DNA methyltransferase inhibitor 5-aza-2'-deoxycytidine at 0.5 $\mu$M concentration for 3 days resulted in the partial demethylation of the TMS1 CpG island and re-expression-of TMS1 transcript (FIG. 3C and D). Methylation of the TMS1 CpG island was analyzed by methylation specific PCR and expression of TMS1 was analyzed by RT-PCR with β-actin controls. Control cultures in which the inhibitor was absent did not re-express TMS1. The absence of TMS1 expression in these cell lines is therefore not due to abnormalities at the gene level or the inability to express TMS1, for example, due to a lack of necessary transcription factors, but rather is directly related to the methylation of TMS1.

Figure 4A:
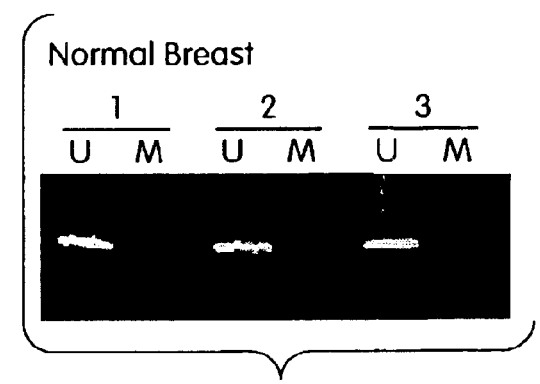
FIG. 4A shows the methylation status of TMS1 in normal breast tissue from reduction mammoplasty using methylation-specific PCR analysis.
Figure 4B:
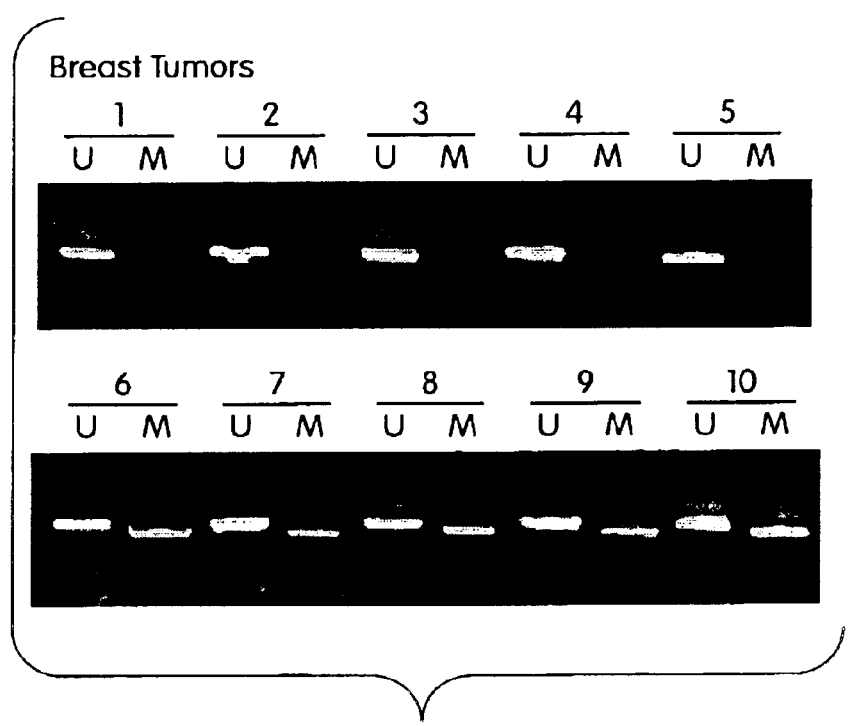
FIG. 4B shows the methylation status of TMS1 in primary breast tissues from reduction mammoplasty using methylation-specific PCR analysis.
Figure 4C:
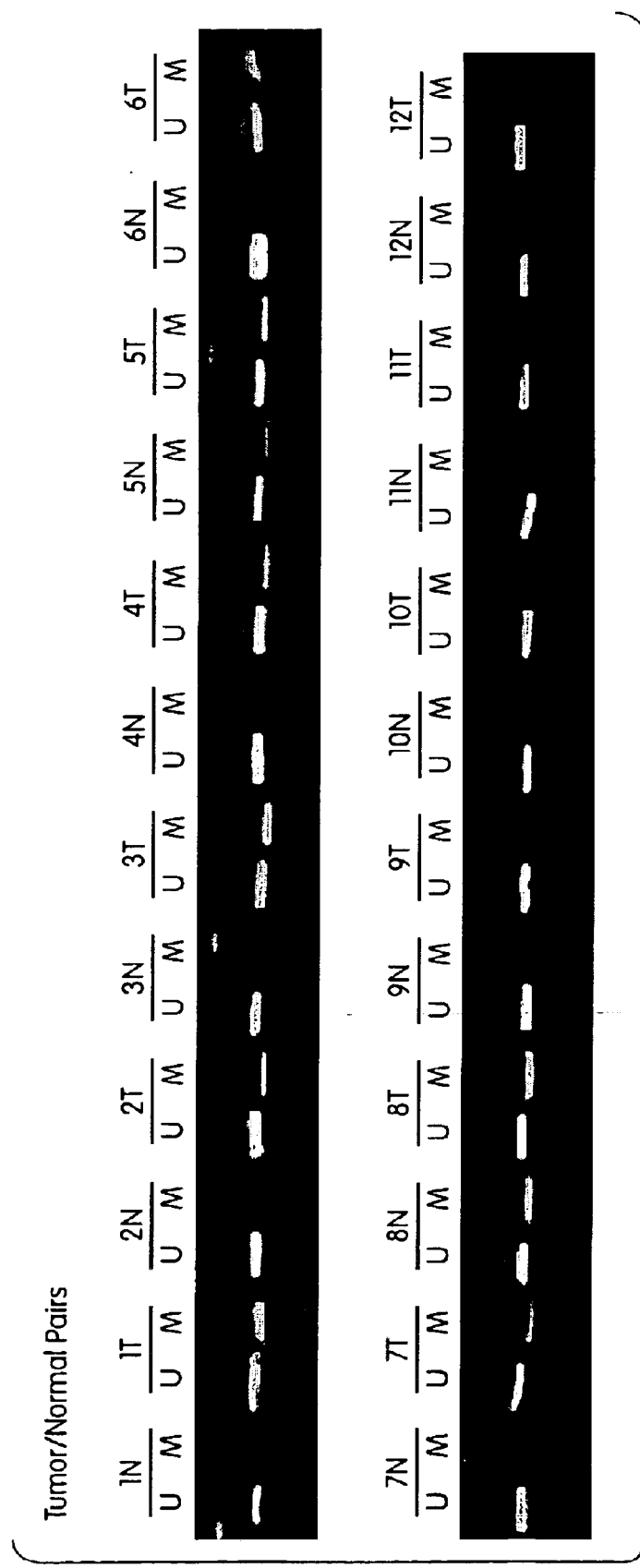
FIG. 4C shows the methylation status of TMS1 in paired normal-appearing tissue (N) adjacent to breast tumors (T). Shown are 12 representative pairs out of a total of 18 analyzed.

That TMS1 was abnormally methylated and silenced in a substantial proportion of human breast cancer cells suggested that TMS1 provides a novel tumor suppressor function. TMS1 exhibited widespread low level expression in human tissues, with the greatest expression in colon, spleen, small intestine, lung and peripheral blood leukocytes (FIG. 4a). TMS1 transcripts were also observed in heart, thymus, kidney, liver and placenta. Interestingly, TMS1 was silent in other human tumor cell lines, including Molt 4 lymphocytic leukemia cells and HeLa cervical carcinoma cells (FIG. 4b). Cell lines HL60, K562, Raji, SW480, A549 and G361 all expressed varying degrees of TMS1.

Figure 5A:
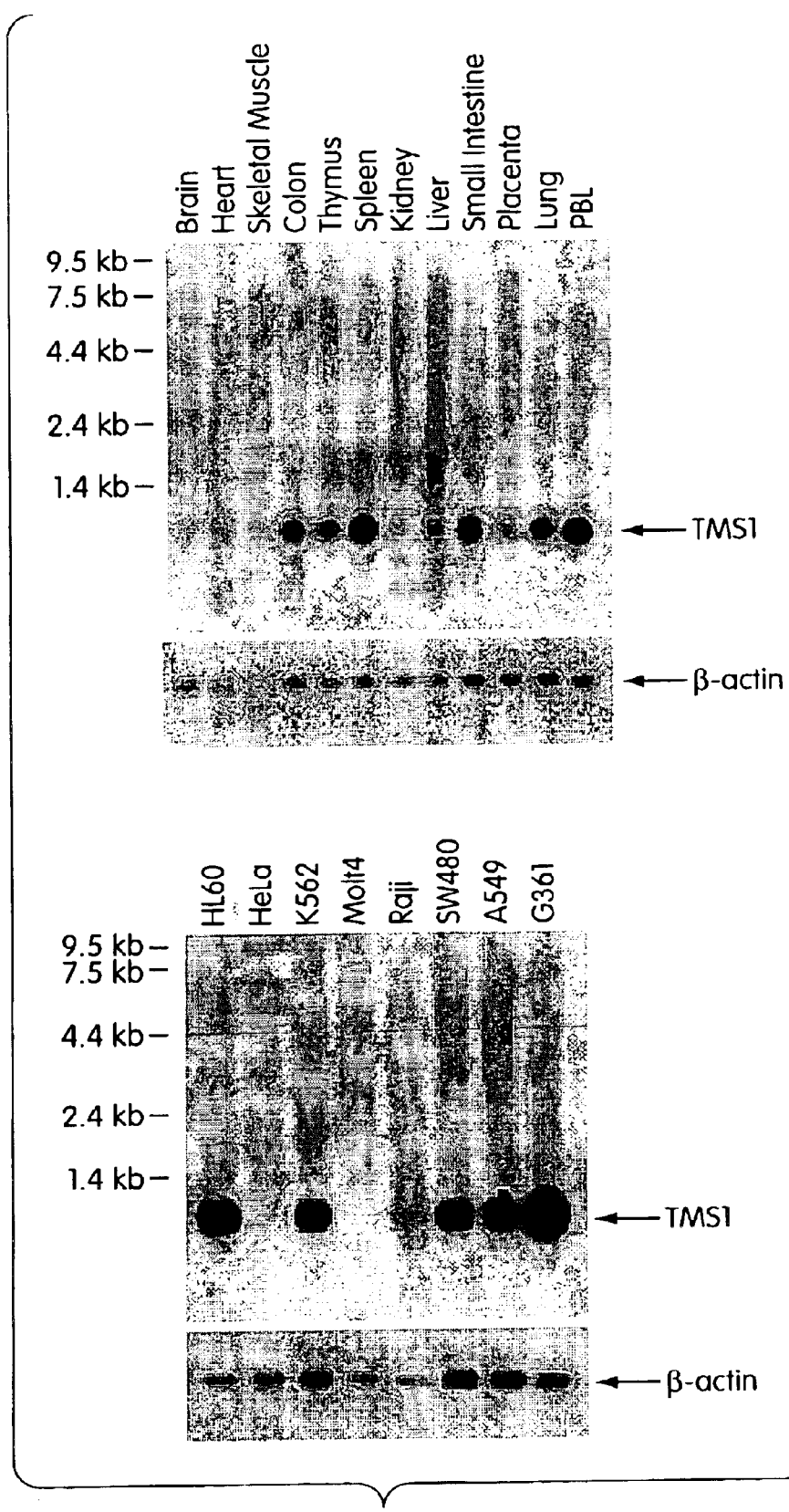
FIG. 5A shows the expression of TMS1 and β-actin in normal human tissues and human tumor-derived cell lines.

The cDNA sequence indicated that TMS1 encodes a predicted protein of 195 amino acids and 25 kDa. Through a combination of BLAST homology searches of Genbank and the SMART domain recognition database, it was discovered that TMS1 contained a carboxy-terminal caspase recruitment domain (CARD). (Schultz, J. et al., Proc.Natl.Acad.Sci.U.S.A. 95:5857–5864, 1998) An amino acid alignment of the TMS1 carboxy-terminus with the CARD motif of other apoptotic signaling proteins is shown in FIG. 5a. Numbers in parentheses indicate the position in the amino acid sequence. Reverse type indicate ≧50% amino acid identity; gray shading indicates ≧50% similarity through conserved amino acid substitutions.

Figure 5B:
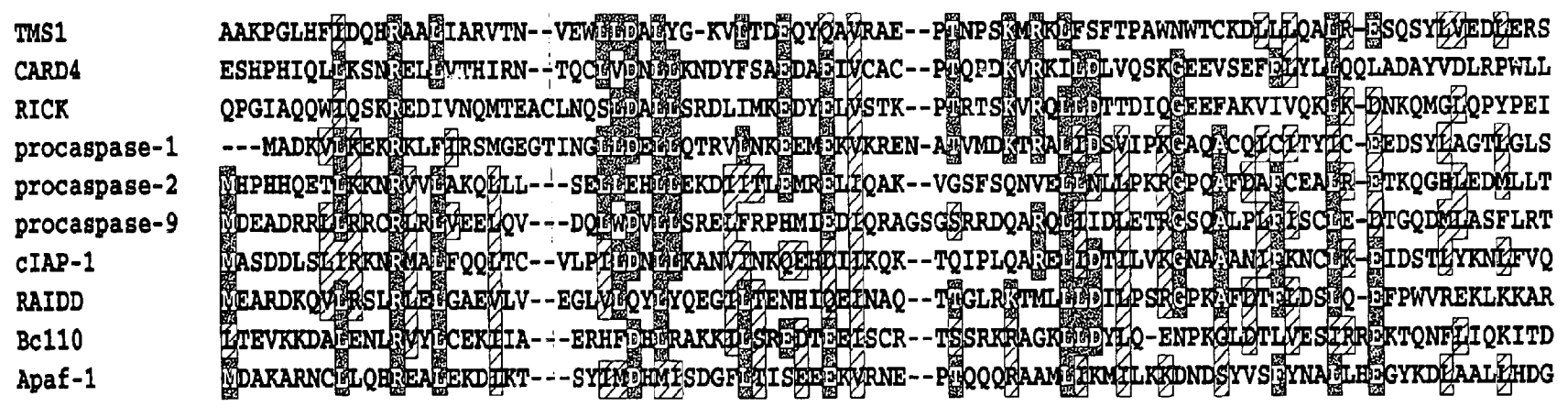

The presence of a CARD indicates that TMS1 can play a role in apoptosis. To test this hypothesis, the effect of ectopic TMS1 expression on apoptosis in 293 cells was analyzed. 293 cells were transfected with 0.4 μg of the indicated TMS1 expression construct and 0.1 μg pCMVβgal. Forty-eight hours after transfection cells were stained with X-gal and at least 200 β-galactosidase cells were counted for each condition. Data (mean±SD) represent the percentage of ,galactosidase positive cells exhibiting morphologic apoptosis. Three independent transfection experiments were performed. Expression of wild-type TMS1, a myc tagged TMS1, or a deletion mutant expressing only the CARD (mycTMS1Δ2–99) induced apoptosis when transiently transfected into 293 cells (FIG. 5b). Deletion of the CARD (mycTMS1Δ100–195) abolished the proapoptotic activity of TMS1 and more closely approximated the level of apoptosis induced by vector alone (FIG. 5b). Apoptotic activity was slightly diminished when the CARD was used alone.

Figure 5C:
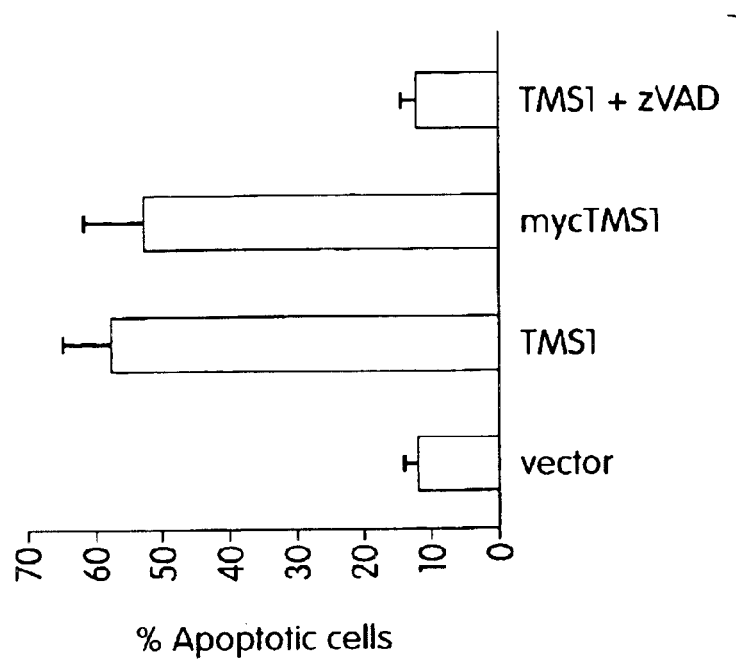
FIG. 5C shows the apoptosis inducing ability of TMS1 and TMS1 variants. Where indicated, zVAD was added immediately following transfection. Data are presented as the percentage of β-galactosidase positive cells exhibiting apoptosis (mean±SD) from three independent transfection experiments.
Figure 5C:
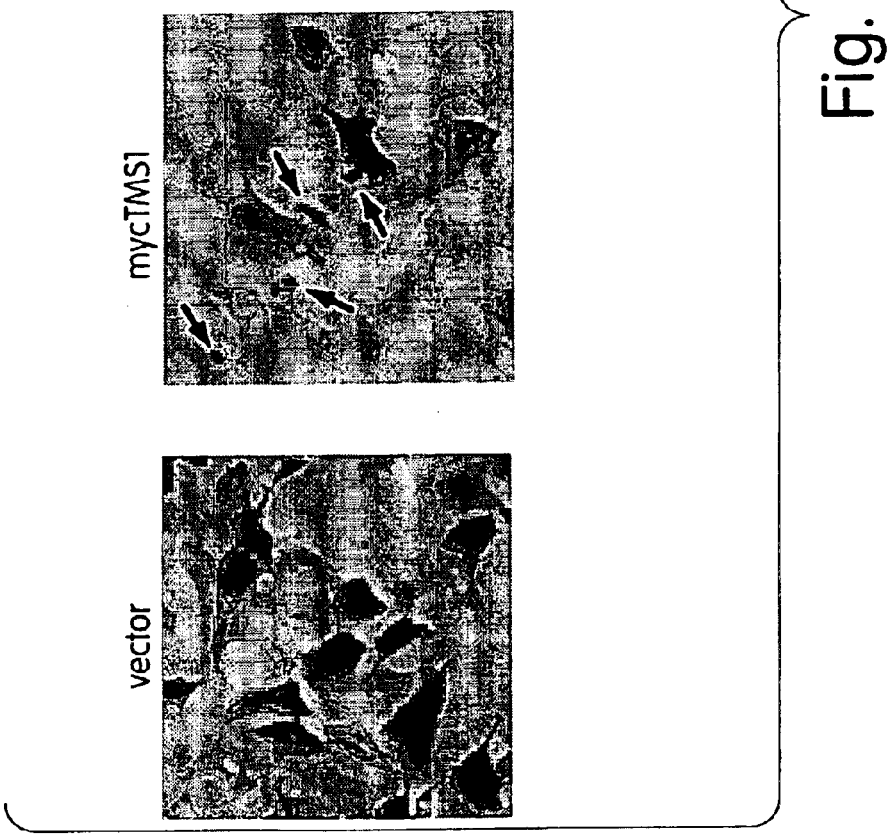
Figure 5D:
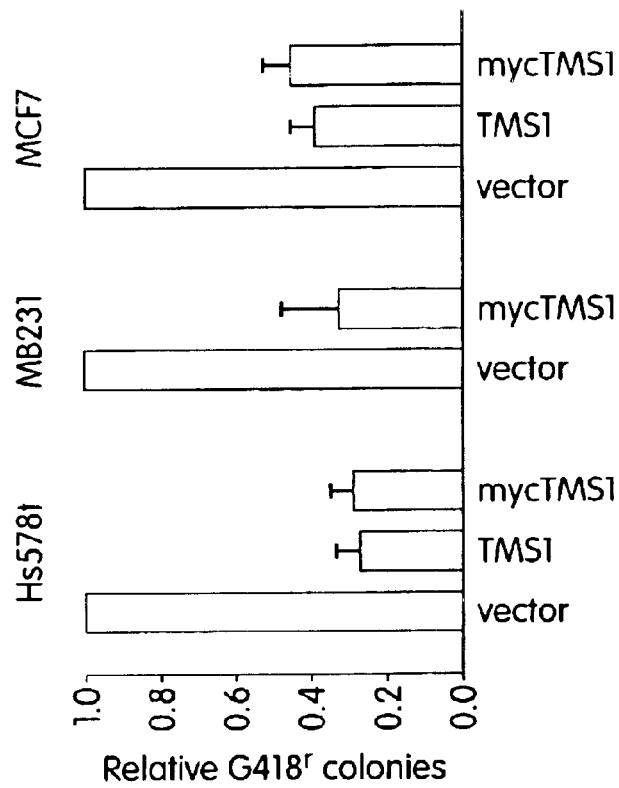
FIG. 5D shows the effect TMS1 and TMS1 variants on colony forming activity of transfected breast cancer cell lines. Data (mean±SD) represent the number of G418$^r$ colonies recovered for each test construct relative to that of the vector. At least three independent transfection experiments were performed.
Figure 5D:
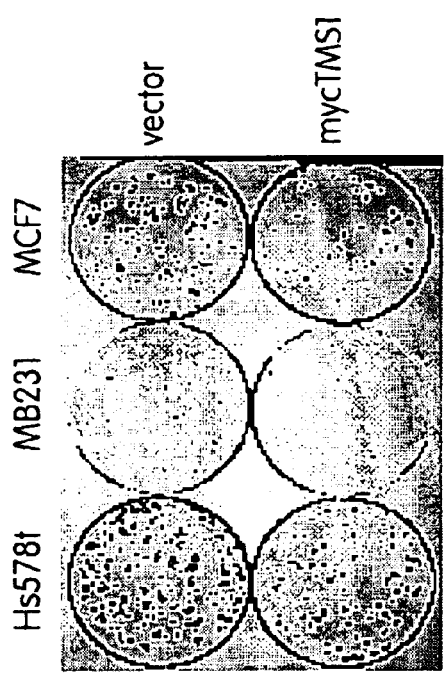

Given the proapoptotic function of TMS1, the consequences of TMS1 silencing were determined by re-introducing TMS1 into breast cancer cells lacking endogenous TMS1 expression. Colony forming ability of TMS1 negative breast cancer cells stably transfected with TMS1 expression constructs was analyzed in the following manner. Hs578t cells were transfected with the pcDNA3.1 vector or the indicated TMS1 expression construct. Twenty-four hours after transfection, cells were plated at limiting dilution in G418 selection medium. Stable G418-resistant colonies remaining after 14 days were fixed and stained with crystal violet. Data (mean±SD) represent the percentage of surviving colonies relative to the vector control from three independent transfection experiments. The total number of colonies in the controls ranged from 2967–3700 between experiments. Stable expression of wild-type TMS1, or TMS1 derivatives capable of inducing apoptosis, inhibited colony formation in Hs578t cells by about 70% (FIG. 5c). In contrast, expression of the apoptosis-incompetent, CARD-deleted TMS1 mutant had a much reduced effect, and reduced colony formation by only 40% (FIG. 5c). Therefore, TMS1 functions in the promotion of apoptosis and this activity is mediated by the CARD.

Abnormal methylation of gene-associated CpG islands is well recognized as a mechanism associated with loss of tumor suppressor gene expression in human cancers. (Baylin, S. B., et al., Adv.Cancer Res. 72, 141–196, 1998; Jones, P. A. et al., Nat.Genet. 21:163–167, 1999) However, it has been unclear whether methylation plays a causative role in carcinogenesis because it is not known whether abnormal methylation is sufficient to precipitate the silencing of an active, endogenous gene. TMS1 is the first gene to be identified in a functional screen for such methylation-induced gene silencing events. The finding that TMS1 is abnormally methylated and silenced in response to overexpression of DNMT1 is interesting for two reasons. First, it suggests that methylation can drive gene silencing in vivo, perhaps through the binding of methylated DNA binding proteins and the recruitment of histone deacetylase complexes. (Jones, P. L., et al. Nat.Genet. 19:187–191, 1998; Nan, X., et al., Nature 393: 386–389, 1998) Secondly, increased expression of DNMT1 is transforming, and was recently shown to be an early downstream effector of oncogene-induced transformation. (Wu, J., et al. Proc.Natl.Acad.Sci.U.S.A. 90:8891–8895, 1993; Bakin, A. V. et al., Science 283:387–390, 1999) Taken together, these data are consistent with a direct role for abnormal methylation in gene silencing and tumorigenesis.

Genetic alterations that lead to cellular resistance to apoptosis, such as mutational inactivation of proapoptotic genes such as TP53 and BAX, or translocation and activation of anti-apoptotic genes like BCL2, promote tumorigenesis by allowing damaged or unnecessary cells to persist and accumulate further genetic insult. (Pan, H., et al., Cancer Surv. 29:305–327, 1997) These data suggest that epigenetic alterations that result in the silencing of a proapoptotic gene such as TMS1 may provide a similar survival advantage. These data extend the role of abnormal methylation in carcinogenesis to include the silencing of genes that act as positive mediators of cell death. These data support a role for abnormal methylation in the epigenetic silencing of TMS1, and implicate TMS1 as a novel tumor suppressor for breast and other cancers.

Example 2

Methods and Materials

Plasmids:

pcDNA-TMS1 and pcDNA-mycTMS1 have been described previously. (Salvesen, G. S. and Dixit, V. M. Cell. 91: 443–446, 1997) The TMS1 COOH-terminal truncation mutant (mycTMS1Δ100–195) was created from pcDNA-mycTMS1 by Klenow fill-in of an internal BamHI site, resulting in a frame-shift at amino acid 100 followed by an in-frame stop codon. DN-caspase-8 and DN-caspase-9 constructs were gifts from K. Bhalla. (Muzio, M., et al. Cell. 85: 817–827, 1996; Li, P., et al. Cell. 91: 479–489,91997) The NF-κB CAT (pJECAT2.6) and mutant NF-κB CAT (p2.6mκB1) constructs were gifts from J. Boss. (Ping, D., et al. J. Immunol. 162: 727–734, 1999)

Creation of TMS1 Inducible Expression Cells:

The Ecdysone-Inducible Mammalian Expression System (Invitrogen, Carlsbad, Calif.) was used to create clones of 293 cells that inducibly express mycTMS1. The mycTMS1 cDNA was cloned into the HindIII/XhoI sites of the pIND expression vector (pIND-mycTMS1). EcR-293 cells (Invitrogen, Carlsbad, Calif.) containing the pVgRXR vector were transfected with pIND-mycTMS1 or pIND using Lipofectamine Reagent (Life Technologies, Grand Island, N.Y.). Cells were maintained in selection medium containing 600 µg/ml G418 for 3 weeks to isolate stably transfected colonies. Clonal populations transfected with pIND-mycTMS1 were then tested for inducible expression by western blot analysis after addition of 5 µM pon A.

Cell Culture and Transfection:

Human embryonic kidney 293 cells and EcR-293 derivatives (MTMS22 and PIND1) were cultured in DMEM (Life Technologies, Inc. Grand Island, N.Y.) supplemented with 10% fetal bovine serum. MTMS22 and PIND1 cells were maintained in the presence of 400 µg/ml zeocin and 600 µg/ml G418. Transfections of 293 cells were carried out in 24-well dishes with $1 \times 10^5$ cells and 0.5 µg total DNA per well using the calcium phosphate method. As a transfection marker, a βgal expression vector (β-gal CMV) was included at a 1:4 ratio with the indicated cDNA constructs. In co-transfections with DN-caspase-8 or DN-caspase-9, 0.2 µg of pcDNA-TMS1 was transfected with 0.2 pg of pcDNA3.1 or DN-caspase-8 or -9 along with 0.1 µg of β-gal CMV as a transfection control.

Morpholoical Apoptosis Assay:

48 h after transfection, 293 cells were fixed on coverslips and stained for β-gal activity. Nuclei were stained using Hoechst 33258 dye (Sigma, St. Louis, Mo.). Transfected (blue) cells were examined for morphologic changes indicative of adherent cells undergoing apoptosis including cell rounding and reduction in size, nuclear fragmentation and membrane blebbing.

DNA Fragmentation:

Where indicated, MTMS22 cells were treated with 5 µM pon A (Invitrogen) or 40 µM Z-VAD-fmk (Enzyme System Products, Livermore, Calif.). DNA was collected from $2 \times 10^6$ cells as previously described. (Burow, M. E., et al. Cancer Research. 58: 4940–4946, 1998) 5 µg of DNA from each sample was visualized by separation on a 2% agarose gel containing ethidium bromide.

CAT Assay for NF-κB Activation:

293 cells plated at 60% confluence in 6 well dishes were transfected with 0.2 µg of the NF-κB CAT reporter construct (pJECAT2.6) and increasing amounts of pcDNA-mycTMS1 by the calcium phosphate method. 0.2 µg of β-gal CMV was included as a transfection control, and the total amount of DNA transfected was kept constant at 2 µg with pcDNA3.1. Cell lysates were collected 36 h after transfection in β-gal lysis buffer (Promega, Madison, Wis.) and assayed for β-gal activity using the β-Galactosidase Enzyme Assay System (Promega, Madison, Wis.) per manufacturer's instructions. CAT assays were performed basically as described. (Ausubel, F. M., et al. Curr. Prot. Mol. Biol., Vol. 2, pp. 9.7.5–9.7.6: John Wiley & Sons, Inc., 1997) In brief, cell lysates were incubated with [$^{14}$C]chloramphenicol and n-butyryl CoA. [$^{14}$C]-labeled acetylated chloramphenicol was then separated from the nonacetylated form by organic phase extraction, and radioactive counts were determined using a scintillation counter.

Fluorescence Microscopy:

Cells were fixed in 4% formaldehyde, permeabilized in 0.2% triton X-100 in PBS and blocked with 3% BSA/0.02% triton X-100 in PBS. Coverslips were incubated with myc antibody (9E10) (Santa Cruz Biotechnology, Santa Cruz, Calif.) at a 1:500 dilution, washed 4 times in PBS/0.02% triton X-100 and incubated with a secondary FITC antibody at a 1:2000 dilution. After 3 more washes, cells were stained with Hoechst 33258 dye to visualize nuclei, washed twice in PBS and mounted on slides. Cells were viewed at 400× or 1000× using the Olympus BX60 microscope. Digital images were captured using IP Lab Spectrum v.3.1 software (Scanalytics, Inc., Fairfax, Va.).

Results

Figure 6A:
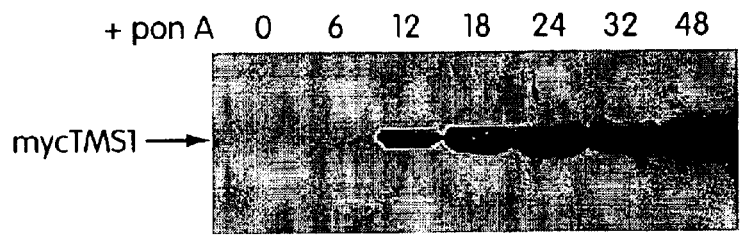
FIG. 6A illustrates induction of caspase-dependent apoptosis by TMS1 using an ecdysone-inducible expression system to express myc-tagged TMS1. MTMS22 cells were treated with pon A for the indicated times, and TMS1 expression was examined by immunoblotting with a monoclonal myc (9E10) antibody.
Figure 6B:
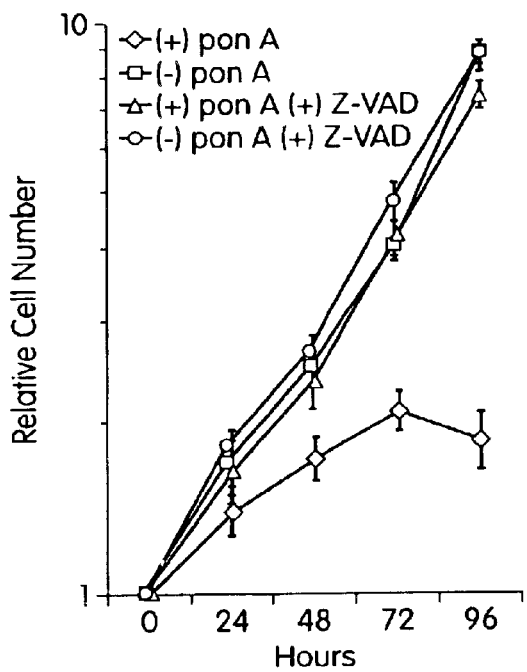
FIG. 6B shows MTMS22 cell proliferation as determined in the presence or absence of 5 µM pon A to induce TMS1 expression and with or without 40 µM Z-VAD. Data represent the mean±SD of triplicate determinations from a representative growth experiment.
Figure 6C:
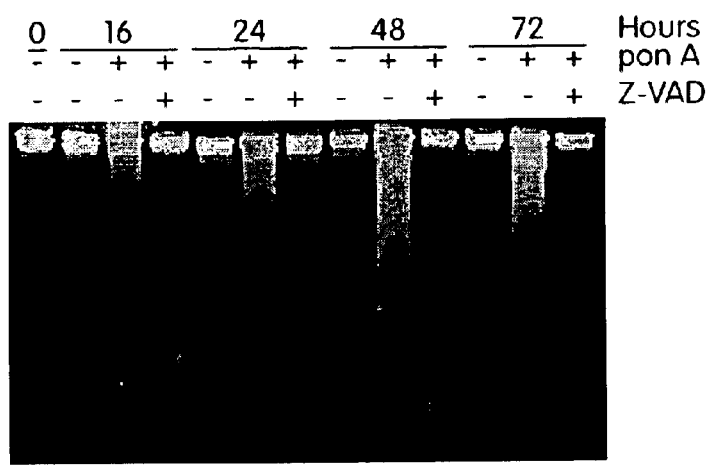
FIG. 6C shows the induction of apoptosis of MTMS22 cells treated with pon A and/or Z-VAD for the indicated times. DNA fragmentation was visualized by EtBr/agarose gel electrophoresis.

An ecdysone-regulated expression system was used to create a 293 cell line that inducibly expresses TMS1. A clonal population (called MTMS22) that exhibited no detectable background expression of TMS1 and high inducible expression in the presence of the ecdysone analog, pon A, was isolated and used for the following studies. In addition, a clonal population of cells stably transfected with the empty expression vector was isolated as a control (PIND1). Upon addition of pon A to the MTMS22 cells, mycTMS1 was detectable by western blotting as early as 6 hours after treatment and continued to accumulate in the cells over 48 hours (FIG. 6A). To determine whether TMS1 had an effect on cellular proliferation, MTMS22 cells were counted over a 96-hour period in the presence or absence of pon A. By 48 hours after induction of TMS1, cells had begun to round up and lift of f the plates (data not shown) and cell growth was significantly inhibited (FIG. 6B). By 96 hours, pon A-treated cells were declining in number, confirming cell death. As a biochemical marker for apoptosis, MTMS22 cells were examined for DNA fragmentation in the presence or absence of TMS1 expression. Upon induced expression of TMS1, DNA laddering was observed as early as 16 hours and was most evident at 48 hours (FIG. 6C). To address whether the death-inducing effects of TMS1 were caspase-dependent, these experiments were also carried out in the presence of the general caspase inhibitor, Z-VAD-fmk. Addition of Z-VAD blocked both TMS1-induced cell death (FIG. 6B) and DNA fragmentation (FIG. 6C). Neither pon A or Z-VAD had any effect on the growth of pIND1 control cells (data not shown). These data indicate that TMS1 expression induces apoptosis, and this activity is dependent on caspase activation.

Figure 7A:
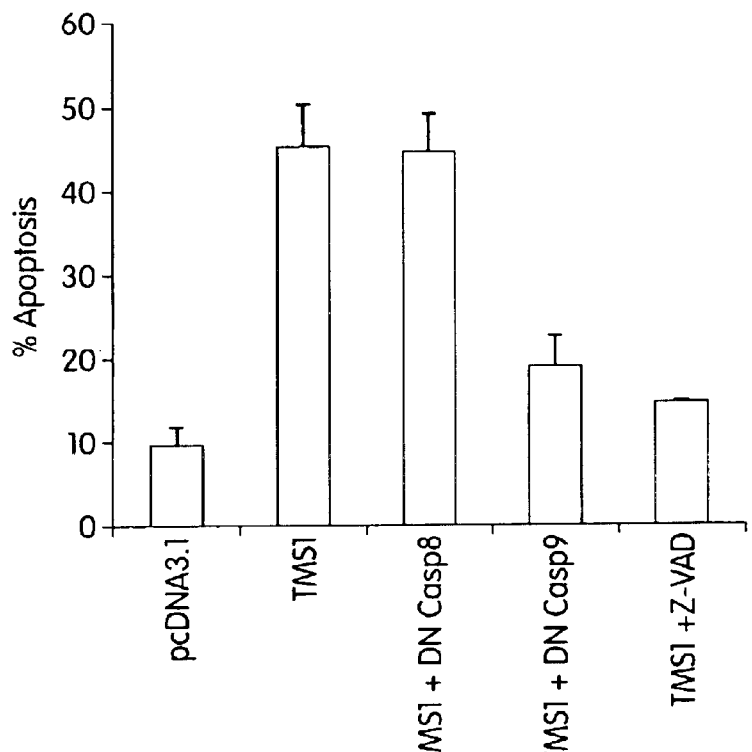
FIG. 7A shows the result of transient transfection of 293 cells with pcDNA-TMS1, with pcDNA-TMS1 plus DN-caspases-8 or -9, or with pcDNA-TMS1 in the presence of 40 µM Z-VAD. Forty-eight hours after transfection, the percentage of transfected (β-gal positive) cells exhibiting morphologic features of apoptosis was determined. At least 200 transfected cells were counted per transfection. Data represent the mean±SD of three separate experiments.

To identify candidate caspase pathways in which TMS1 functions, the ability of dominant negative (DN) forms of the initiator caspases, caspase-8 and -9 to block TMS1-induced apoptosis was tested. 293 cells were transiently transfected with TMS1 alone or TMS1 plus DN-caspases-8 or DN-caspase-9 and examined for morphological changes associated with apoptosis. Ectopic expression of TMS1 resulted in a 6-fold increase in cell death (FIG. 7A). The apoptotic activity of TMS1 was not affected by DN-caspase-8; in contrast, DN-caspase-9 significantly inhibited TMS1-induced apoptosis. The ability of DN-caspase-9 to block cell death induced by TMS1 was similar to the effect seen with the general caspase inhibitor, Z-VAD. These data show that the proapoptotic activity of TMS1 is mediated at least in part through the activation of caspase-9.

Figure 7B:
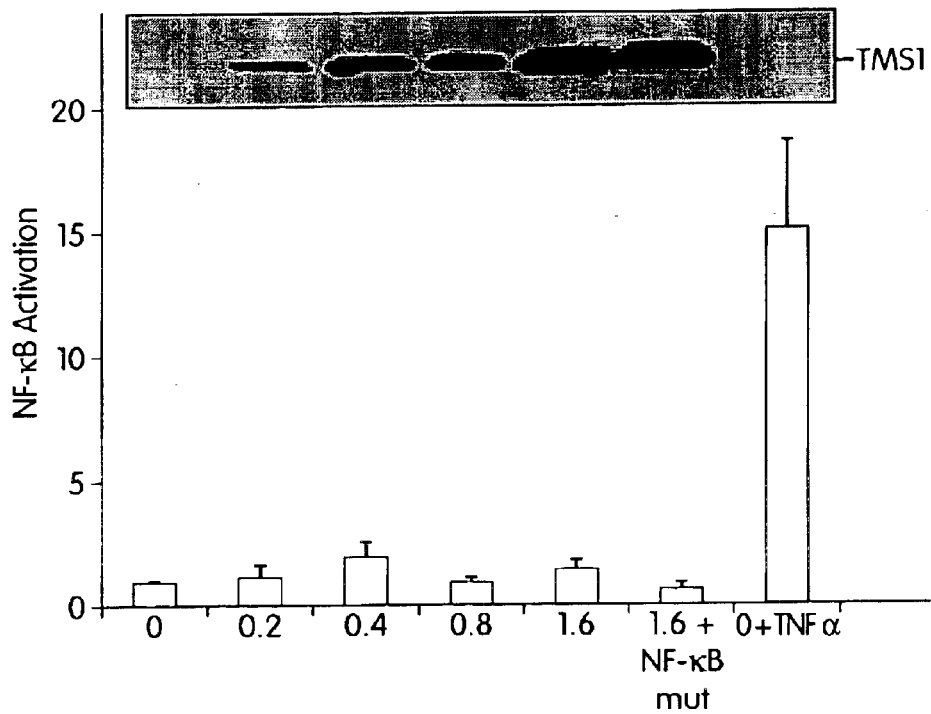
FIG. 7B shows that transient transfection of 293 cells with the indicated amounts of pcDNA-mycTMS1 has no effect on NF-κB activation, using a CAT activity assay. As a control, 293 cells were transfected with an NF-κB CAT reporter construct (pJECAT2.6). A CAT reporter construct containing a mutated NF-κB site, (p2.6mκB1) was used as a negative control. TNFα (20 µM) was added a positive control. Lysates used for CAT assays were subjected to immunoblot analysis for TMS1.

In addition to the ability to trigger or enhance apoptosis, several CARD-containing proteins have been shown to activate the transcription factor, NF-κB. To test whether TMS1 was able to induce NF-κB activated transcription, 293 cells were co-transfected with an NF-κB-responsive CAT reporter construct along with increasing amounts of TMS1. TMS1 expression had no effect on NF-κB-dependent transcriptional activation (FIG. 7B). In contrast, the addition of TNF$^3$-α induced a 15-fold increase in activation.

Figure 8A:
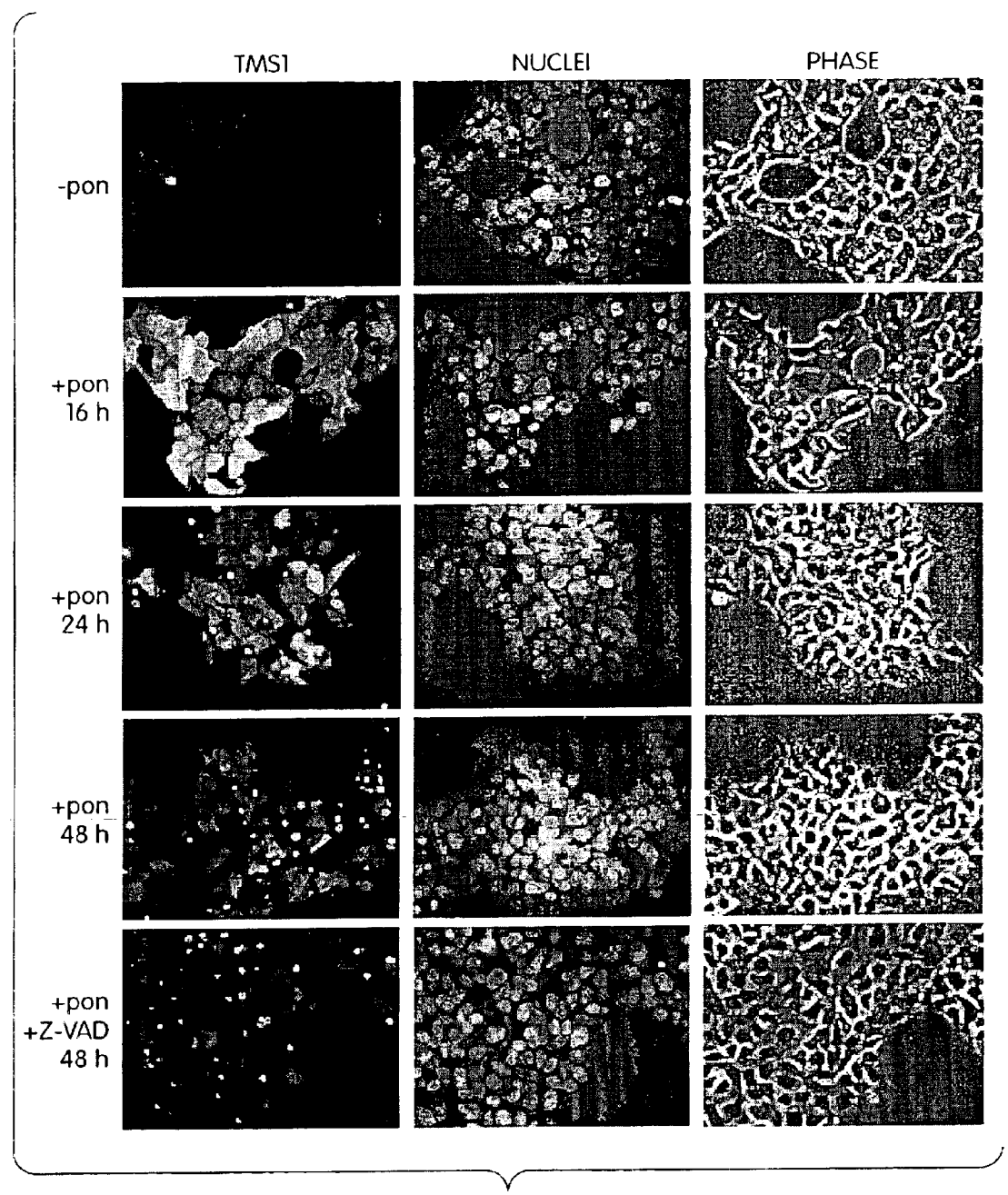
FIG. 8A shows the subcellular localization of TMS1 in MTMS22 cells induced to express myc-tagged TMS1 by addition of pon A for the indicated times and prepared for visualization of TMS1 by immunofluorescence using a myc (9E10) monoclonal antibody. Nuclei were visualized by staining with Hoescht 33258 dye. Cells were viewed at 400×magnification.
Figure 8B:
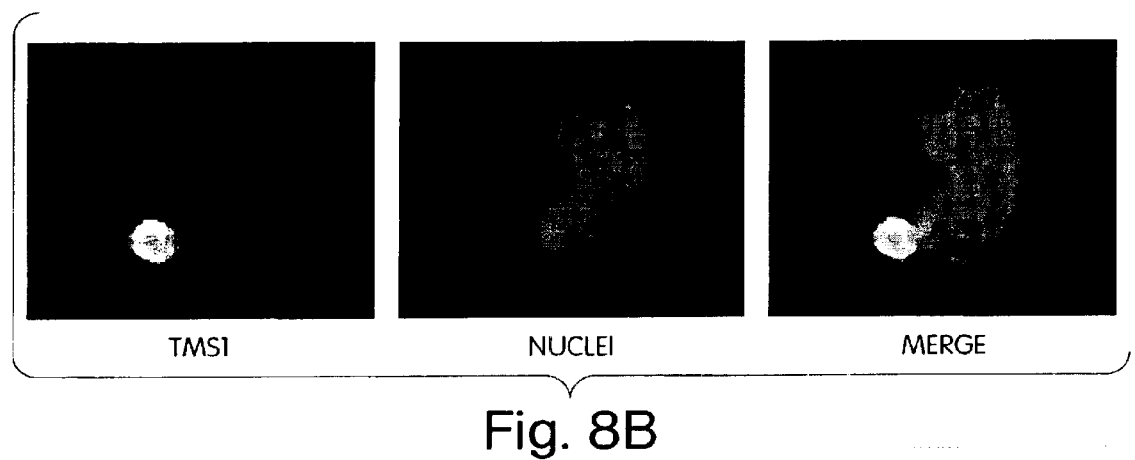
FIG. 8B shows the localization of TMS1 in 293 cells transiently transfected with pcDNA-mycTMS1 and processed to visualize TMS1 and nuclei by immunofluorescence. Images are at 1000×magnification.

To determine the subcellular localization of TMS1, MTMS22 cells induced to express TMS1 were examined by immunofluorescence. Sixteen hours after induction, TMS1 showed diffuse cytoplasmic staining (FIG. 8A). However, by 24 h, a fraction of the cells showed a punctate fluorescent pattern, and by 48 h, a majority of the cells contained the punctate staining and lacked diffuse cytoplasmic staining. Under high power, the TMS1 aggregates appeared as hollow, spherical structures made up of many smaller balls (FIG. 8B). For a majority of the cells, there appeared to be only one structure per cell, located in close proximity to the nucleus. Redistribution of TMS1 from the cytoplasm to the aggregates correlated with partial detachment of the cells from the growth surface, resulting in increased refraction of light when viewed by phase contrast microscopy (FIG. 8A). The timing of TMS1 relocalization following induction coincided with TMS1-induced cell death and the appearance of DNA fragmentation (compare FIG. 8A to FIG. 6B, 6C). An intriguing result was observed in cells expressing TMS1 in the presence of Z-VAD. Although Z-VAD was able to block the apoptotic effects of TMS1 (FIG. 6B, 6C), it had no effect on the formation of the TMS1-containing spherical aggregates (FIG. 8B). Therefore, TMS1 aggregate formation is not a downstream effect of apoptosis, but rather appears to be an intermediate event that lies upstream of caspase activation.

Figure 9A:
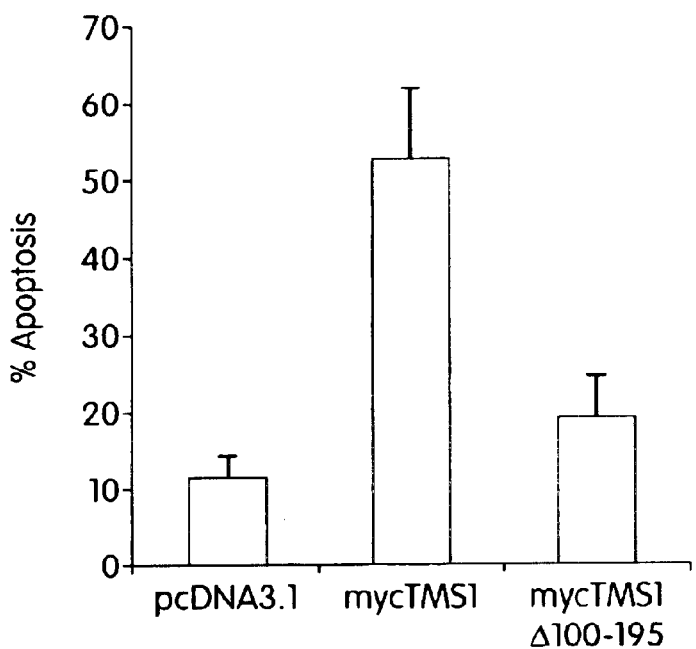
FIG. 9A shows that TMS1-induced apoptosis and localization are dependent on the CARD. Percentages of 293 apoptotic cells were deternmined 48 h after transient transfection with pcDNA3.1, pcDNA-mycTMS1 or pcDNAmycTMS1Δ100–195. At least 200 transfected cells were counted per transfection, and results represent the mean±SD of 3 separate experiments.
Figure 9B:
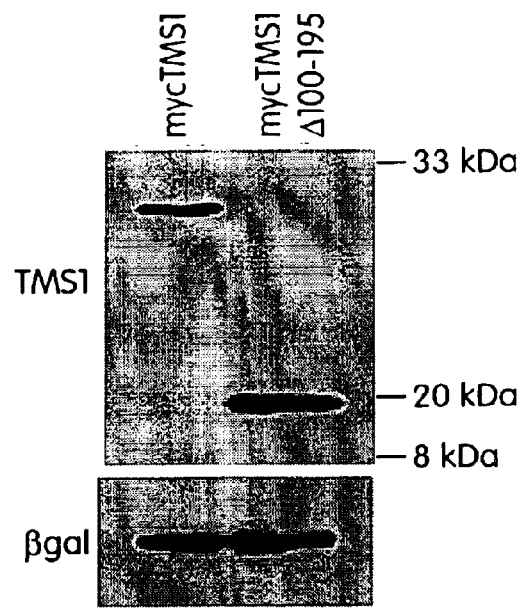
FIG. 9B is a representation of a Western immunoblot analysis of lysates from transfected 293 cells showing expression of full-length or truncated TMS1 (top) and β-gal (bottom).
Figure 9C:
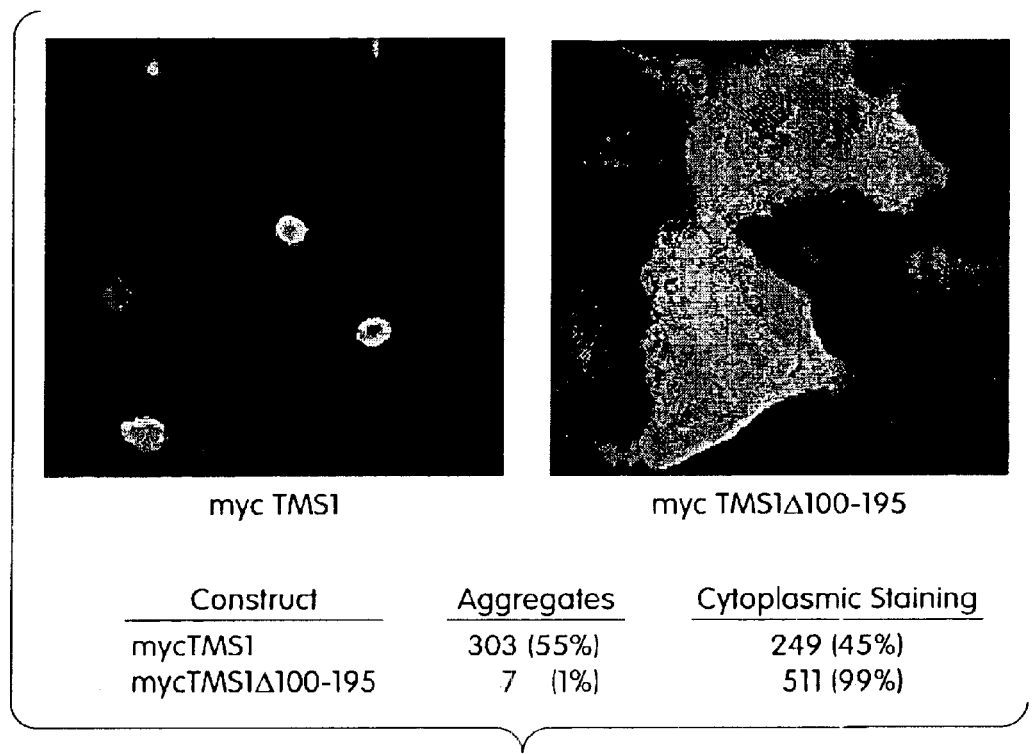
FIG. 9C is a representation of photographs of 293 cells transiently transfected with pcDNA-mycTMS1 or pcDNA-mycTMS1Δ100–195 and prepared for visualization of TMS1 by immunofluorescence. At least 500 TMS1-positive cells were scored for subcellular localization of TMS1.

To test the importance of the CARD region for the function and localization of TMS1, a truncated form of TMS1 lacking the C-terminal CARD was compared to full length TMS1 in its ability to induce apoptosis and to localize to the spherical structures. Transient expression of mycTMS1 induced apoptosis in 293 cells, whereas deletion of the CARD (mycTMS1Δ100–195) abolished the proapoptotic activity (FIG. 9A). Western blot analysis confirmed that both TMS1 proteins were expressed at equal levels (FIG. 9B). Deletion of the CARD also affected subcellular localization of TMS1. Whereas wild-type TMS1 localized to the aggregates, TMS1 lacking the CARD remained almost exclusively cytoplasmic (FIG. 9C). Thus, both the proapoptotic activity and the localization of TMS1 to spherical structures are dependent on the CARD.

TMS1 is a novel CARD-containing protein that, with the exception of the CARD, is structurally unrelated to other known CARD adaptor and regulatory proteins. Ectopic expression of TMS1 alone was able to trigger apoptosis in 293 cells, and cell death correlated with relocalization of TMS1 from the cytoplasm to perinuclear, ball-like structures. Several lines of evidence support the idea that redistribution of TMS1 is an intermediate step in a TMS1-triggered apoptotic pathway. First, the aggregate structures were formed in the absence of caspase activity, implying that TMS1 aggregation is not a consequence of apoptosis, but rather is an event that occurs upstream of caspase activation. In addition, deletion of the CARD region of TMS1 inhibited aggregate formation and abolished the proapoptotic activity of TMS1, suggesting that aggregation and the CARD is necessary for TMS1-induced apoptosis. Thus, aggregation of TMS1 appears to be a causative event in TMS1-triggered cell death.

Relocalization and aggregation of apoptotic signaling proteins appears to be an important step in caspase activation. FADD and caspase-8 have been shown to redistribute into ordered, subcellular filaments in cells transfected with FADD. (Siegel, R. M., et al. J. Cell Biol. 141: 1243–1253, 1998; Perez, D. and White, E. J. Cell Biol. 141: 1255–1266, 1998) Localization of FADD and caspase-8 was dependent on their death effector domains, and disruption of the filaments blocked FADD-induced apoptosis. Similarly, Apaf-1, procaspase-9 and cytochrome c have been shown to shift into large, multimeric complexes ($>1.3 \times 10^3$ kDa) termed apoptosomes to initiate caspase-9 activation. (Zou, H., et al. J. Biol. Chem. 274:11549–11556, 1999) Based on these and similar studies is the induced-proximity model which proposes that clustering of receptors and/or adaptor proteins with procaspases leads to caspase activation. (Salvesen, G. S. and Dixit, V. M. Proc. Natl. Acad. Sci. USA. 96: 10964–10967, 1999) Overexpression of TMS1 results in CARD-mediated clustering of the protein, and the structures that are formed may include other proteins whose association can trigger caspase activation and apoptosis.

The data presented herein show that the proapoptotic activity of TMS1 was caspase-dependent, and in particular required the activity of caspase-9. Caspase-9 is involved in the activation of apoptosis following release of cytochrome c from the mitochondria, an almost universal phenomenon during apoptosis triggered by numerous stimuli, including DNA damage and various chemotherapeutic agents. (Kuida, K., et al. Cell. 94: 325–337, 1998; Hakem, R., et al. Cell. 94: 339–352, 1998) The data therefore indicate that TMS1 acts as part of a signaling cascade for initiating activation of caspase-9 in response to certain external stimuli.

Several CARD-containing proteins including RICK/RIP2, CARD4/Nod1 and BCL10/CIPER/CLAP have been shown to trigger NF-κB-mediated transcription, in addition to playing a role in caspase activation. (Willis, T. G., et al. Cell. 96: 35–45, 1999; Zhang, Q., et al. Nature Genet. 22: 63–68, 1999; Inohara, N., et al. J. Biol. Chem. 273: 12296–12300, 1998; McCarthy, J. V., et al. J. Biol. Chem. 273: 16968–16975, 1998; Bertin, J., et al. J. Biol. Chem. 274: 12955–12958, 1999; Inohara, N., et al. J. Biol. Chem. 274: 14560–14567, 1999; Koseki, T., et al. J. Biol. Chem. 274: 9955–9961, 1999; Srinivasula, S. M., et al. J. Biol. Chem. 274: 17946–17954, 1999) Activation of NF-κB by DNA damaging agents or TNF-α can act as part of a regulatory feedback loop that operates to prevent cell death, most likely by inducing expression of anti-apoptotic genes. (Baichwal, V. R. and Baeuerle, P. A. Current Biology. 7: R94-R96, 1997) Indeed, NF-κB target gene products including cIAP-1, cIAP-2, TRAF1 and TRAF2 have been shown to protect cells from apoptosis induced by TNF-α. (Wang, C.-Y., et al. Science. 281: 1680–1683, 1998) TMS1 had no effect on the activation of NF-κB.

Genetic alterations that provide resistance to apoptosis promote tumorigenesis by allowing cancer cells to persist and accumulate further genetic damage. (Pan, H., et al. Cancer Surv. 29: 305–327, 1997) Genetic changes affecting the function or expression of CARD proteins can provide such a survival advantage. The gene encoding the proapoptotic CARD-containing protein BCL10 is subject to translocation in MALT B cell lymphomas, resulting in a variety of truncation mutations that disrupt the ability of BCL10 to activate apoptosis. (Willis, T. G., et al. Cell. 96: 35–45, 1999; Zhang, Q., et al. Nature Genet. 22: 63–68, 1999) Likewise, the TMS1 gene locus has been shown herein to be silenced by aberrant DNA methylation in human breast cancers. Given the proapoptotic function of TMS1 described herein, loss of expression of this CARD-containing protein through epigenetic alterations can provide cancer cells with a means to escape apoptosis. Since the effects of TMS1 are caspase-9-dependent, loss of TMS1 expression may disrupt normal apoptotic responses to DNA damage or cellular stress, thus providing resistance to some anti-cancer therapies including some forms of irradiation as well as select chemotherapeutic agents.

Equivalents

It should be understood that the preceding is merely a detailed description of certain embodiments. It therefore should be apparent to those of ordinary skill in the art that various modifications and equivalents can be made without departing from the spirit and scope of the invention, and with no more than routine experimentation. It is intended to encompass all such modifications and equivalents within the scope of the appended claims.

All references, patents and patent applications that are recited in this application are incorporated by reference herein in their entirety.

What is claimed is presented below and is followed by a sequence listing:

I claim:

1. A method for identifying a subject at risk of developing a cancer characterized by abnormally increased methylation of a CpG island containing TMS1 nucleic acid molecule comprising
   determining a level of methylation of a CpG island of a TMS1 nucleic acid molecule in a biological sample from a subject, and
   comparing the level of methylation of the CpG island of the TMS1 nucleic acid molecule in the biological sample to a control
   wherein the CpG island of the TMS1 nucleic acid molecule is selected from the group consisting of
      (a) nucleic acid molecules which hybridize under stringent conditions to a complement of a molecule consisting of SEQ ID NO:4, wherein the stringent conditions are 65° C. and 3.5×SSC, and
      (b) complements of (a),
   wherein the TMS1 nucleic acid molecule codes for a TMS1 polypeptide comprising a caspase recruiting domain and having apoptosis inducing activity, and
   wherein an increase in the level of methylation of the CpG island of the TMS1 nucleic acid molecule in the biological sample compared to the control identifies a subject at risk of developing the cancer.

2. A method for identifying a subject having cancer who is at risk of being non-responsive to an apoptosis-dependent anti-cancer therapy comprising:
   determining a level of methylation of a CpG island of a TMS1 nucleic acid molecule in a biological sample from a subject having cancer, and
   comparing the level of methylation of the CpG island of the TMS1 nucleic acid molecule in the biological sample to a control,
   wherein the CpG island of the TMS1 nucleic acid molecule is selected from the group consisting of
      (a) nucleic acid molecules which hybridize under stringent conditions to a complement of a molecule consisting of SEQ ID NO:4, wherein the stringent conditions are 65° C. and 3.5×SSC, and
      (b) complements of (a),
   wherein the TMS1 nucleic acid molecule codes for a TMS1 polypeptide comprising a caspase recruiting domain and having apoptosis inducing activity, and
   wherein an increase in the level of methylation of the CpG island of the TMS1 nucleic acid molecule in the biological sample compared to the control identifies a subject who is at risk of being non-responsive to an apoptosis-dependent anti-cancer therapy.

3. The method of claim 1, wherein the level of methylation is determined using a technique selected from the group consisting of methylation sensitive restriction analysis, methylation specific polymerase chain reaction (MSP), sequencing of bisulfite modified DNA, methylation-sensitive single nucleotide primer extension (Ms-SNuPE), and combined bisulfite restriction analysis (COBRA).

4. The method of claim 1, wherein the biological sample is breast tissue.

5. The method of claim 1, wherein the control comprises a normal tissue from a normal subject.

6. The method of claim 2, wherein the level of methylation is determined using a technique selected from the group consisting of methylation sensitive restriction analysis, methylation specific polymerase chain reaction (MSP), sequencing of bisulfite modified DNA, methylation-sensitive single nucleotide primer extension (Ms-SNuPE), and combined bisulfite restriction analysis (COBRA).

7. The method of claim 2, wherein the cancer is breast cancer.

8. The method of claim 6, wherein the biological sample is a breast cancer tumor.

9. The method of claim 2, wherein the control is normal tissue from a normal subject.

10. The method of claim 9, wherein the control is normal tissue from the subject having cancer.

11. The method of claim 2, wherein the apoptosis-dependent anti-cancer therapy is a DNA damaging anti-cancer therapy.

12. The method of claim 2, wherein the apoptosis-dependent anti-cancer therapy is radiation therapy.

13. The method of claim 2, wherein the apoptosis-dependent anti-cancer therapy is chemotherapy.

14. The method of claim 2, further comprising administering to the subject at risk of being non-responsive to an apoptosis-dependent anti-cancer therapy, a demethylating agent and an apoptosis-dependent anti-cancer therapy.

15. The method of claim 2, further comprising administering to the subject at risk of being non-responsive to an apoptosis-dependent anti-cancer therapy, an anti-cancer therapy selected from the group consisting of biological response modifying therapy, immunotherapy, cancer vaccine therapy, hormone therapy and angiogenesis inhibiting therapy.

16. A method for identifying a subject at risk of developing a cancer characterized by abnormally increased methylation of a TMS1 nucleic acid molecule comprising determining a level of methylation of a TMS1 nucleic acid molecule in a biological sample from a subject, and comparing the level of methylation of the TMS1 nucleic acid molecule in the biological sample to a control wherein the TMS1 nucleic acid molecule comprises a CpG island and is selected from the group consisting of
(a) nucleic acid molecules which hybridize under stringent conditions to a complement of a molecule consisting of SEQ ID NO:4, and which code for a TMS1 polypeptide comprising a caspase recruiting domain and having apoptosis inducing activity, wherein the stringent conditions are 65° C. and 3.5×SSC, and
(b) complements of (a), and wherein an increase in the level of methylation of the TMS1 nucleic acid molecule in the biological sample compared to the control identifies a subject at risk of developing the cancer.

17. A method for identifying a subject having cancer who is at risk of being non-responsive to an apoptosis-dependent anti-cancer therapy comprising:

determining a level of methylation of a TMS1 nucleic acid molecule in a biological sample from a subject having cancer, and comparing the level of methylation of the TMS1 nucleic acid molecule in the biological sample to a control, wherein the TMS1 nucleic acid molecule comprises a CpG island and is selected from the group consisting of
(a) nucleic acid molecules which hybridize under stringent conditions to a complement of a molecule consisting of SEQ ID NO:4, and which code for a TMS1 polypeptide comprising a caspase recruiting domain and having apoptosis inducing activity, wherein the stringent conditions are 65° C. and 3.5×SSC, and
(b) complements of (a), and wherein an increase in the level of methylation of the TMS1 nucleic acid molecule in the biological sample compared to the control identifies a subject who is at risk of being non-responsive to an apoptosis-dependent anti-cancer therapy.

* * * * *

SEQUENCE LISTING

<160> NUMBER OF SEQ ID NOS: 27

<210> SEQ ID NO 1
<211> LENGTH: 2821
<212> TYPE: DNA
<213> ORGANISM: Homo Sapiens

<400> SEQUENCE: 1

```
aagcttttga atacaacatg ctgcaggcat cacagcctca ttcattcctt cactcagcaa      60
atctttactc agcacctaat gtgttccaga tacatttttt tttttcagat ggaatctagc     120
tctgtcaccc aggctggagt gcagtggtgc aatcttggct cactgtagcc tctgcctccg     180
aggttcaagc gattctcatg cctcagccgc cctagtagct aggattacag gcgccctcca     240
ccacacacag ctatttccag gtacattctt gacgctagga attcagcaaa gaataagaca     300
gttaaggtct ccgatgctca taggcctcac attttagaga gggatgaatg tccaataagc     360
atataaacat ataatatgtc agggtcgtat gactacaagg aacagtgatt gttacaaccc     420
agatgagagg gaaaaataaa ggattccaaa tatcccctt gggaagtaga gtcaggattc     480
aaacaaagaa ctgtatggct tcaagttcat ggtctttaat ctcctggagg ctgtctctct     540
ttcttttttc tttttttaa tcagtgttgg gatcaaattc tggctcccct aggaagcatc     600
tggcaaggtt tcgggagcca tcgggttggc catgttatgc tggaatattt ataagcaccg     660
gagggttatc cccatgtcgt agaaaatgaa actgaagctc agagagattt gcactctctg     720
cccttttgta caactcattt ttccccagta tgtggaattg agggagcttc acgcttctag     780
ctgtcatgat tccaagattc tacgacatgt gggagaggat cctaaggttc ggggaaccgc     840
ggaggtttcg gggttctaga aatccgaggt tctaagccta ggtgctccaa taaacccagt     900
gagagccagc ccaggtttcc ggtctgtacc cgctggtgca agcccagaga caagcaggcg     960
ccacccatga gccctctgc ggccccctcc cgggtcccac ctcgcaggcc agctggaggg    1020
cgcgatcctg gcgtcccccg acggcctggg gccccaatcc agaggcctgg gtgggagggg    1080
accaagggtg tagtaaggaa gcgccttttg ctggagggca acggaccggg gcggggagtc    1140
gggagaccag agtgggagga aggcgggag tccaggttcc gccccggagc cgacttcctc    1200
ctggtcggcg gctgcagcgg ggtgagcggc ggcagcggcc ggggatcctg gagccatggg    1260
gcgcgcgcgc gacgccatcc tggatgcgct ggagaacctg accgccgagg agctcaagaa    1320
gttcaagctg aagctgctgt cggtgccgct gcgcgagggc tacgggcgca tcccgcgggg    1380
cgcgctgctg tccatggacg ccttggacct caccgacaag ctggtcagct tctacctgga    1440
gacctacggc gccgagctca ccgctaacgt gctgcgcgac atgggcctgc aggagatggc    1500
cgggcagctg caggcggcca cgcaccaggg tgagccgccc ccgttcccct ccaccccgtc    1560
tttcccctcc acccacacca gcgcttaccc cgcgggctct tccgctttct gttcctccta    1620
cccctaaaca aagctgctct accggaaagg aggctcccca cgcttggcct accgaccaac    1680
gggaccccgg ccccacggcg ggaagggaag ggaagggat cacttggccc atatccttcc    1740
```

-continued

```
aggctctgga gccgcgccag ctgggatcca ggcccctcct cagtcggcag ccaagccagg    1800
tgaggcctcc acacccagcc cggccccacc gcactcctgc acagcctgca tctgtgctcc    1860
cgcaaccagg gcagggcagg gcagggcagg cacggcttgg caaccctgcg cacccacct    1920 accaacccac accctgcggg ggaagggaga caatattacc ctcatcccac tgcatgtggg    1980
gtcctggtgg ccgcccctg gagccctgcc cctaggcttg cagaggaatt cctgaagaac    2040
tcaagttcag cagggacagg ccccacaccc tggctgctgg ctcatgttct cctcccaccc    2100
ccaggcctgc actttataga ccagcaccgg gctgcgctta cgcgagggt cacaaacgtt    2160 gagtggctgc tggatgctct gtacgggaag gtcctgacgg atgagcagta ccaggcagtg    2220
cgggccgagc ccaccaaccc aagcaagatg cggaagctct tcagtttcac accagcctgg    2280
aactggacct gcaaggactt gctcctccag gccctaaggg agtcccagtc ctacctggtg    2340
gaggacctgg agcggagctg aggctccttc ccagcaacac tccggtcagc cctggcaat    2400 cccaccaaat catcctgaat ctgatctttt tatacacaat atacgaaaag ccagcttgaa    2460
cttgtgtgtt ttcctgcttc tagcctgctg gcatgtgcag agctcagcta tgcttcagag    2520
gccacccagc ctccagctcc atgtcccctag ggtctctggc accccaaatg cttcccccat    2580
ccttcctggt atcgccatgg aatatccctc ctcattcacc aggtggtgct cctccagtgc    2640
tccctaaagg gtctaacctt accattatag ataacagcct gtgacccagg tccgaaggtt    2700
aaaagaggca tgtaccaaag gcgcaaact ggtgggcagc tctgtccaag ccatttagaa    2760
acacactagt cttcatagct cccctacctt ccacattttc cactggaaga aaaaatggca    2820
a                                                                    2821
```

```
<210> SEQ ID NO 2
<211> LENGTH: 770
<212> TYPE: DNA
<213> ORGANISM: Homo Sapiens
<220> FEATURE:
<221> NAME/KEY: CDS
<222> LOCATION: (75)...(662)

<400> SEQUENCE: 2
ccacgcgtcc gacttcctcc tggtcggcgg ctgcagcggg gtgagcggcg gcagcggccg    60
gggatcctgg agcc atg ggg cgc gcg cgc gac gcc atc ctg gat gcg ctg    110
         Met Gly Arg Ala Arg Asp Ala Ile Leu Asp Ala Leu
         1               5                   10 gag aac ctg acc gcc gag gag ctc aag aag ttc aag ctg aag ctg ctg    158
Glu Asn Leu Thr Ala Glu Glu Leu Lys Lys Phe Lys Leu Lys Leu Leu
            15                  20                  25 tcg gtg ccg ctg cgc gag ggc tac ggg cgc atc ccg cgg ggc gcg ctg    206
Ser Val Pro Leu Arg Glu Gly Tyr Gly Arg Ile Pro Arg Gly Ala Leu
        30                  35                  40 ctg tcc atg gac gcc ttg gac ctc acc gac aag ctg gtc agc ttc tac    254
Leu Ser Met Asp Ala Leu Asp Leu Thr Asp Lys Leu Val Ser Phe Tyr
    45                  50                  55                  60 ctg gag acc tac ggc gcc gag ctc acc gct aac gtg ctg cgc gac atg    302
Leu Glu Thr Tyr Gly Ala Glu Leu Thr Ala Asn Val Leu Arg Asp Met
                65                  70                  75 ggc ctg cag gag atg gcc ggg cag ctg cag gcg gcc acg cac cag ggc    350
Gly Leu Gln Glu Met Ala Gly Gln Leu Gln Ala Ala Thr His Gln Gly
            80                  85                  90 tct gga gcc gcg cca gct ggg atc cag gcc cct cct cag tcg gca gcc    398
Ser Gly Ala Ala Pro Ala Gly Ile Gln Ala Pro Pro Gln Ser Ala Ala
        95                  100                 105
```

```
aag cca ggc ctg cac ttt ata gac cag cac cgg gct gcg ctt atc gcg    446
Lys Pro Gly Leu His Phe Ile Asp Gln His Arg Ala Ala Leu Ile Ala
    110                 115                 120 agg gtc aca aac gtt gag tgg ctg ctg gat gct ctg tac ggg aag gtc    494
Arg Val Thr Asn Val Glu Trp Leu Leu Asp Ala Leu Tyr Gly Lys Val
125                 130                 135                 140 ctg acg gat gag cag tac cag gca gtg cgg gcc gag ccc acc aac cca    542
Leu Thr Asp Glu Gln Tyr Gln Ala Val Arg Ala Glu Pro Thr Asn Pro
                145                 150                 155 agc aag atg cgg aag ctc ttc agt ttc aca cca gcc tgg aac tgg acc    590
Ser Lys Met Arg Lys Leu Phe Ser Phe Thr Pro Ala Trp Asn Trp Thr
            160                 165                 170 tgc aag gac ttg ctc ctc cag gcc cta agg gag tcc cag tcc tac ctg    638
Cys Lys Asp Leu Leu Leu Gln Ala Leu Arg Glu Ser Gln Ser Tyr Leu
        175                 180                 185 gtg gag gac ctg gag cgg agc tga ggctccttcc cagcaacact ccggtcagcc   692
Val Glu Asp Leu Glu Arg Ser  *
    190                 195 cctggcaatc ccaccaaatc atcctgaatc tgatctttt atacacaata tacgaaaagc    752
cagcttgaaa aaaaaaaa                                                  770

<210> SEQ ID NO 3
<211> LENGTH: 195
<212> TYPE: PRT
<213> ORGANISM: Homo Sapiens

<400> SEQUENCE: 3

Met Gly Arg Ala Arg Asp Ala Ile Leu Asp Ala Leu Glu Asn Leu Thr
 1               5                  10                  15

Ala Glu Glu Leu Lys Lys Phe Lys Leu Lys Leu Leu Ser Val Pro Leu
            20                  25                  30

Arg Glu Gly Tyr Gly Arg Ile Pro Arg Gly Ala Leu Leu Ser Met Asp
        35                  40                  45

Ala Leu Asp Leu Thr Asp Lys Leu Val Ser Phe Tyr Leu Glu Thr Tyr
    50                  55                  60

Gly Ala Glu Leu Thr Ala Asn Val Leu Arg Asp Met Gly Leu Gln Glu
65                  70                  75                  80

Met Ala Gly Gln Leu Gln Ala Ala Thr His Gln Gly Ser Gly Ala Ala
                85                  90                  95

Pro Ala Gly Ile Gln Ala Pro Pro Gln Ser Ala Ala Lys Pro Gly Leu
            100                 105                 110

His Phe Ile Asp Gln His Arg Ala Ala Leu Ile Ala Arg Val Thr Asn
        115                 120                 125

Val Glu Trp Leu Leu Asp Ala Leu Tyr Gly Lys Val Leu Thr Asp Glu
    130                 135                 140

Gln Tyr Gln Ala Val Arg Ala Glu Pro Thr Asn Pro Ser Lys Met Arg
145                 150                 155                 160

Lys Leu Phe Ser Phe Thr Pro Ala Trp Asn Trp Thr Cys Lys Asp Leu
                165                 170                 175

Leu Leu Gln Ala Leu Arg Glu Ser Gln Ser Tyr Leu Val Glu Asp Leu
            180                 185                 190

Glu Arg Ser
        195

<210> SEQ ID NO 4
<211> LENGTH: 626
<212> TYPE: DNA
```

-continued

```
<213> ORGANISM: Homo Sapiens

<400> SEQUENCE: 4
agcgcctttt gctggagggc aacggaccgg ggcggggagt cgggagacca gagtgggagg      60
aaggcgggga gtccaggttc cgccccggag ccgacttcct cctggtcggc ggctgcagcg     120
gggtgagcgg cggcagcggc cggggatcct ggagccatgg ggcgcgcgcg cgacgccatc     180
ctggatgcgc tggagaacct gaccgccgag gagctcaaga agttcaagct gaagctgctg     240
tcggtgccgc tgcgcgaggg ctacgggcgc atcccgcggg gcgcgctgct gtccatggac     300
gccttggacc tcaccgacaa gctggtcagc ttctacctgg agacctacgg cgccgagctc     360
accgctaacg tgctgcgcga catgggcctg caggagatgg ccgggcagct gcaggcggcc     420
acgcaccagg tgagccgcc cccgttcccc tccaccccgt ctttcccctc acccacacc      480 agcgcttacc ccgcgggctc ttccgctttc tgttcctcct accctaaac aaagctgctc     540 taccggaaag gaggctcccc acgcttggcc taccgaccaa cgggaccccg ccccacggc     600 gggaagggaa gggaagggga tcactt                                          626

<210> SEQ ID NO 5
<211> LENGTH: 340
<212> TYPE: DNA
<213> ORGANISM: Homo Sapiens
<220> FEATURE:
<221> NAME/KEY: CDS
<222> LOCATION: (67)...(339)

<400> SEQUENCE: 5
ccgacttcct cctggtcggc ggctgcagcg gggtgagcgg cggcagcggc cggggatcct      60 ggagcc atg ggg cgc gcg cgc gac gcc atc ctg gat gcg ctg gag aac       108
       Met Gly Arg Ala Arg Asp Ala Ile Leu Asp Ala Leu Glu Asn
         1               5                  10 ctg acc gcc gag gag ctc aag aag ttc aag ctg aag ctg ctg tcg gtg      156
Leu Thr Ala Glu Glu Leu Lys Lys Phe Lys Leu Lys Leu Leu Ser Val
 15                  20                  25                  30 ccg ctg cgc gag ggc tac ggg cgc atc ccg cgg ggc gcg ctg ctg tcc      204
Pro Leu Arg Glu Gly Tyr Gly Arg Ile Pro Arg Gly Ala Leu Leu Ser
                 35                  40                  45 atg gac gcc ttg gac ctc acc gac aag ctg gtc agc ttc tac ctg gag      252
Met Asp Ala Leu Asp Leu Thr Asp Lys Leu Val Ser Phe Tyr Leu Glu
             50                  55                  60 acc tac ggc gcc gag ctc acc gct aac gtg ctg cgc gac atg ggc ctg      300
Thr Tyr Gly Ala Glu Leu Thr Ala Asn Val Leu Arg Asp Met Gly Leu
         65                  70                  75 cag gag atg gcc ggg cag ctg cag gcg gcc acg cac cag g                340
Gln Glu Met Ala Gly Gln Leu Gln Ala Ala Thr His Gln
     80                  85                  90

<210> SEQ ID NO 6
<211> LENGTH: 91
<212> TYPE: PRT
<213> ORGANISM: Homo Sapiens

<400> SEQUENCE: 6

Met Gly Arg Ala Arg Asp Ala Ile Leu Asp Ala Leu Glu Asn Leu Thr
 1               5                  10                  15

Ala Glu Glu Leu Lys Lys Phe Lys Leu Lys Leu Leu Ser Val Pro Leu
             20                  25                  30

Arg Glu Gly Tyr Gly Arg Ile Pro Arg Gly Ala Leu Leu Ser Met Asp
         35                  40                  45
```

```
Ala Leu Asp Leu Thr Asp Lys Leu Val Ser Phe Tyr Leu Glu Thr Tyr
     50                  55                  60

Gly Ala Glu Leu Thr Ala Asn Val Leu Arg Asp Met Gly Leu Gln Glu
 65                  70                  75                  80

Met Ala Gly Gln Leu Gln Ala Ala Thr His Gln
                 85                  90

<210> SEQ ID NO 7
<211> LENGTH: 57
<212> TYPE: DNA
<213> ORGANISM: Homo Sapiens
<220> FEATURE:
<221> NAME/KEY: CDS
<222> LOCATION: (3)...(56)

<400> SEQUENCE: 7 gc tct gga gcc gcg cca gct ggg atc cag gcc cct cct cag tcg gca      47
   Ser Gly Ala Ala Pro Ala Gly Ile Gln Ala Pro Pro Gln Ser Ala
   1               5                  10                  15 gcc aag cca g                                                       57
Ala Lys Pro <210> SEQ ID NO 8
<211> LENGTH: 18
<212> TYPE: PRT
<213> ORGANISM: Homo Sapiens

<400> SEQUENCE: 8

Ser Gly Ala Ala Pro Ala Gly Ile Gln Ala Pro Pro Gln Ser Ala Ala
  1               5                  10                  15

Lys Pro

<210> SEQ ID NO 9
<211> LENGTH: 356
<212> TYPE: DNA
<213> ORGANISM: Homo Sapiens
<220> FEATURE:
<221> NAME/KEY: CDS
<222> LOCATION: (3)...(258)

<400> SEQUENCE: 9 gc ctg cac ttt ata gac cag cac cgg gct gcg ctt atc gcg agg gtc      47
   Leu His Phe Ile Asp Gln His Arg Ala Ala Leu Ile Ala Arg Val
   1               5                  10                  15 aca aac gtt gag tgg ctg ctg gat gct ctg tac ggg aag gtc ctg acg     95
Thr Asn Val Glu Trp Leu Leu Asp Ala Leu Tyr Gly Lys Val Leu Thr
                 20                  25                  30 gat gag cag tac cag gca gtg cgg gcc gag ccc acc aac cca agc aag    143
Asp Glu Gln Tyr Gln Ala Val Arg Ala Glu Pro Thr Asn Pro Ser Lys
             35                  40                  45 atg cgg aag ctc ttc agt ttc aca cca gcc tgg aac tgg acc tgc aag    191
Met Arg Lys Leu Phe Ser Phe Thr Pro Ala Trp Asn Trp Thr Cys Lys
         50                  55                  60 gac ttg ctc ctc cag gcc cta agg gag tcc cag tcc tac ctg gtg gag    239
Asp Leu Leu Leu Gln Ala Leu Arg Glu Ser Gln Ser Tyr Leu Val Glu
 65                  70                  75 gac ctg gag cgg agc tga g gctccttccc agcaacactc cggtcagccc         288
Asp Leu Glu Arg Ser   *
 80 ctggcaatcc caccaaatca tcctgaatct gatcttttta tacacaatat acgaaaagcc  348
agcttgaa                                                          356
```

<210> SEQ ID NO 10
<211> LENGTH: 84
<212> TYPE: PRT
<213> ORGANISM: Homo Sapiens

<400> SEQUENCE: 10

Leu His Phe Ile Asp Gln His Arg Ala Ala Leu Ile Ala Arg Val Thr
 1               5                  10                  15

Asn Val Glu Trp Leu Leu Asp Ala Leu Tyr Gly Lys Val Leu Thr Asp
            20                  25                  30

Glu Gln Tyr Gln Ala Val Arg Ala Glu Pro Thr Asn Pro Ser Lys Met
        35                  40                  45

Arg Lys Leu Phe Ser Phe Thr Pro Ala Trp Asn Trp Thr Cys Lys Asp
    50                  55                  60

Leu Leu Leu Gln Ala Leu Arg Glu Ser Gln Ser Tyr Leu Val Glu Asp
65                  70                  75                  80

Leu Glu Arg Ser

<210> SEQ ID NO 11
<211> LENGTH: 18
<212> TYPE: DNA
<213> ORGANISM: Homo Sapiens

<400> SEQUENCE: 11
gcactttata gaccagca                                                18

<210> SEQ ID NO 12
<211> LENGTH: 18
<212> TYPE: DNA
<213> ORGANISM: Homo Sapiens

<400> SEQUENCE: 12
atttggtggg attgccag                                                18

<210> SEQ ID NO 13
<211> LENGTH: 17
<212> TYPE: DNA
<213> ORGANISM: Homo Sapiens

<400> SEQUENCE: 13
tgggcctgca ggagatg                                                 17

<210> SEQ ID NO 14
<211> LENGTH: 22
<212> TYPE: DNA
<213> ORGANISM: Homo Sapiens

<400> SEQUENCE: 14
ccttcctggg catggagtcc tg                                           22

<210> SEQ ID NO 15
<211> LENGTH: 21
<212> TYPE: DNA
<213> ORGANISM: Homo Sapiens

<400> SEQUENCE: 15
ggagcaatga tcttgatctt c                                            21

<210> SEQ ID NO 16
<211> LENGTH: 21
<212> TYPE: DNA

```
<213> ORGANISM: Artificial Sequence
<220> FEATURE:
<223> OTHER INFORMATION: Synthetic Primer

<400> SEQUENCE: 16
ggttgtagtg gggtgagtgg t                                              21

<210> SEQ ID NO 17
<211> LENGTH: 25
<212> TYPE: DNA
<213> ORGANISM: Artificial Sequence
<220> FEATURE:
<223> OTHER INFORMATION: Synthetic Primer

<400> SEQUENCE: 17
caaaacatcc ataaacaaca acaca                                          25

<210> SEQ ID NO 18
<211> LENGTH: 19
<212> TYPE: DNA
<213> ORGANISM: Homo Sapiens

<400> SEQUENCE: 18
ttgtagcggg gtgagcggc                                                 19

<210> SEQ ID NO 19
<211> LENGTH: 22
<212> TYPE: DNA
<213> ORGANISM: Homo Sapiens

<400> SEQUENCE: 19
aacgtccata acaacaacg cg                                              22

<210> SEQ ID NO 20
<211> LENGTH: 803
<212> TYPE: DNA
<213> ORGANISM: Mus Musculus
<220> FEATURE:
<221> NAME/KEY: CDS
<222> LOCATION: (162)...(743)

<400> SEQUENCE: 20
gggaaagaac aggagctgta agaaaagagg gtgggggagt cccagcatgc ccatcggcct    60
aagcagctga cttcctggtc ttggcgggct ggcagcaggc aggctgagca ggcgagcagc   120
agcaagagta aaaggtgacc gcggctgccc accccagagc c atg ggg cgg gca cga   176
                                              Met Gly Arg Ala Arg
                                                1               5 gat gcc atc ctg gac gct ctt gaa aac ttg tca ggg gat gaa ctc aaa     224
Asp Ala Ile Leu Asp Ala Leu Glu Asn Leu Ser Gly Asp Glu Leu Lys
             10                  15                  20 aag ttc aag atg aag ctg ctg aca gtg caa ctg cga gaa ggc tat ggg     272
Lys Phe Lys Met Lys Leu Leu Thr Val Gln Leu Arg Glu Gly Tyr Gly
         25                  30                  35 cgc atc cca cgc ggg gcc ctg ctg cag atg gac gcc ata gat ctc act     320
Arg Ile Pro Arg Gly Ala Leu Leu Gln Met Asp Ala Ile Asp Leu Thr
     40                  45                  50 gac aaa ctt gtc agc tac tat ctg gag tcg tat ggc ttg gag ctc aca     368
Asp Lys Leu Val Ser Tyr Tyr Leu Glu Ser Tyr Gly Leu Glu Leu Thr
 55                  60                  65 atg act gtg ctt aga gac atg ggc tta cag gag ctg gct gag cag ctg     416
Met Thr Val Leu Arg Asp Met Gly Leu Gln Glu Leu Ala Glu Gln Leu
 70                  75                  80                  85
```

-continued

```
caa acg act aaa gaa gag tct gga gct gtg gca gct gca gcc agt gtc    464
Gln Thr Thr Lys Glu Glu Ser Gly Ala Val Ala Ala Ala Ala Ser Val
             90                  95                 100 cct gct cag agt aca gcc aga aca gga cac ttt gtg gac cag cac agg    512
Pro Ala Gln Ser Thr Ala Arg Thr Gly His Phe Val Asp Gln His Arg
            105                 110                 115 caa gca ctc att gcc agg gtc aca gaa gtg gac gga gtg ctg gat gct    560
Gln Ala Leu Ile Ala Arg Val Thr Glu Val Asp Gly Val Leu Asp Ala
        120                 125                 130 ttg cat ggc agt gtg ctg act gaa gga cag tac cag gca gtt cgt gca    608
Leu His Gly Ser Val Leu Thr Glu Gly Gln Tyr Gln Ala Val Arg Ala
    135                 140                 145 gag acc acc agc caa gac aag atg agg aag ctc ttc agc ttt gtt cca    656
Glu Thr Thr Ser Gln Asp Lys Met Arg Lys Leu Phe Ser Phe Val Pro
150                 155                 160                 165 tcc tgg aac ctg acc tgc aag gac tcc ctc ctc cag gcc ttg aag gaa    704
Ser Trp Asn Leu Thr Cys Lys Asp Ser Leu Leu Gln Ala Leu Lys Glu
                170                 175                 180 ata cat ccc tac ttg gtg atg gac ctg gag cag agc tga ggtatctttt    753
Ile His Pro Tyr Leu Val Met Asp Leu Glu Gln Ser  *
            185                 190 ccagctacat tatctagctc ctgactttgt atacacaatt tttgaaaaaa            803

<210> SEQ ID NO 21
<211> LENGTH: 193
<212> TYPE: PRT
<213> ORGANISM: Mus Musculus

<400> SEQUENCE: 21

Met Gly Arg Ala Arg Asp Ala Ile Leu Asp Ala Leu Glu Asn Leu Ser
 1               5                  10                  15

Gly Asp Glu Leu Lys Lys Phe Lys Met Lys Leu Leu Thr Val Gln Leu
             20                  25                  30

Arg Glu Gly Tyr Gly Arg Ile Pro Arg Gly Ala Leu Leu Gln Met Asp
         35                  40                  45

Ala Ile Asp Leu Thr Asp Lys Leu Val Ser Tyr Tyr Leu Glu Ser Tyr
     50                  55                  60

Gly Leu Glu Leu Thr Met Thr Val Leu Arg Asp Met Gly Leu Gln Glu
 65                  70                  75                  80

Leu Ala Glu Gln Leu Gln Thr Thr Lys Glu Glu Ser Gly Ala Val Ala
                 85                  90                  95

Ala Ala Ala Ser Val Pro Ala Gln Ser Thr Ala Arg Thr Gly His Phe
            100                 105                 110

Val Asp Gln His Arg Gln Ala Leu Ile Ala Arg Val Thr Glu Val Asp
        115                 120                 125

Gly Val Leu Asp Ala Leu His Gly Ser Val Leu Thr Glu Gly Gln Tyr
    130                 135                 140

Gln Ala Val Arg Ala Glu Thr Thr Ser Gln Asp Lys Met Arg Lys Leu
145                 150                 155                 160

Phe Ser Phe Val Pro Ser Trp Asn Leu Thr Cys Lys Asp Ser Leu Leu
                165                 170                 175

Gln Ala Leu Lys Glu Ile His Pro Tyr Leu Val Met Asp Leu Glu Gln
            180                 185                 190

Ser

<210> SEQ ID NO 22
<211> LENGTH: 605
```

```
<212> TYPE: DNA
<213> ORGANISM: Rattus Norvegicus
<220> FEATURE:
<221> NAME/KEY: CDS
<222> LOCATION: (2)...(518)
<221> NAME/KEY: Variant
<222> LOCATION: (109)...(109)
<223> OTHER INFORMATION: y = C or T/U

<400> SEQUENCE: 22 t ttc aag ata aag ctg ctg aca gcg cca gtg cgg gaa ggc tat ggg cgc         49
  Phe Lys Ile Lys Leu Leu Thr Ala Pro Val Arg Glu Gly Tyr Gly Arg
   1               5                  10                  15 atc cca cgg ggg gcc ctg ctg cag atg gac ccc ata gac ctc act gat          97
Ile Pro Arg Gly Ala Leu Leu Gln Met Asp Pro Ile Asp Leu Thr Asp
             20                  25                  30 aaa ctc gtc agy tac tat ctg gag ggg tat ggc ttg gag ctc aca atg         145
Lys Leu Val Xaa Tyr Tyr Leu Glu Gly Tyr Gly Leu Glu Leu Thr Met
         35                  40                  45 act gtg ctt aga gac atg ggc ata cag gag ctg gct gag cag ctg caa         193
Thr Val Leu Arg Asp Met Gly Ile Gln Glu Leu Ala Glu Gln Leu Gln
     50                  55                  60 aag att atg gaa gag tct gga gct gtg gct act gca acc agt gtc cct         241
Lys Ile Met Glu Glu Ser Gly Ala Val Ala Thr Ala Thr Ser Val Pro
 65                  70                  75                  80 gct cag ggc aca gcc aga aca gaa cat ttt gtg gac caa cac agg caa         289
Ala Gln Gly Thr Ala Arg Thr Glu His Phe Val Asp Gln His Arg Gln
                 85                  90                  95 gca ctc att gcc agg gtc aca gaa gtt gat ggt ttg ctg gat gct ctg         337
Ala Leu Ile Ala Arg Val Thr Glu Val Asp Gly Leu Leu Asp Ala Leu
            100                 105                 110 tat ggc aat gtg ctg act gaa gga cag tac cag gca gtt cgt gca gag         385
Tyr Gly Asn Val Leu Thr Glu Gly Gln Tyr Gln Ala Val Arg Ala Glu
        115                 120                 125 acc acc aac caa aac aag atg agg aag ctc ttt agc ttt gct cca gcc         433
Thr Thr Asn Gln Asn Lys Met Arg Lys Leu Phe Ser Phe Ala Pro Ala
    130                 135                 140 tgg aac ctg acc tgc aag aac ttg ttc ctt gag gcc ttg agg caa aca         481
Trp Asn Leu Thr Cys Lys Asn Leu Phe Leu Glu Ala Leu Arg Gln Thr
145                 150                 155                 160 cag ccc tac ttg gtg aca gac ctg gaa cag agc tga g gtatcttttc            528
Gln Pro Tyr Leu Val Thr Asp Leu Glu Gln Ser  *
                165                 170 cagctacaca tctagctcct ggttttgtat acaaattttt ctaaaaacaa gtttgtattt       588
gtgttttctc gaaaaaa                                                     605

<210> SEQ ID NO 23
<211> LENGTH: 171
<212> TYPE: PRT
<213> ORGANISM: Rattus Norvegicus
<220> FEATURE:
<221> NAME/KEY: Unknown
<222> LOCATION: (36)...(36)
<223> OTHER INFORMATION: Xaa can be any amino acid.

<400> SEQUENCE: 23

Phe Lys Ile Lys Leu Leu Thr Ala Pro Val Arg Glu Gly Tyr Gly Arg
  1               5                  10                  15

Ile Pro Arg Gly Ala Leu Leu Gln Met Asp Pro Ile Asp Leu Thr Asp
             20                  25                  30

Lys Leu Val Xaa Tyr Tyr Leu Glu Gly Tyr Gly Leu Glu Leu Thr Met
         35                  40                  45
```

```
Thr Val Leu Arg Asp Met Gly Ile Gln Glu Leu Ala Glu Gln Leu Gln
 50                  55                  60

Lys Ile Met Glu Glu Ser Gly Ala Val Ala Thr Ala Thr Ser Val Pro
 65                  70                  75                  80

Ala Gln Gly Thr Ala Arg Thr Glu His Phe Val Asp Gln His Arg Gln
                 85                  90                  95

Ala Leu Ile Ala Arg Val Thr Val Asp Gly Leu Leu Asp Ala Leu
                100                 105                 110

Tyr Gly Asn Val Leu Thr Glu Gly Gln Tyr Gln Ala Val Arg Ala Glu
            115                 120                 125

Thr Thr Asn Gln Asn Lys Met Arg Lys Leu Phe Ser Phe Ala Pro Ala
130                 135                 140

Trp Asn Leu Thr Cys Lys Asn Leu Phe Leu Glu Ala Leu Arg Gln Thr
145                 150                 155                 160

Gln Pro Tyr Leu Val Thr Asp Leu Glu Gln Ser
                165                 170

<210> SEQ ID NO 24
<211> LENGTH: 713
<212> TYPE: DNA
<213> ORGANISM: Homo Sapiens
<220> FEATURE:
<221> NAME/KEY: CDS
<222> LOCATION: (75)...(605)

<400> SEQUENCE: 24
```

| | |
|---|---|
| ccacgcgtcc gacttcctcc tggtcggcgg ctgcagcggg gtgagcggcg gcagcggccg | 60 |
| gggatcctgg agcc atg ggg cgc gcg cgc gac gcc atc ctg gat gcg ctg<br>                 Met Gly Arg Ala Arg Asp Ala Ile Leu Asp Ala Leu<br>                  1         5          10 | 110 |
| gag aac ctg acc gcc gag gag ctc aag aag ttc aag ctg aag ctg ctg<br>Glu Asn Leu Thr Ala Glu Glu Leu Lys Lys Phe Lys Leu Lys Leu Leu<br>        15               20             25 | 158 |
| tcg gtg ccg ctg cgc gag ggc tac ggg cgc atc ccg cgg ggc gcg ctg<br>Ser Val Pro Leu Arg Glu Gly Tyr Gly Arg Ile Pro Arg Gly Ala Leu<br> 30              35             40 | 206 |
| ctg tcc atg gac gcc ttg gac ctc acc gac aag ctg gtc agc ttc tac<br>Leu Ser Met Asp Ala Leu Asp Leu Thr Asp Lys Leu Val Ser Phe Tyr<br> 45              50             55             60 | 254 |
| ctg gag acc tac ggc gcc gag ctc acc gct aac gtg ctg cgc gac atg<br>Leu Glu Thr Tyr Gly Ala Glu Leu Thr Ala Asn Val Leu Arg Asp Met<br>               65              70             75 | 302 |
| ggc ctg cag gag atg gcc ggg cag ctg cag gcg gcc acg cac cag ggc<br>Gly Leu Gln Glu Met Ala Gly Gln Leu Gln Ala Ala Thr His Gln Gly<br>             80              85             90 | 350 |
| ctg cac ttt ata gac cag cac cgg gct gcg ctt atc gcg agg gtc aca<br>Leu His Phe Ile Asp Gln His Arg Ala Ala Leu Ile Ala Arg Val Thr<br>        95              100           105 | 398 |
| aac gtt gag tgg ctg ctg gat gct ctg tac ggg aag gtc ctg acg gat<br>Asn Val Glu Trp Leu Leu Asp Ala Leu Tyr Gly Lys Val Leu Thr Asp<br>110             115             120 | 446 |
| gag cag tac cag gca gtg cgg gcc gag ccc acc aac cca agc aag atg<br>Glu Gln Tyr Gln Ala Val Arg Ala Glu Pro Thr Asn Pro Ser Lys Met<br>125             130             135            140 | 494 |
| cgg aag ctc ttc agt ttc aca cca gcc tgg aac tgg acc tgc aag gac<br>Arg Lys Leu Phe Ser Phe Thr Pro Ala Trp Asn Trp Thr Cys Lys Asp<br>               145             150            155 | 542 |
| ttg ctc ctc cag gcc cta agg gag tcc cag tcc tac ctg gtg gag gac | 590 |

-continued

```
                Leu Leu Leu Gln Ala Leu Arg Glu Ser Gln Ser Tyr Leu Val Glu Asp
                            160                 165                 170 ctg gag cgg agc tga ggctccttcc cagcaacact ccgtcagcc cctggcaatc        645
Leu Glu Arg Ser *
        175 ccaccaaatc atcctgaatc tgatcttttt atacacaata tacgaaaagc cagcttgaaa     705 aaaaaaaa                                                              713

<210> SEQ ID NO 25
<211> LENGTH: 176
<212> TYPE: PRT
<213> ORGANISM: Homo Sapiens

<400> SEQUENCE: 25

Met Gly Arg Ala Arg Asp Ala Ile Leu Asp Ala Leu Glu Asn Leu Thr
  1               5                  10                  15

Ala Glu Glu Leu Lys Lys Phe Lys Leu Lys Leu Leu Ser Val Pro Leu
             20                  25                  30

Arg Glu Gly Tyr Gly Arg Ile Pro Arg Gly Ala Leu Leu Ser Met Asp
         35                  40                  45

Ala Leu Asp Leu Thr Asp Lys Leu Val Ser Phe Tyr Leu Glu Thr Tyr
     50                  55                  60

Gly Ala Glu Leu Thr Ala Asn Val Leu Arg Asp Met Gly Leu Gln Glu
 65                  70                  75                  80

Met Ala Gly Gln Leu Gln Ala Ala Thr His Gln Gly Leu His Phe Ile
                 85                  90                  95

Asp Gln His Arg Ala Ala Leu Ile Ala Arg Val Thr Asn Val Glu Trp
            100                 105                 110

Leu Leu Asp Ala Leu Tyr Gly Lys Val Leu Thr Asp Glu Gln Tyr Gln
        115                 120                 125

Ala Val Arg Ala Glu Pro Thr Asn Pro Ser Lys Met Arg Lys Leu Phe
    130                 135                 140

Ser Phe Thr Pro Ala Trp Asn Trp Thr Cys Lys Asp Leu Leu Leu Gln
145                 150                 155                 160

Ala Leu Arg Glu Ser Gln Ser Tyr Leu Val Glu Asp Leu Glu Arg Ser
                165                 170                 175

<210> SEQ ID NO 26
<211> LENGTH: 405
<212> TYPE: DNA
<213> ORGANISM: Homo Sapiens
<220> FEATURE:
<221> NAME/KEY: CDS
<222> LOCATION: (75)...(404)

<400> SEQUENCE: 26
ccacgcgtcc gacttcctcc tggtcggcgg ctgcagcggg gtgagcggcg gcagcggccg     60
gggatcctgg agcc atg ggg cgc gcg cgc gac gcc atc ctg gat gcg ctg      110
                Met Gly Arg Ala Arg Asp Ala Ile Leu Asp Ala Leu
                  1               5                  10 gag aac ctg acc gcc gag gag ctc aag aag ttc aag ctg aag ctg ctg      158
Glu Asn Leu Thr Ala Glu Glu Leu Lys Lys Phe Lys Leu Lys Leu Leu
          15                  20                  25 tcg gtg ccg ctg cgc gag ggc tac ggg cgc atc ccg cgg ggc gcg ctg      206
Ser Val Pro Leu Arg Glu Gly Tyr Gly Arg Ile Pro Arg Gly Ala Leu
     30                  35                  40 ctg tcc atg gac gcc ttg gac ctc acc gac aag ctg gtc agc ttc tac      254
Leu Ser Met Asp Ala Leu Asp Leu Thr Asp Lys Leu Val Ser Phe Tyr
```

```
                45                  50                  55                  60
ctg gag acc tac ggc gcc gag ctc acc gct aac gtg ctg cgc gac atg         302
Leu Glu Thr Tyr Gly Ala Glu Leu Thr Ala Asn Val Leu Arg Asp Met
                    65                  70                  75 ggc ctg cag gag atg gcc ggg cag ctg cag gcg gcc acg cac cag ggc         350
Gly Leu Gln Glu Met Ala Gly Gln Leu Gln Ala Ala Thr His Gln Gly
                80                  85                  90 tct gga gcc gcg cca gct ggg atc cag gcc cct cct cag tcg gca gcc         398
Ser Gly Ala Ala Pro Ala Gly Ile Gln Ala Pro Pro Gln Ser Ala Ala
            95                  100                 105 aag cca g                                                               405
Lys Pro
    110

<210> SEQ ID NO 27
<211> LENGTH: 110
<212> TYPE: PRT
<213> ORGANISM: Homo Sapiens

<400> SEQUENCE: 27

Met Gly Arg Ala Arg Asp Ala Ile Leu Asp Ala Leu Glu Asn Leu Thr
 1               5                  10                  15

Ala Glu Glu Leu Lys Lys Phe Lys Leu Lys Leu Leu Ser Val Pro Leu
                20                  25                  30

Arg Glu Gly Tyr Gly Arg Ile Pro Arg Gly Ala Leu Leu Ser Met Asp
            35                  40                  45

Ala Leu Asp Leu Thr Asp Lys Leu Val Ser Phe Tyr Leu Glu Thr Tyr
        50                  55                  60

Gly Ala Glu Leu Thr Ala Asn Val Leu Arg Asp Met Gly Leu Gln Glu
65                  70                  75                  80

Met Ala Gly Gln Leu Gln Ala Ala Thr His Gln Gly Ser Gly Ala Ala
                85                  90                  95

Pro Ala Gly Ile Gln Ala Pro Pro Gln Ser Ala Ala Lys Pro
                100                 105                 110
```